United States Patent
Ancliff et al.

(10) Patent No.: US 7,622,464 B2
(45) Date of Patent: Nov. 24, 2009

(54) MORPHOLINYL-UREA DERIVATIVES FOR USE IN THE TREATMENT OF INFLAMMATORY DISEASES

(75) Inventors: Rachael Ann Ancliff, Stevenage (GB); Caroline Mary Cook, Stevenage (GB); Colin David Eldred, Stevenage (GB); Paul Martin Gore, Stevenage (GB); Lee Andrew Harrison, Stevenage (GB); Martin Alistair Hayes, Stevenage (GB); Simon Teanby Hodgson, Stevenage (GB); Duncan Bruce Judd, Stevenage (GB); Suzanne Elaine Keeling, Stevenage (GB); Xiao Qing Lewell, Stevenage (GB); Gail Mills, Stevenage (GB); Graeme Michael Robertson, Stevenage (GB); Stephen Swanson, Stevenage (GB); Andrew John Walker, Stevenage (GB); Mark Wilkinson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 444 days.

(21) Appl. No.: 10/509,162

(22) PCT Filed: Mar. 27, 2003

(86) PCT No.: PCT/EP03/03335

§ 371 (c)(1),
(2), (4) Date: Jun. 10, 2005

(87) PCT Pub. No.: WO03/082861

PCT Pub. Date: Oct. 9, 2003

(65) Prior Publication Data

US 2006/0063765 A1  Mar. 23, 2006

(30) Foreign Application Priority Data

Mar. 28, 2002 (GB) ................. 0207434.2
Jan. 24, 2003 (GB) ................. 0301608.6

(51) Int. Cl.
*A61K 31/535* (2006.01)
*C07D 413/14* (2006.01)
*C07D 413/12* (2006.01)

(52) U.S. Cl. ................. 514/231.5; 514/236.2; 544/132; 544/138; 544/146; 544/162

(58) Field of Classification Search ............. 514/236.2, 514/231.5; 544/138, 132, 146, 162
See application file for complete search history.

(56) References Cited

U.S. PATENT DOCUMENTS 5,389,635 A  2/1995  Olson
5,919,776 A  7/1999  Hagmann et al.
6,031,097 A  2/2000  He et al.

FOREIGN PATENT DOCUMENTS

| EP | 0306440 | 3/1989 |
|----|---------|--------|
| JP | 04208267 | 7/1992 |
| WO | WO 95/32196 | 11/1995 |
| WO | WO 96/02534 | 2/1996 |
| WO | WO 96/39386 | 12/1996 |
| WO | WO 97/47601 | 12/1997 |
| WO | WO 98/56771 | 12/1998 |
| WO | WO 99/06384 | 2/1999 |
| WO | WO 99/21848 | 5/1999 |
| WO | WO 00/18767 | 4/2000 |
| WO | WO 02/26722 | 4/2002 |
| WO | WO 02/26723 | 4/2002 |

OTHER PUBLICATIONS

Byrn et al., Solid-State Chemistry of Drugs, Second Edition, 1999, pp. 233-247.*
Dressman et al., "Solid phase synthesis of urea libraries using a diversifiable thiophenoxy carbonyl linker," *Tetrahedron Letters* 39(22):3631-3634 (May 1998).
Makabe et al., "Synthesis of some nucleoside analogs of substituted 1,2,3-triazole," *Bull. Chem. Soc. Jap.* 45(8):2577-2579 (1972).

* cited by examiner

*Primary Examiner*—Rebecca L Anderson
(74) *Attorney, Agent, or Firm*—James P. Rick

(57) ABSTRACT

Compounds of formula (I):

$$R^1-Y-N(R^3)-C(=O)-N(R^4)-CH_2-\text{morpholine}$$

(I)

wherein:
$R^1$ represents substituted or unsubstituted heteroaryl;
Y represents $-(CR_{na}R_{nb})_n-$;
$R_{na}$ and $R_{nb}$ are each independently hydrogen or $C_{1-6}$alkyl;
n is an integer from 0 to 5;
$R^2$ represents unsubstituted or substituted aryl or unsubstituted or substituted heteroaryl;
$R^3$ and $R^4$ each independently represent hydrogen or $C_{1-6}$-alkyl;
$R^7$ represents hydrogen or $C_{1-6}$alkyl;
$R^8$ represents hydrogen or $C_{1-6}$alkyl;
and salts and solvates thereof;
are CCR3 antagonists and are thus indicated to be useful in therapy.

12 Claims, No Drawings

MORPHOLINYL-UREA DERIVATIVES FOR USE IN THE TREATMENT OF INFLAMMATORY DISEASES

CROSS-REFERENCE TO RELATED APPLICATIONS

This application is filed pursuant to 35 USC 371 as a United States National Phase Application of International Patent Application Serial No. PCT/EP03/03335 filed on 27 Mar. 2003, which claims priority from GB 0207434.2 filed on 28 Mar. 2002 and GB 0301608.6 filed on 24 Jan. 2003, both in the United Kingdom.

FIELD OF THE INVENTION

This invention relates to novel compounds, processes for their preparation, pharmaceutical formulations containing them and their use in therapy.

BACKGROUND OF THE INVENTION

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms, such as bacteria and parasites. Once a tissue is injured or infected, a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction. There is increasing evidence that the bronchial inflammation which is characteristic of asthma represents a specialised form of cell-mediated immunity, in which cytokine products, such as IL-4 and IL-5 released by T-helper 2 (Th2) lymphocytes, orchestrate the accumulation and activation of granulocytes, in particular eosinophils and to a lesser extent basophils. Through the release of cytotoxic basic proteins, pro-inflammatory mediators and oxygen radicals, eosinophils generate mucosal damage and initiate mechanisms that underlie bronchial hyperreactivity. Therefore, blocking the recruitment and activation of Th2 cells and eosinophils is likely to have anti-inflammatory properties in asthma. In addition, eosinophils have been implicated in other disease types such as rhinitis, eczema, irritable bowel syndrome and parasitic infections.

Chemokines are a large family of small proteins which are involved in trafficking and recruitment of leukocytes (for review see Luster, New Eng. J. Med., 338, 436-445 (1998)). They are released by a wide variety of cells and act to attract and activate various cell types, including eosinophils, basophils, neutrophils, macrophages, T and B lymphocytes. There are two major families of chemokines, CXC- (α) and CC- (β) chemokines, classified according to the spacing of two conserved cysteine residues near to the amino terminus of the chemokine proteins. Chemokines bind to specific cell surface receptors belonging to the family of G-protein-coupled seven transmembrane-domain proteins (for review see Luster, 1998). Activation of chemokine receptors results in, amongst other responses, an increase in intracellular calcium, changes in cell shape, increased expression of cellular adhesion molecules, degranulation and promotion of cell migration (chemotaxis).

To date a number of CC chemokine receptors have been identified and of particular importance to the current invention is the CC-chemokine receptor-3 (CCR-3), which is predominantly expressed on eosinophils, and also on basophils, mast cells and Th2 cells. Chemokines that act at CCR-3, such as RANTES, MCP-3 and MCP-4, are known to recruit and activate eosinophils. Of particular interest are eotaxin and eotaxin-2, which specifically bind to CCR-3. The localization and function of CCR-3 chemokines indicate that they play a central role in the development of allergic diseases such as asthma. Thus, CCR-3 is specifically expressed on all the major cell types involved in inflammatory allergic responses. Chemokines that act at CCR-3 are generated in response to inflammatory stimuli and act to recruit these cell types to sites of inflammation, where they cause their activation (e.g. Griffiths et al., J. Exp. Med., 179, 881-887 (1994), Lloyd et al., J. Exp. Med., 191, 265-273 (2000)). In addition, anti-CCR-3 monoclonal antibodies completely inhibit eotaxin interaction with eosinophils (Heath, H. et al., J. Clin. Invest. 99 (2), 178-184 (1997)), while an antibody for the CCR-3 specific chemokine, eotaxin, reduced both bronchial hyperreactivity and lung eosinophilia in an animal model of asthma (Gonzalo et al., J. Exp. Med., 188, 157-167 (1998). Thus, many lines of evidence indicate that antagonists at the CCR-3 receptor are very likely to be of therapeutic use for the treatment of a range of inflammatory conditions.

In addition to a key role in inflammatory disorders, chemokines and their receptors also play a role in infectious disease. Mammalian cytomegaloviruses, herpes viruses and pox viruses express chemokine receptor homologues, which can be activated by human CC chemokines such as RANTES and MCP-3 receptors (for review see Wells and Schwartz, Curr. Opin. Biotech., 8, 741-748, 1997). In addition, human chemokine receptors, such as CXCR-4, CCR-5 and CCR-3, can act as co-receptors for the infection of mammalian cells by microbes such as human immunodeficiency viruses (HIV). Thus, chemokine receptor antagonists, including CCR-3 antagonists, may be useful in blocking infection of CCR-3 expressing cells by HIV or in preventing the manipulation of immune cellular responses by viruses such as cytomegaloviruses.

International Patent Application publication number WO 01/24786 (Shionogi & Co. Ltd.) discloses certain aryl and heteroaryl derivatives for treating diabetes. WO 00/69830 (Torrey Pines Institute for Molecular Studies) discloses certain diazacyclic compounds, and libraries containing them, for biological screening. WO 00/18767 (Neurogen Corporation) discloses certain piperazine derivatives as dopamine D4 receptor antagonists. U.S. Pat. No. 6,031,097 and WO 99/21848 (Neurogen Corporation) discloses certain aminoisoquinoline derivatives as dopamine receptor ligands. WO 99/06384 (Recordati Industria Chimica) discloses piperazine derivatives useful for the treatment of neuromuscular dysfunction of the lower urinary tract. WO 98/56771 (Schering Aktiengesellschaft) discloses certain piperazine derivatives as anti-inflammatory agents. WO 97/47601 (Yoshitomi Pharmaceutical Industries Ltd.) discloses certain fused heterocyclic compounds as dopamine D-receptor blocking agents.

WO 96/39386 (Schering Corporation) discloses certain piperidine derivatives as neurokinin antagonists. WO 96/02534 (Byk Gulden Lomberg Chemische Fabrik GmbH) discloses certain piperazine thiopyridines useful for controlling helicobacter bacteria. WO 95/32196 (Merck Sharp & Dohme Limited) discloses certain piperazine, piperidine, and tetrahydropyridine derivatives as 5-HT1D-alpha antagonists. U.S. Pat. No. 5,389,635 (E.I. Du Pont de Nemours and Company) discloses certain substituted imadazoles as angiotensin-II antagonists. European Patent Application publication number 0 306 440 (Schering Aktiengesellschaft) discloses certain imidazole derivatives as cardiovascular agents.

A novel group of compounds has now been found which are CCR-3 antagonists. These compounds block the migration/chemotaxis of eosinophils and thus possess anti-inflammatory properties. These compounds are therefore of potential therapeutic benefit, especially in providing protection from eosinophil, basophil mast cell and Th2-cell-induced tissue damage in diseases where such cell types are implicated, particularly allergic diseases, including but not limited to bronchial asthma, allergic rhinitis and atopic dermatitis.

SUMMARY OF THE INVENTION

Thus, according to one aspect of the invention, there are provided compounds of formula (I):

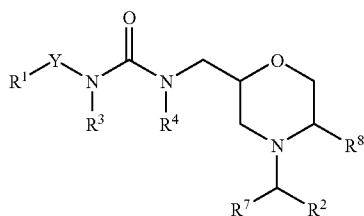

wherein:
R$^1$ represents substituted or unsubstituted heteroaryl;
Y represents —(CR$_{na}$R$_{nb}$)$_n$—;
R$_{na}$ and R$_{nb}$ are each independently hydrogen or C$_{1-6}$alkyl;
n is an integer from 0 to 5;
R$^2$ represents unsubstituted or substituted aryl or unsubstituted or substituted heteroaryl;
R$^3$ and R$^4$ each independently represent hydrogen or C$_{1-6}$alkyl;
R$^7$ represents hydrogen or C$_{1-6}$alkyl;
R$^8$ represents hydrogen or C$_{1-6}$-alkyl;

and salts and solvates thereof;

with the proviso that the following compounds are excluded;
N-{[4-(3,4-dichlorobenzyl)morpholin-2-yl]methyl}-N'-(pyridin-3-ylmethyl)urea;
N-{[4-(3,4-dichlorobenzyl)morpholin-2-yl]methyl}-N'-[(6-methoxypyridin-3-yl)methyl]urea;
5-({[({[4-(3,4-dichlorobenzyl)morpholin-2-yl]methyl}amino)carbonyl]-amino}methyl)nicotinamide;
N-{[4-(3,4-dichlorobenzyl)morpholin-2-yl]methyl}-N'-(1H-indol-5-ylmethyl)urea;
N-{[4-(3,4-dichlorobenzyl)morpholin-2-yl]methyl}-N'-(1H-indol-4-ylmethyl)urea;
N-{[4-(3,4-dichlorobenzyl)morpholin-2-yl]methyl}-N'-[(5-methylisoxazol-3-yl)methyl]urea;
N-{[4-(3,4-dichlorobenzyl)morpholin-2-yl]methyl}-N'-(thien-2-ylmethyl)urea;
N-{[4-(3,4-dichlorobenzyl)morpholin-2-yl]methyl}-N'-(2-thien-2-ylethyl)urea;
N-{[4-(3,4-dichlorobenzyl)morpholin-2-yl]methyl}-N'-({5-[(dimethylamino)methyl]-2-furyl}methyl)urea;
N-{[4-(3,4-dichlorobenzyl)morpholin-2-yl]methyl}-N'-[(3-methoxyisothiazol-5-yl)methyl]urea;
N-{[4-(3,4-dichlorobenzyl)morpholin-2-yl]methyl}-N'-[(4-methyl-1,3-thiazol-2-yl)methyl]urea;
N-{[4-(3,4-dichlorobenzyl)morpholin-2-yl]methyl}-N'-(1,3-thiazol-2-ylmethyl)urea;
N-{[4-(3,4-dichlorobenzyl)morpholin-2-yl]methyl}-N'-[(2-methyl-1,3-thiazol-4-yl)methyl]urea;
methyl 2-({[({[4-(3,4-dichlorobenzyl)morpholin-2-yl]methyl}amino)carbonyl]-amino}-methyl)-4-methyl-1,3-thiazole-5-carboxylate;
N-[(5-amino-1-phenyl-1H-pyrazol-4-yl)methyl]-N'-{[4-(3,4-dichlorobenzyl)-morpholin-2-yl]methyl}urea;
N-{[4-(3,4-dichlorobenzyl)morpholin-2-yl]methyl}-N'-(1H-pyrrolo[2,3-b]pyridin-3-ylmethyl)urea;
N-{[4-(3,4-dichlorobenzyl)morpholin-2-yl]methyl}-N'-({5-[(dimethylamino)-methyl]thien-2-yl}methyl)urea;
N-{[4-(3,4-dichlorobenzyl)morpholin-2-yl]methyl}-N'-(2-furylmethyl)urea;
N-{[4-(3,4-dichlorobenzyl)morpholin-2-yl]methyl}-N'-[(2-methyl-2H-tetraazol-5-yl)methyl]urea;
N-{[3-(4-chlorophenyl)isoxazol-5-yl]methyl}-N'-{[(2S)-4-(3,4-dichlorobenzyl)-morpholin-2-yl]methyl}urea;
N-{[(2S)-4-(3,4-dichlorobenzyl)morpholin-2-yl]methyl}-N'-[(2-methyl-2H-tetraazol-5-yl)methyl]urea;
N-{[(2S)-4-(3,4-dichlorobenzyl)morpholin-2-yl]methyl}-N'-[(4-methyl-1,3-thiazol-2-yl)methyl]urea;
N-{[(2S)-4-(3,4-dichlorobenzyl)morpholin-2-yl]methyl}-N'-(1,3-thiazol-2-ylmethyl)-urea, and;
N-{[(2S)-4-(3,4-dichlorobenzyl)morpholin-2-yl]methyl}-N'-{[3-(4-methoxyphenyl)-isoxazol-5-yl]methyl}urea.

Examples of the heteroaryl group, R$^1$, include benzofuranyl, benzimidazolyl, imidazolyl, pyridyl, pyrimidinyl, thiazolyl, thiophenyl, furanyl, pyrazinyl, tetrazolyl, triazolyl, oxadiazolyl, isoxazolyl, oxazolyl, and pyrazolyl. When R$^1$ is substituted heteroaryl, suitable substituents include formamido; morpholino C$_{1-6}$alkyl; C$_{3-8}$cycloalkylC$_{1-6}$alkyl; C$_{3-8}$cycloalkylC$_{1-6}$alkylaminocarbonyl; aryl; C$_{1-6}$alkoxycarbonylC$_{1-6}$alkyl; perhaloC$_{1-6}$alkyl; cyanoC$_{1-6}$alkyl; carboxy; R$^5$R$^6$NC(O)—, wherein R$^5$ and R$^6$ may each independently represent hydrogen or C$_{1-6}$alkyl, or R$^5$ and R$^6$ may represent a —(CH$_2$)$_p$— group wherein p is an integer from 3 to 7 so that, together with the nitrogen atom to which they are attached, a 4 to 8-membered heterocyclyl ring is formed which heterocyclyl ring may contain a further heteroatom selected from N and O; C$_{3-8}$cycloalkylaminocarbonyl; amino; C$_{1-6}$alkylsulphonylamino; C$_{1-6}$alkylcarbonyl; C$_{1-6}$alkyl; C$_{1-6}$alkoxycarbonyl; unsubstituted heteroaryl; heteroaryl substituted with C$_{1-6}$alkyl, halo, C$_{1-6}$alkoxy, or hydroxy; halo; C$_{1-6}$alkoxy; nitro; C$_{1-6}$alkylsulphonyl; hydroxy; C$_{1-6}$alkoxyC$_{1-6}$alkyl; C$_{1-6}$alkylthio; (mono- and -di-C$_{1-6}$alkyl)aminoC$_{0-6}$alkyl; and C$_{1-6}$alkylcarbonylamino.

When R$^1$ is substituted by unsubstituted or substituted heteroaryl, examples of said heteroaryl group include isoxazolyl, triazolyl, and oxadiazolyl.

Suitably, R$^1$ is unsubstituted benzimidazolyl, unsubstituted benzofuranyl, unsubstituted or substituted imidazolyl, unsubstituted or substituted pyridyl, unsubstituted or substituted pyrimidinyl, unsubstituted or substituted isoxazolyl, unsubstituted or substituted pyrazinyl, unsubstituted or substituted tetrazolyl, unsubstituted or substituted triazolyl, unsubstituted or substituted pyrazolyl, unsubstituted or substituted furanyl, unsubstituted or substituted thiazolyl, unsubstituted or substituted thiophenyl, unsubstituted or substituted oxadiazolyl, or unsubstituted or substituted oxazolyl When $R^1$ is substituted imidazolyl, suitable substituents include aryl and $C_{1-6}$alkyl.

When $R^1$ is substituted pyridyl, suitable substituents include aminocarbonyl.

When $R^1$ is substituted pyrimidyl, suitable substituents include amino, hydroxy, and $C_{1-6}$alkyl.

When $R^1$ is substituted isoxazolyl, suitable substituents include aryl, $C_{3-8}$cycloalkyl$C_{1-6}$alkylaminocarbonyl, $C_{1-6}$alkyl, $C_{1-6}$alkoxycarbonyl and $R^5R^6NC(O)$— wherein $R^5$ and $R^6$ may each independently represent hydrogen or $C_{1-6}$alkyl.

When $R^1$ is substituted tetrazolyl, suitable substituents include $C_{1-6}$alkoxycarbonyl$C_{1-6}$alkyl, $C_{1-6}$cycloalkyl$C_{1-6}$alkyl, perhalo$C_{1-6}$alkyl, cyano$C_{1-6}$alkyl, and $C_{1-6}$alkyl.

When $R^1$ is substituted triazolyl, suitable substituents include formamido, amino, and $C_{1-6}$alkyl.

When $R^1$ is substituted oxadiazolyl, suitable substituents include perhalo$C_{1-6}$alkyl; $C_{1-6}$alkyl; $C_{1-6}$alkoxycarbonyl; $R^5R^6NC(O)$— wherein $R^5$ and $R^6$ may each independently represent hydrogen or $C_{1-6}$alkyl or $R^5$ and $R^6$ may represent a —$(CH_2)_p$— group wherein p is an integer from 3 to 7 so that, together with the nitrogen atom to which they are attached, a 4 to 8-membered heterocyclyl ring is formed which heterocyclyl ring contains an oxygen atom; $R^5R^6NC(O)$— wherein $R^5$ and $R^6$ may each independently represent hydrogen or $C_{1-6}$alkyl or $R^5$ and $R^6$ may represent a —$(CH_2)_p$— group wherein p is an integer from 3 to 7 so that, together with the nitrogen atom to which they are attached, a 4 to 8-membered heterocyclyl ring is formed; $C_{3-8}$cycloalkylaminocarbonyl; and isoxazolyl substituted with $C_{1-6}$alkyl.

When $R^1$ is substituted pyrazolyl, suitable substituents include $C_{1-6}$alkylcarbonyl and $C_{1-6}$alkyl.

When $R^1$ is substituted furanyl, suitable substituents include unsubstituted or substituted heteroaryl, carboxy; $C_{1-6}$ alkoxycarbonyl; $R^5R^6NC(O)$— wherein $R^5$ and $R^6$ may each independently represent hydrogen or $C_{1-6}$alkyl.

When $R^1$ is substituted thiazolyl, suitable substituents include carboxy; $C_{1-6}$alkoxycarbonyl; $R^5R^6NC(O)$— wherein $R^5$ and $R^6$ may each independently represent hydrogen or $C_{1-6}$alkyl.

When $R^1$ is substituted thiophenyl, suitable substituents include carboxy; $C_{1-6}$ alkoxycarbonyl; and $R^5R^6NC(O)$— wherein $R^5$ and $R^6$ may each independently represent hydrogen or $C_{1-6}$alkyl.

More suitably, $R^1$ is 3-formamido-1,2,4-triazol-5-yl, 5-trifluoromethyl-1,3,4-oxadiazol-2-yl, 5-(morpholin-4-ylmethyl)-1,3,4-oxadiazol-2-yl, 5-(N,N-diethylaminomethyl)-1,3,4-oxadiazol-2-yl, 5-ethylaminomethyl-1,3,4-oxadiazol-2-yl, furan-2-yl, 4-(3-methyl-1,2,4-oxadiazol-5-yl)furan-2-yl, 4-(3-methyl-1,2,4-triazol-5-yl)furan-2-yl, 4-(5-methyl-1,3,4-oxadiazol-2-yl)furan-2-yl, imidazol-2-yl, 1-methylimidazol-5-yl, imidazol-4-yl, 3-(cyclopropylmethylaminocarbonyl)isoxazol-5-yl, 3-(N-pyrrolidinecarbonyl)isoxazol-5-yl, 4-methoxycarbonyloxazol-2-yl, 4-ethylaminocarbonyloxazol-2-yl, 4-cyclopropylmethylaminocarbonyloxazol-2-yl, 4-methylaminocarbonyloxazol-2-yl, 4-(N-pyrrolidinecarbonyl)oxazol-2-yl, 4-iso-propylaminocarbonyloxazol-2-yl, 1-methylcarbonylpyrazol-3-yl, pyridin-4-yl, pyridin-2-yl, pyridin-3-yl, 5-aminocarbonylpyridin-3-yl, 4-aminopyrimidin-5-yl, 4-hydroxy-2-methylpyrimidin-5-yl, 1-methyltetrazol-5-yl, 2-methoxycarbonylmethyltetrazol-5-yl, 1-methoxycarbonylmethyltetrazol-5-yl, 2-cyclopropylmethyltetrazol-5-yl, 1-cyclopropylmethyltetrazol-5-yl, 2-ethyltetrazol-5-yl, 1-ethyltetrazol-5-yl, 2-tert-butyltetrazol-5-yl, 5-trifluoromethyltetrazol-2-yl, 2-cyanomethyltetrazol-5-yl, 1-cyanomethyltetrazol-5-yl, 2-iso-butyltetrazol-5-yl, 1-iso-butyltetrazol-5-yl, 4-(iso-propylaminocarbonyl)thiophen-2-yl, 4-(methylaminocarbonyl)thiophen-2-yl, 4-(ethylaminocarbonyl)thiophen-2-yl, 2-(iso-propyl)tetrazol-5-yl, 1,2,3-triazol-4-yl, 1-methyl-1,2,3-triazol-4-yl, 2-methyl-1,2,3-triazol-4-yl, 1-methyl-1,2,4-triazol-3-yl, 5-methyl-1,2,4-oxadiazol-3-yl, 3-ethoxycarbonyl-1,2,4-oxadiazol-5-yl, 3-methylaminocarbonyl-1,2,4-oxadiazol-5-yl, 3-ethylaminocarbonyl-1,2,4-oxadiazol-5-yl, 5-(5-methylisoxazol-3-yl)-1,2,4-oxadiazol-3-yl, 5-methylaminocarbonyl-1,2,4-oxadiazol-3-yl, 2-methyl-1,3,4-oxadiazol-5-yl, pyrazin-2-yl, 3-methylisoxazol-5-yl, 1,2,4-oxadiazol-3-yl, 1,2,4-oxadiazol-5-yl, 3-(pyrrolidine-N-carbonyl)-1,2,4-oxadiazol-5-yl, 3-(iso-propylaminocarbonyl)-1,2,4-oxadiazol-5-yl, 5-(ethylaminocarbonyl)-1,2,4-oxadiazol-3-yl, 3-(cyclopropylaminocarbonyl)-1,2,4-oxadiazol-5-yl, 3-(iso-propyl(methyl)aminocarbonyl)-1,2,4-oxadiazol-5-yl, 1-iso-propyltetrazol-5-yl, tetrazol-5-yl, 3-amino-1,2,4-triazol-5-yl, 5-methylisoxazol-3-yl, 1-methylpyrazol-4-yl, 2-methylaminocarbonyl-1,3,4-oxadiazol-5-yl, 2-ethylaminocarbonyl-1,3,4-oxadiazol-5-yl, 2-(iso-propylaminocarbonyl)-1,3,4-oxadiazol-5-yl, 2-carboxyfuran-5-yl, 2-(ethoxycarbonyl)furan-5-yl, 2-(methylaminocarbonyl)furan-5-yl, 2-(ethylaminocarbonyl)furan-5-yl, 2-(iso-propylaminocarbonyl)furan-5-yl, 1-methylpyrazol-3-yl, pyrazol-3-yl, 3-methylpyrazol-5-yl, 3-(ethoxycarbonyl)isoxazol-5-yl, 2-methyltetrazol-5-yl, 3-(methylaminocarbonyl)furan-5-yl, 3-(ethylaminocarbonyl)furan-5-yl, 3-(iso-propylaminocarbonyl)furan-5-yl, 3-(methylaminocarbonyl)isoxazol-5-yl, 3-(ethylaminocarbonyl)isoxazol-5-yl, 3-(dimethylaminocarbonyl)isoxazol-5-yl, 3-(iso-propylaminocarbonyl)isoxazol-5-yl, 4-(methylaminocarbonyl)thiazol-2-yl, 4-(ethylaminocarbonyl)thiazol-2-yl, 4-(dimethylaminocarbonyl)thiazol-2-yl, 4-(iso-propylaminocarbonyl)thiazol-2-yl, 4-(ethoxycarbonyl)thiazol-2-yl, 4-carboxythiazol-2-yl, 2-(methylaminocarbonyl)thiophen-5-yl, 2-(ethylaminocarbonyl)thiophen-5-yl, 2-(iso-propylaminocarbonyl)thiophen-5-yl, 2-(methylaminocarbonyl)thiophen-4-yl, 2-(ethylaminocarbonyl)thiophen-4-yl, 2-(iso-propylaminocarbonyl)thiophen-4-yl, 2-(methoxycarbonyl)thiophen-4-yl, 2-carboxythiophen-4-yl, 2-(methoxycarbonyl)thiophen-5-yl, 2-carboxythiophen-5-yl, 3-(ethoxycarbonyl)furan-5-yl, 3-carboxyfuran-5-yl, benzofuran-3-yl, benzimidazol-2-yl, or 3-(1,3,4-oxadiazol-2-yl)furan-5-yl.

Suitably, $R_{na}$ and $R_{nb}$ are both hydrogen.

Suitably, n is 0, 1, or 2.

Preferably, n is 1 or 2.

Suitably, $R^3$ and $R^4$ are both hydrogen.

When $R^2$ is aryl, examples include phenyl.

When $R^2$ is substituted aryl, suitable substituents include cyano, perhalo$C_{1-6}$alkyl, amido, halo, $C_{1-6}$alkyl, $C_{1-6}$alkoxycarbonyl, mono- and di-($C_{1-6}$alkyl)aminocarbonyl, $C_{1-6}$alkoxy, nitro, $C_{1-6}$alkylsulphonyl, hydroxy, $C_{1-6}$alkoxy$C_{1-6}$alkyl, $C_{1-6}$alkylthio, mono- and -di-($C_{1-6}$alkyl)amino, and $C_{1-6}$alkylcarbonylamino.

When $R^2$ is heteroaryl, examples include thiophenyl.

When $R^2$ is substituted heteroaryl, suitable substituents include cyano, perhalo$C_{1-6}$alkyl, amido, halo, $C_{1-6}$alkyl, $C_{1-6}$alkoxycarbonyl, mono- and di-($C_{1-6}$alkyl)aminocarbonyl, $C_{1-6}$alkoxy, nitro, $C_{1-6}$alkylsulphonyl, hydroxy, $C_{1-6}$alkoxy$C_{1-6}$alkyl, $C_{1-6}$alkylthio, mono- and -di-($C_{1-6}$alkyl)amino, and $C_{1-6}$alkylcarbonylamino. Suitably, $R^2$ is unsubstituted or substituted phenyl or unsubstituted or substituted thiophenyl.

When $R^2$ is substituted phenyl suitable substituents include halo especially chloro or fluoro.

When $R^2$ is substituted thiophenyl suitable substituents include halo especially chloro.

More suitably, $R^2$ is phenyl substituted with chloro or fluoro, or $R^2$ is thiophenyl substituted with chloro.

Preferably, $R^2$ is 3-chloro-4-fluorophenyl, 3,4-dichlorophenyl, 3,4-difluorophenyl, 3-chlorophenyl, 2-chlorothiophen-5-yl, or 4-fluorophenyl.

Suitably, $R^7$ is hydrogen or methyl.
More suitably, $R^7$ is hydrogen.
Suitably, $R^8$ is hydrogen or methyl
More suitably, $R^8$ is hydrogen.

There exists a preferred subgroup of compounds of formula (I), being of formula (I')

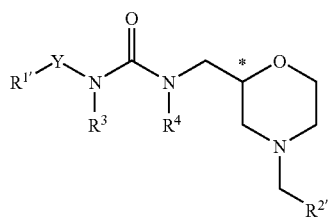

(I')

wherein;
$R^{1'}$ is unsubstituted or substituted heteroaryl, and;
$R^{2'}$ is phenyl substituted by halo.

Suitably, $R^{1'}$ is unsubstituted or substituted furanyl, unsubstituted or substituted pyrazolyl, unsubstituted or substituted tetrazolyl, unsubstituted or substituted triazolyl, unsubstituted or substituted oxadiazolyl, unsubstituted or substituted pyrazinyl, unsubstituted or substituted thiazolyl, unsubstituted or substituted thiophenyl, or unsubstituted or substituted isoxazolyl.

Preferably, $R^{1'}$ is 1-methyltetrazol-5-yl, 2-methoxycarbonylmethyltetrazol-5-yl, 1-methoxycarbonylmethyltetrazol-5-yl, 2-cyclopropylmethyltetrazol-5-yl, 1-cyclopropylmethyltetrazol-5-yl, 2-ethyltetrazol-5-yl, 1-ethyltetrazol-5-yl, 2-tert-butyltetrazol-5-yl, 5-trifluoromethyltetrazol-2-yl, 2-cyanomethyltetrazol-5-yl, 1-cyanomethyltetrazol-5-yl, 2-iso-butyltetrazol-5-yl, 1-iso-butyltetrazol-5-yl, 4-(iso-propylaminocarbonyl)thiophen-2-yl, 4-(methylaminocarbonyl)thiophen-2-yl, 4-(ethylaminocarbonyl)thiophen-2-yl, 2-(iso-propyl)tetrazol-5-yl, 1,2,3-triazol-4-yl, 1-methyl-1,2,3-triazol-4-yl, 2-methyl-1,2,3-triazol-4-yl, 1-methyl-1,2,4-triazol-3-yl, 5-methyl-1,2,4-oxadiazol-3-yl, 3-ethoxycarbonyl-1,2,4-oxadiazol-5-yl, 3-methylaminocarbonyl-1,2,4-oxadiazol-5-yl, 3-ethylaminocarbonyl-1,2,4-oxadiazol-5-yl, 5-(5-methylisoxazol-3-yl)-1,2,4-oxadiazol-3-yl, 5-methylaminocarbonyl-1,2,4-oxadiazol-3-yl, 2-methyl-1,3,4-oxadiazol-5-yl, pyrazin-2-yl, 3-methylisoxazol-5-yl, 1,2,4-oxadiazol-3-yl, 1,2,4-oxadiazol-5-yl, 3-(pyrrolidine-N-carbonyl)-1,2,4-oxadiazol-5-yl, 3-(iso-propylaminocarbonyl)-1,2,4-oxadiazol-5-yl, 5-(ethylaminocarbonyl)-1,2,4-oxadiazol-3-yl, 3-(cyclopropylaminocarbonyl)-1,2,4-oxadiazol-5-yl, 3-(iso-propyl(methyl)aminocarbonyl)-1,2,4-oxadiazol-5-yl, 1-iso-propyltetrazol-5-yl, tetrazol-5-yl, 2-amino-1,3,4-triazol-5-yl, 5-methylisoxazol-3-yl, 1-methylpyrazol-4-yl, 2-methylaminocarbonyl-1,3,4-oxadiazol-5-yl, 2-ethylaminocarbonyl-1,3,4-oxadiazol-5-yl, 2-(iso-propylaminocarbonyl)-1,3,4-oxadiazol-5-yl, 2-carboxyfuran-5-yl, 2-(ethoxycarbonyl)furan-5-yl, 2-(methoxycarbonyl)furan-5-yl, 2-(ethylaminocarbonyl)furan-5-yl, 2-(iso-propylaminocarbonyl)furan-5-yl, 1-methylpyrazol-3-yl, pyrazol-3-yl, 3-methylpyrazol-5-yl, 3-(ethoxycarbonyl)isoxazol-5-yl, 2-methyltetrazol-5-yl, 3-(methylaminocarbonyl)furan-5-yl, 3-(ethylaminocarbonyl)furan-5-yl, 3-(iso-propylaminocarbonyl)furan-5-yl, 3-(methylaminocarbonyl)isoxazol-5-yl, 3-(ethylaminocarbonyl)isoxazol-5-yl, 3-(dimethylaminocarbonyl)isoxazol-5-yl, 3-(iso-propylaminocarbonyl)isoxazol-5-yl, 4-(methylaminocarbonyl)thiazol-2-yl, 4-(ethylaminocarbonyl)thiazol-2-yl, 4-(dimethylaminocarbonyl)thiazol-2-yl, 4-(iso-propylaminocarbonyl)thiazol-2-yl, 4-(ethoxycarbonyl)thiazol-2-yl, 4-carboxythiazol-2-yl, 2-(methylaminocarbonyl)thiophen-5-yl, 2-(ethylaminocarbonyl)thiophen-5-yl, 2-(isopropylaminocarbonyl)thiophen-5-yl, 2-(methylaminocarbonyl)thiophen-4-yl, 2-(ethylaminocarbonyl)thiophen-4-yl, 2-(iso-propylaminocarbonyl)thiophen-4-yl, 2-(methoxycarbonyl)thiophen-4-yl, 2-carboxythiophen-4-yl, 2-(methoxycarbonyl)thiophen-5-yl, 2-carboxythiophen-5-yl, 3-(ethoxycarbonyl)furan-5-yl, or 3-carboxyfuran-5-yl.

Suitably, $R^{2'}$ is phenyl substituted with chloro or fluoro or thiophenyl substituted with chloro.

Preferably, $R^{2'}$ is 2-chlorothiophen-5-yl, 3,4-dichlorophenyl, 3,4-difluorophenyl, 3-chlorophenyl, 4-fluorophenyl, or 3-chloro-4-fluorophenyl.

Suitably, the stereochemistry at the position marked "*" is (S).

Accordingly, there is provided a compound of formula (I') or a salt or solvate thereof.

There exists a preferred subgroup of compounds of formula (I) being of formula (Ia)

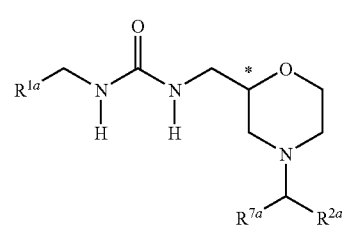

(Ia)

wherein;
$R^{1a}$ is unsubstituted or substituted C-linked tetrazolyl;
$R^{2a}$ is substituted phenyl, and;
$R^{7a}$ is hydrogen or $C_{1-6}$alkyl.

Suitable substituents for C-linked tetrazolyl are $C_{1-6}$alkyl, $C_{1-6}$alkoxycarbonyl$C_{1-6}$alkyl, $C_3$cycloalkyl$C_{1-6}$alkyl, or cyano$C_{1-6}$alkyl.

Suitably, $R^{1a}$ is 2-iso-propyltetrazol-5-yl, 1-iso-propyltetrazol-5-yl, tetrazol-5-yl, 2-methyltetrazol-5-yl, 1-methyltetrazol-5-yl, 2-methoxycarbonylmethyltetrazol-5-yl, 1-methoxycarbonylmethyltetrazol-5-yl, 2-cyclopropylmethyltetrazol-5-yl, 1-cyclopropylmethyltetrazol-5-yl, 2-ethyltetrazol-5-yl, 1-ethyltetrazol-5-yl, 2-tert-butyltetrazol-5-yl, 2-cyanomethyltetrazol-5-yl, 1-cyanomethyltetrazol-5-yl, 2-iso-butyltetrazol-5-yl, or 1-iso-butyltetrazol-5-yl.

Suitable substituents for phenyl are halo, suitably fluoro and chloro.

Suitably, $R^{2a}$ is 3,4-dichlorophenyl, 3-chloro-4-fluorophenyl, or 3,4-difluorophenyl.

Suitably, $R^{7a}$ is hydrogen or methyl.

Suitably, the stereochemistry at the position marked "*" is S or RS.

Accordingly, there is provided a compound of formula (Ia) or a salt or solvate thereof.

There exists a preferred subgroup of compounds of formula (I) being of formula (Ib)

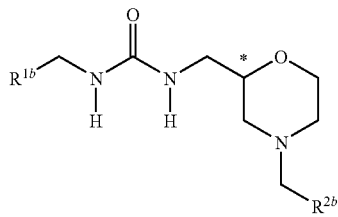

(Ib)

wherein;
$R^{1b}$ is unsubstituted or substituted triazolyl, and;
$R^{2b}$ is substituted phenyl.

Suitable substituents for triazolyl are $C_{1-6}$alkyl, amino, and formamido.

Suitably, $R^{1b}$ is 1,2,3-triazol-4-yl, 1-methyl-1,2,3-triazol-4-yl, 2-methyl-1,2,3-triazol-4-yl, 1-methyl-1,2,4-triazol-3-yl, 3-amino-1,2,4-triazol-5-yl, or 3-formamido-1,2,4-triazol-5-yl.

Suitable substituents for phenyl are halo, suitably chloro.
Suitably, $R^{2a}$ is 3,4-dichlorophenyl.
Suitably, the stereochemistry at the position marked "*" is S.

Accordingly, there is provided a compound of formula (Ib) or a salt or solvate thereof.

There exists a preferred subgroup of compounds of formula (I) being of formula (Ic)

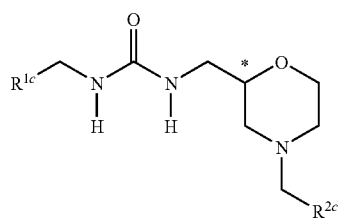

(Ic)

wherein;
$R^{1c}$ is unsubstituted or substituted oxadiazolyl, and;
$R^{2c}$ is substituted phenyl.

Suitable substituents for oxadiazolyl are $C_{1-6}$alkyl; $C_{1-6}$alkoxycarbonyl; (mono- and di-$C_{1-6}$alkyl)aminocarbonyl; substituted isoxazolyl wherein suitable substituents are $C_{1-6}$alkyl, preferably methyl; heterocyclylcarbonyl, suitably pyrrolidinylcarbonyl; heterocyclyl$C_{1-6}$alkyl, suitably morpholin-4-ylmethyl; and $C_{3-8}$cycloalkylaminocarbonyl.

Suitably, $R^{1c}$ is 5-methyl-1,2,4-oxadiazol-3-yl, 3-ethoxycarbonyl-1,2,4-oxadiazol-5-yl, 3-methylaminocarbonyl-1,2,4-oxadiazol-5-yl, 3-ethylaminocarbonyl-1,2,4-oxadiazol-5-yl, 5-(5-methylisoxaxol-3-yl)-1,2,4-oxadiazol-3-yl, 5-methylaminocarbonyl-1,2,4-oxadiazol-3-yl, 5-ethylaminocarbonyl-1,2,4-oxadiazol-3-yl, 2-methyl-1,3,4-oxadiazol-5-yl, 1,2,4-oxadiazol-5-yl, 3-(pyrrolidin-1-ylcarbonyl)-1,2,4-oxadiazol-5-yl, 3-iso-propylaminocarbonyl-1,2,4-oxadiazol-5-yl, 3-cyclopropylaminocarbonyl-1,2,4-oxadiazol-5-yl, 3-(N-methyl-N-iso-propylaminocarbonyl)-1,2,4-oxadiazol-5-yl, 2-ethylaminocarbonyl-1,3,4-oxadiazol-5-yl, 2-iso-propyl-1,3,4-oxadiazol-5-yl, 2-methyl-1,3,4-oxadiazol-5-methylene, 2-methylaminocarbonyl-1,3,4-oxadizol-5-yl, 2-trifluoromethyl-1,3,4-oxadiazol-5-yl, 2-(morpholin-4-ylmethyl)-1,3,4-oxadiazol-5-yl, 2-(N,N-diethylaminomethyl)-1,3,4-oxadiazol-5-yl, or 2-ethylaminomethyl-1,3,4-oxadiazol-5-yl.

Suitable substituents for phenyl are halo, suitably fluoro and chloro.

Suitably, $R^{2c}$ is 3,4-dichlorophenyl, 3,4-difluorophenyl, 3-chlorophenyl, 4-fluorophenyl, or 3-chloro-4-fluorophenyl.

Suitably, the stereochemistry at the position marked "*" is S.

Accordingly, there is provided a compound of formula (Ic) or a salt or solvate thereof.

There exists a preferred subgroup of compounds of formula (I) being of formula (Id)

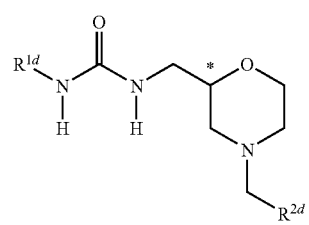

(Id)

wherein;
$R^{1d}$ is unsubstituted pyrazinyl or unsubstituted or substituted pyrazolyl, unsubstituted or substituted imidazolyl, unsubstituted or substituted pyridinyl, substituted pyrimidinyl wherein said pyrazinyl, pyrazolyl, imidazolyl, pyridinyl, and pyrimidinyl moieties may optionally be linked to the residue of the compound of formula (Id) by a methylene or ethylene link, and;

$R^{2d}$ is substituted phenyl.

Suitable substituents for pyrazolyl are $C_{1-6}$alkyl.

Suitably, $R^{1d}$ is pyrazin-2-ylmethylene, 1-methylpyrazol-4-ylmethylene, 1-methylpyrazol-3-ylmethylene, pyrazol-3-ylmethylene, 3-methylpyrazol-5-ylmethylene, imidazol-2-ylmethylene, 1-methylimidazol-5-ylmethylene, imidazol-4-ethylene, 1-methylcarbonylpyrazol-3-ylmethylene, pyridine-4-ethylene, pyridine-2-ethylene, pyridine-3-ethylene, 3-aminocarbonylpyridin-5-ylmethylene, 4-aminopyrimidine-5-ylmethylene, 2-methyl-4-hydroxypyrimidin-5-ylmethylene, pyridin-4-yl, pyridin-2-yl, pyridin-3-yl, pyridine-2-ylmethylene, or pyridin-3-ylmethylene.

Suitable substituents for phenyl are halo, suitably chloro.
Suitably, $R^{2d}$ is 3,4-dichlorophenyl.
Suitably, the stereochemistry at the position marked "*" is S or RS.

Accordingly, there is provided a compound of formula (Id) or a salt or solvate thereof.

There exists a preferred subgroup of compounds of formula (I) being of formula (Ie)

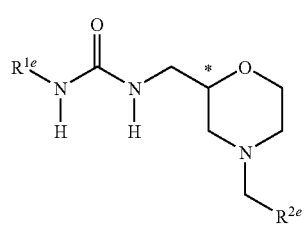

(Ie)

wherein;

R$^{1e}$ is substituted isoxazolyl or substituted thiazolyl, or substituted oxazolyl, wherein said isoxazolyl, thiazolyl and oxazolyl groups may optionally be linked to the residue of the compound of formula (Ie) by a methylene link, and;

R$^{2e}$ is substituted phenyl or substituted thiophenyl.

Suitable substituents for isoxazolyl are heterocyclylcarbonyl, phenyl, $C_{3-8}$cycloalkyl$C_{1-6}$alkylaminocarbonyl, $C_{1-6}$alkyl, $C_{1-6}$alkoxycarbonyl, and (mono- and di-$C_{1-6}$alkyl)aminocarbonyl.

Suitable substituents for thiazolyl are carboxy, $C_{1-6}$alkoxycarbonyl, and (mono- and di-$C_{1-6}$alkyl)aminocarbonyl.

Suitable substituents for oxazolyl are heterocyclylcarbonyl, $C_{1-6}$alkoxycarbonyl, (mono- and di-$C_{1-16}$alkyl)aminocarbonyl, and $C_{3-8}$cycloalkyl$C_{1-6}$alkylaminocarbonyl.

Suitably, R$^{1e}$ is 3-methylisoxazol-5-ylmethylene, 5-methylisoxazol-3-ylmethylene, 3-ethoxycarbonylisoxazol-5-ylmethylene, 3-methylaminocarbonylisoxazol-5-ylmethylene, 3-ethylaminocarbonylisoxazol-5-ylmethylene, 3-(N,N-dimethylamino)carbonylisoxazol-5-ylmethylene, 3-iso-propylaminocarbonylisoxazol-5-ylmethylene, 4-methylaminocarbonylthiazol-2-ylmethylene, 4-ethylaminocarbonylthiazol-2-ylmethylene, 4-(N,N-dimethylamino)carbonylthiazol-2-ylmethylene, 4-iso-propylaminocarbonylthiazol-2-ylmethylene, 4-ethoxycarbonylthiazol-2-ylmethylene, 4-carboxythiazol-2-ylmethylene, 3-cyclopropylmethylaminocarbonylisoxazol-5-ylmethylene, 3-(N-pyrrolidinylcarbonyl)isoxazol-5-ylmethylene, 4-methoxycarbonyloxazol-2-ylmethylene, 4-ethylaminocarbonyloxazol-2-ylmethylene, 4-cyclopropylmethylaminocarbonyloxazol-2-ylmethylene, 4-methylaminocarbonyloxazol-2-ylmethylene, 4-(N-pyrrolidinylcarbonyl)oxazol-2-ylmethylene, 4-iso-propylaminocarbonyloxazol-2-ylmethylene, 3,5-dimethylisoxazol-4-yl, or 5-methyl-3-phenyloxazol-4-ylmethylene.

Suitable substituents for phenyl are chloro and fluoro.

Suitable substituents for thiophenyl is chloro.

Suitably, R$^{2e}$ is 3,4-dichlorophenyl, 3,4-difluorophenyl, 3-chloro-4-fluorophenyl, or 2-chlorothiophen-5-yl.

Suitably, the stereochemistry at the position marked "*" is RS or S.

Accordingly, there is provided a compound of formula (Ie) or a salt or solvate thereof.

There exists a preferred subgroup of compounds of formula (I) being of formula (If)

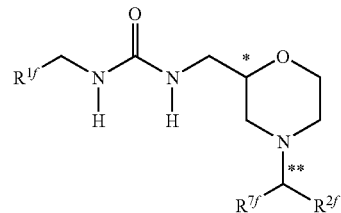

(If)

wherein;

R$^{1f}$ is unsubstituted or substituted furanyl or substituted thiophenyl;

R$^{2f}$ is substituted phenyl, and;

R$^{7f}$ is hydrogen or $C_{1-6}$alkyl.

Suitable substituents for furanyl are unsubstituted heteroaryl suitably ozadiazolyl, heteroaryl substituted with $C_{1-6}$alkyl, suitably oxadiazolyl or triazolyl substituted with methyl; carboxy; $C_{1-6}$alkoxycarbonyl; and (mono- and di-$C_{1-6}$alkyl)aminocarbonyl.

Suitable substituents for thiophenyl are (mono- and di-$C_{1-6}$alkyl)aminocarbonyl, $C_{1-6}$alkoxycarbonyl, and carboxy.

Suitably, R$^{1f}$ is 3-(1,3,4-oxadiazol-2-yl)furan-5-yl, furan-2-ylmethylene, 4-(3-methyl-1,2,4-oxadiazol-5-yl)furan-2-yl, 4-(3-methyl-1,2,4-triazol-5-yl)furan-2-yl, 4-(2-methyl-1,3,4-oxadiazol-5-yl)furan-2-yl, 2-carboxyfuran-5-yl, 2-ethoxycarbonylfuran-5-yl, 2-methylaminocarbonylfuran-5-yl, 2-ethylaminocarbonylfuran-5-yl, 2-iso-propylaminocarbonylfuran-5-yl, 3-methylaminocarbonylfuran-5-yl, 3-ethylaminocarbonylfuran-5-yl, 3-iso-propylaminocarbonylfuran-5-yl, 2-methylaminocarbonylthiophen-5-yl, 2-ethylaminocarbonylthiophen-5-yl, 2-iso-propylaminocarbonylthiophen-5-yl, 2-methylaminocarbonylthiophen-4-yl, 2-ethylaminocarbonylthiophen-4-yl, 2-iso-propylaminocarbonylthiophen-4-yl, 2-methoxycarbonylthiophen-4-yl, 2-carboxythiophen-4-yl, 2-methoxycarbonylthiophen-5-yl, 2-carboxythiophen-5-yl, 3-ethoxycarbonylfuran-5-yl, 3-carboxyfuran-5-yl, 3-iso-propylaminocarbonylthiophen-5-yl, 3-ethylaminocarbonylthiophen-5-yl, or 3-methylaminocarbonylthiophen-5-yl.

Suitable substituents for phenyl are chloro and fluoro.

Suitably, R$^{2f}$ is 3,4-dichlorophenyl or 3,4-difluorophenyl.

Suitably, R$^{7f}$ is hydrogen or methyl.

Suitably, the stereochemistry at the position marked "*" is RS or S.

Suitably, the stereochemistry at the position marked "**" is RS, R, or S.

Accordingly, there is provided a compound of formula (If) or a salt or solvate thereof.

There exists a preferred subgroup of compounds of formula (I) being of formula (Ig)

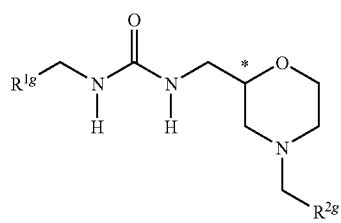

(Ig)

wherein;

R$^{1g}$ is unsubstituted or substituted N-linked tetrazolyl or unsubstituted or substituted N-linked imidazolyl, and;

R$^{2g}$ is substituted phenyl.

A suitable substituent for N-linked tetrazolyl is perhalo C$_{1-6}$alkyl.

A suitable substituent for N-linked imidazolyl is phenyl.

Suitably, R$^{1g}$ is 5-trifluoromethyltetrazol-2-yl, 2-phenylimidazol-1-ylmethylene, or imidazol-1-ylmethylene.

Suitable substituents for phenyl are halo, suitably fluoro and chloro.

Suitably, R$^{2g}$ is 3,4-difluorophenyl or 3,4-dichlorophenyl.

Suitably, the stereochemistry at the position marked "*" is S or RS.

Accordingly, there is provided a compound of formula (Ig) or a salt or solvate thereof.

There exists a preferred subgroup of compounds of formula (I) being of formula (Ih)

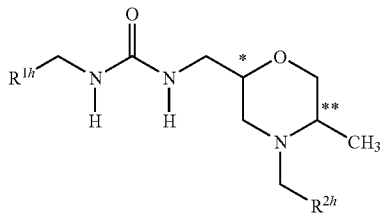

(Ih)

wherein;

R$^{1h}$ is substituted furanyl, and;

R$^{2h}$ is substituted phenyl.

A suitable substituent for furanyl is C$_{1-6}$alkylaminocarbonyl.

Suitably, R$^{1h}$ is 4-methylaminocarbonylfuran-2-yl.

A suitable substituent for phenyl is chloro.

Suitably, R$^{2h}$ is 3,4-dichlorophenyl.

Suitably, the stereochemistry at the position marked "*" is S or R.

Suitably, the stereochemistry at the position marked is R.

Accordingly, there is provided a compound of formula (Ih) or a salt or solvate thereof.

There exists a preferred subgroup of compounds of formula (I) being of formula (Ii)

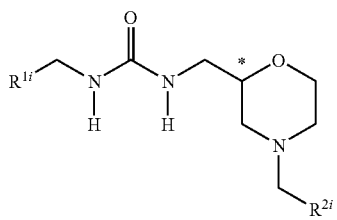

(Ii)

wherein;

R$^{1i}$ is unsubstituted benzofuranyl or unsubstituted benzimidazolyl, and;

R$^{2g}$ is substituted phenyl.

Suitably, R$^{1i}$ is unsubstituted benzofyranyl or unsubstituted benzimidazolyl.

A suitable substituent for phenyl is chloro.

Suitably, R$^{2i}$ is 3,4-dichlorophenyl.

Suitably, the stereochemistry at the position marked "*" is RS.

Accordingly, there is provided a compound of formula (II) or a salt or solvate thereof.

A group of compounds of formula (I) which may be mentioned consists of compounds of formula (I"):

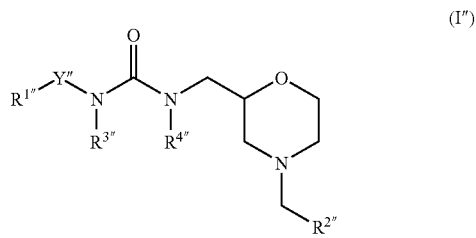

(I")

wherein:

R$^{1"}$ represents substituted or unsubstituted heteroaryl;

Y" represents —(CR$_{na"}$R$_{nb"}$)$_{n"}$—;

R$_{na"}$ and R$_{nb"}$ are each independently hydrogen or C$_{1-6}$alkyl;

n" is an integer from 1 to 5;

R$^{2"}$ represents unsubstituted or substituted aryl or unsubstituted or substituted heteroaryl;

R$^3$ and R$^4$ each independently represent hydrogen or C$_{1-6}$alkyl; and salts and solvates thereof;

with the proviso that the following compounds are excluded;

N-{[4-(3,4-dichlorobenzyl)morpholin-2-yl]methyl}-N'-(pyridin-3-ylmethyl)urea;

N-{[4-(3,4-dichlorobenzyl)morpholin-2-yl]methyl}-N'-[(6-methoxypyridin-3-yl)methyl]urea;

5-({[({[4-(3,4-dichlorobenzyl)morpholin-2-yl]methyl}amino)carbonyl]-amino}methyl)nicotinamide;

N-{[4-(3,4-dichlorobenzyl)morpholin-2-yl]methyl}-N'-(1H-indol-5-ylmethyl)urea;

N-{[4-(3,4-dichlorobenzyl)morpholin-2-yl]methyl}-N'-(1H-indol-4-ylmethyl)urea;

N-{[4-(3,4-dichlorobenzyl)morpholin-2-yl]methyl}-N'-[(5-methylisoxazol-3-yl)methyl]urea;

N-{[4-(3,4-dichlorobenzyl)morpholin-2-yl]methyl}-N'-(thien-2-ylmethyl)urea;

N-{[4-(3,4-dichlorobenzyl)morpholin-2-yl]methyl}-N'-(2-thien-2-ylethyl)urea;

N-{[4-(3,4-dichlorobenzyl)morpholin-2-yl]methyl}-N'-({5-[(dimethylamino)methyl]-2-furyl}methyl)urea;

N-{[4-(3,4-dichlorobenzyl)morpholin-2-yl]methyl}-N'-[(3-methoxyisothiazol-5-yl)methyl]urea;

N-{[4-(3,4-dichlorobenzyl)morpholin-2-yl]methyl}-N'-[(4-methyl-1,3-thiazol-2-yl)methyl]urea;

N-{[4-(3,4-dichlorobenzyl)morpholin-2-yl]methyl}-N'-(1,3-thiazol-2-ylmethyl)urea;

N-{[4-(3,4-dichlorobenzyl)morpholin-2-yl]methyl}-N'-[(2-methyl-1,3-thiazol-4-yl)methyl]urea;

methyl 2-({[({[4-(3,4-dichlorobenzyl)morpholin-2-yl]methyl}amino)carbonyl]-amino}-methyl)-4-methyl-1,3-thiazole-5-carboxylate;

N-[(5-amino-1-phenyl-1H-pyrazol-4-yl)methyl]-N'-{[4-(3,4-dichlorobenzyl)-morpholin-2-yl]methyl}urea;

N-{[4-(3,4-dichlorobenzyl)morpholin-2-yl]methyl}-N'-(1H-pyrrolo[2,3-b]pyridin-3-ylmethyl)urea;

N-{[4-(3,4-dichlorobenzyl)morpholin-2-yl]methyl}-N'-({5-[(dimethylamino)-methyl]thien-2-yl}methyl)urea;

N-{[4-(3,4-dichlorobenzyl)morpholin-2-yl]methyl}-N'-(2-furylmethyl)urea;
N-{[4-(3,4-dichlorobenzyl)morpholin-2-yl]methyl}-N'-[(2-methyl-2H-tetraazol-5-yl)methyl]urea;
N-{[3-(4-chlorophenyl)isoxazol-5-yl]methyl}-N'-{[(2S)-4-(3,4-dichlorobenzyl)-morpholin-2-yl]methyl}urea;
N-{[(2S)-4-(3,4-dichlorobenzyl)morpholin-2-yl]methyl}-N'-[(2-methyl-2H-tetraazol-5-yl)methyl]urea;
N-{[(2S)-4-(3,4-dichlorobenzyl)morpholin-2-yl]methyl}-N'-[(4-methyl-1,3-thiazol-2-yl)methyl]urea;
N-{[(2S)-4-(3,4-dichlorobenzyl)morpholin-2-yl]methyl}-N'-(1,3-thiazol-2-ylmethyl)-urea, and;
N-{[(2S)-4-(3,4-dichlorobenzyl)morpholin-2-yl]methyl}-N'-{[3-(4-methoxyphenyl)-isoxazol-5-yl]methyl}urea.

Suitable compounds of the invention are Examples 1, 2, 3, 4, 6, 7, 8, 9, 10, 11, 12, 13, 14, 15, 16, 17, 18, 19, 20, 21, 23, 24, 25, 26, 27, 28, 29, 32, 33, 34, 35, 36, 38, 40, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 74, 75, 76, 77, 78, 79, 93, 95, 97, 98, 99, 101, 104, 106, 108, 109, 110, 111, 112, 113, 114, 115, 116, 117, 118, 120, 139, 141, 142, 146, 150, 153, 154, 155, 156, 157, 158, 159, 160, 161, 162, 163, 164, 169, 170, 171, 181, and 182.

Preferred compounds of the invention are Examples 1, 2, 7, 8, 9, 10, 11, 12, 16, 18, 19, 21, 24, 36, 38, 43, 44, 45, 49, 50, 55, 56, 57, 58, 59, 60, 61, 62, 63, 66, 67, 74, 75, 76, 77, 78, 79, 97, 99, 101, 108, 109, 110, 111, 112, 113, 114, 115, 116, 117, 118, 153, 154, 155, 157, 159, 160, 161, 163, 164, 169, 170, 171, and 182.

More preferred compounds of the invention are Examples 2, 10, 12, 16, 19, 21, 24, 38, 50, 55, 56, 57, 60, 61, 62, 63, 74, 75, 97, 108, 110, 111, 112, 113, 114, 115, 116, 153, 155, 159, 164, 169, 170, 171, and 182.

Especially preferred compounds of the invention are Examples 2, 12, 16, 19, 38, 50, 55, 56, 57, 60, 61, 74, 75, 97, 111, 113, 114, 115, 116, 159, 170, and 182.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, pamoates, methanesulphonates, formates or trifluoroacetates.

Examples of suitable salts are physiologically acceptable salts.

Examples of solvates include hydrates.

Certain of the compounds of formula (I) may contain chiral atoms and/or multiple bonds, and hence may exist in one or more stereoisomeric forms. The present invention encompasses all of the stereoisomers of the compounds of formula (I), including geometric isomers and optical isomers, whether as individual stereoisomers or as mixtures thereof including racemic modifications.

Generally it is preferred that a compound of formula (I) is in the form of a single enantiomer or diastereoisomer.

Certain of the compounds of formula (I) may exist in one of several tautomeric forms. It will be understood that the present invention encompasses all of the tautomers of the compounds of formula (I) whether as individual tautomers or as mixtures thereof.

References to 'aryl' refer to monocyclic and bicyclic carbocyclic aromatic rings, for example naphthyl and phenyl, especially phenyl.

Suitable substituents for any aryl group include 1 to 5, suitably 1 to 3, substituents selected from the list consisting of cyano, perhaloalkyl, amido, halo, alkyl, alkoxycarbonyl, mono- and di-(alkyl)aminocarbonyl, alkoxy, nitro, alkylsulphonyl, hydroxy, alkoxyalkyl, alkylthio, mono- and -di-(alkyl)amino, and alkylcarbonylamino.

References to 'heteroaryl' refer to monocyclic and bicyclic heterocyclic aromatic rings containing 1-4 heteroatoms selected from nitrogen, oxygen and sulphur. Examples of heterocyclic aromatic rings include oxazolyl, benzofuranyl, benzimidazolyl, imidazolyl, pyridyl, pyrimidinyl, thiazolyl, thiophenyl, furanyl, pyrazinyl, tetrazolyl, triazolyl, oxadiazolyl, isoxazolyl, and pyrazolyl.

Suitable substituents for any heteroaryl group include 1 to 5, suitably 1 to 3, substituents selected from the list consisting of aminocarbonyl; formamido; morpholinoalkyl; cycloalkylalkyl; cycloalkylalkylaminocarbonyl; aryl; alkoxycarbonylalkyl; perhaloalkyl; cyanoalkyl; carboxy; $R^5R^6NC(O)$—, wherein $R^5$ and $R^6$ may each independently represent hydrogen or $C_{1-6}$alkyl, or $R^5$ and $R^6$ may represent a —$(CH_2)_p$— group wherein p is an integer from 3 to 7 so that, together with the nitrogen atom to which they are attached, a 4 to 8-membered heterocyclyl ring is formed which heterocyclyl ring may contain a further heteroatom selected from N and O; cycloalkylaminocarbonyl; amino; alkylsulphonylamino; alkylcarbonyl; alkyl; alkoxycarbonyl; unsubstituted heteroaryl; heteroaryl substituted with alkyl, halo, alkoxy, or hydroxy; halo; alkoxy; nitro; alkylsulphonyl; hydroxy; alkoxyalkyl; alkylthio; (mono- and -di-alkyl)amino $C_{0-6}$alkyl; and alkylcarbonylamino.

References to 'alkyl' include references to both straight chain and branched chain aliphatic isomers of the corresponding alkyl, suitably containing up to six carbon atoms.

References to 'cycloalkyl' include saturated alicyclic rings suitably containing 3-8 carbon atoms. Suitable substituents for any cycloalkyl group include alkyl, halo, and hydroxy.

References to 'heterocyclyl' refer to monocyclic heterocyclic aliphatic rings containing 2 to 6, suitably 3 to 5, carbon atoms, and 1 to 3, heteroatoms selected from nitrogen, oxygen, and sulphur. Examples of heterocyclic rings include piperidinyl, morpholinyl, and pyrrolidinyl. Suitable substituents for any heterocyclyl group include cycloalkylcarbonyl, aminocarbonyl, alkylsulphonylamino, alkylcarbonyl, cycloalkylaminocarbonyl, alkyl, alkoxycarbonyl, alkylaminocarbonyl, halo, alkoxy, nitro, alkylsulphonyl, hydroxy, alkoxyalkyl, alkylthio, mono- and di-(alkyl)amino, and alkylcarbonylamino.

References to 'halogen' or 'halo' refer to iodo, bromo, chloro or fluoro, especially fluoro and chloro.

The compounds of formula (I) and salts and solvates thereof may be prepared by the methodology described hereinafter, constituting a further aspect of this invention.

Accordingly, there is provided a process for the preparation of a compound of formula (I) which process comprises the reaction of a compound of formula (II) with a compound of formula (III);

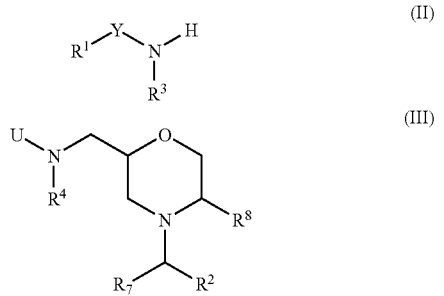

(II)

(III)

wherein;

$R^1$, Y, $R^3$, $R^4$, $R^7$, $R^8$, and $R^2$ are as hereinbefore defined for formula (I) and U is a urea-forming group;

and thereafter, if required, carrying out one or more of the following optional steps:

(i) converting a compound of formula (I) to a further compound of formula (I);

(ii) removing any necessary protecting group;

(iii) preparing a salt or solvate of the compound so formed.

A urea-forming group is a group which is derived from a reagent which introduces a carbonyl group and a leaving group to an amino compound. Examples of urea-forming groups are imidazolylcarbonyl and chlorocarbonyl, and, when $R^4$ is hydrogen, then 4-nitrophenoxycarbonyl may be used. The reagents from which they are derived are 1,1'-carbonyldiimidazole, phosgene, and 4-nitrophenylchloroformate respectively. A suitable urea-forming group is 4-nitrophenoxycarbonyl.

Typically, the compound of formula (II) and the compound of formula (III) in a suitable solvent, such as an organic solvent, e.g. N,N-dimethylformamide are treated with a suitable base, such as a tertiary amine, e.g. N,N-diisopropylethylamine, at ambient temperature, such as 18-25° C.

There is further provided a process for the preparation of a compound of formula (I) wherein $R^7$ represents hydrogen, which process comprises the reaction of a compound of formula (IV) wherein $R^7$ is hydrogen with a compound of formula $R^1$—Y—NCO wherein $R^1$ and Y are as hereinbefore defined and thereafter, if required, carrying out one or more of the following optional steps:

(i) converting a compound of formula (I) to a further compound of formula (I);

(ii) removing any necessary protecting group;

(iii) preparing a salt or solvate of the compound so formed.

Typically, the compound of formula (IV) wherein $R^7$ is hydrogen is reacted with the compound of formula $R^1$—Y—NCO in the presence of a suitable inert solvent, for example dichloromethane, at a suitable temperature, for example ambient temperature.

There is also provided a process for the preparation of a compound of formula (I) which process comprises the reaction of a compound of formula (IVM)

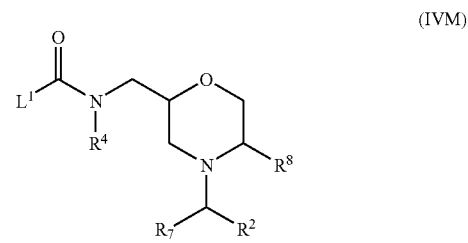

(IVM)

wherein $R^2$, $R^4$, $R^7$, and $R^8$ are as hereinbefore defined and $L^1$ is a resin-bound leaving group, for example a polystyrene resin-bound, typically a Merrifield resin-bound, 4-thiophenoxy group, with a compound of formula (II) and thereafter, if required, carrying out one or more of the following optional steps:

(i) converting a compound of formula (I) to a further compound of formula (I);

(ii) removing any necessary protecting group;

(iii) preparing a salt or solvate of the compound so formed.

Typically, the compound of formula (IVM) is reacted with a compound of formula (II) in the presence of a suitable solvent, for example 1-methyl-2-pyrrolidinone, and heated, for example in a 600 W microwave oven for a suitable period of time, for example 3-10 minutes. A suitable solvent, for example dichloromethane, and formyl polystyrene resin are then added and the mixture shaken at ambient temperature for 12-18 hours. The suspension is then poured onto an acidic solid-phase extraction column, for example Isolute SCX sulphonic acid, washed with methanol and eluted with methanolic ammonia solution. The solvent is then removed from the basic fraction in vacuo to yield the product. The product is then purified by conventional means e.g. column chromatography, suitably a silica solid phase extraction cartridge.

The compound of formula (IVM) may be prepared from a suitable polystyrene resin by conventional means, for example those disclosed in Tetrahedron Lett. (1998), 39(22), 3631-3634.

A compound of formula (III) may be prepared by reaction of a compound of formula (IV);

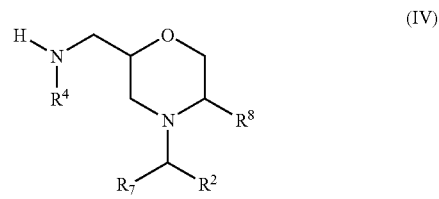

(IV)

wherein $R^4$, $R^7$, $R^8$, and $R^2$ are as hereinbefore defined for formula (I); with a compound of formula U-L wherein U is a urea-forming group as hereinbefore defined and L is a leaving group. A suitable leaving group is a halo group such as chloro.

The reaction between the compound of formula (IV) and the compound U-L is performed in a suitable solvent, for example dichloromethane, in the presence of a suitable base, such as a tertiary amine, for example triethylamine, at a suitable temperature, for example those in the range of −5° C. to +5° C. over a suitable period of time, for example 3-5 hours.

A compound of formula (IV) wherein $R^4$ and $R^7$ are both hydrogen may be prepared by Reaction (a). A compound of formula (IV) wherein $R^4$ and $R^7$ are both hydrogen may be also prepared by Reaction (b). A compound of formula (IV) wherein $R^4$ is hydrogen or $C_{1-6}$alkyl and $R^7$ is hydrogen or $C_{1-6}$alkyl may be prepared by Reaction (c). The S-enantiomer of a compound of formula (IV) may be prepared by Reaction (b).

Reaction (a). Reaction of the compound of formula (V) with a compound of formula (VI)

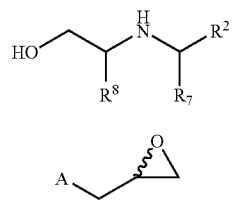

(V)

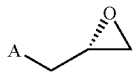

(VI)

wherein $R^2$, $R^7$, and $R^8$ are as hereinbefore defined for formula (I) and A is a protected amino group, suitably phthalimido, followed by deprotection of the amino group to give a compound of formula (IV) wherein $R^4$ and $R^7$ are both hydrogen i.e. a compound of formula (IVR)

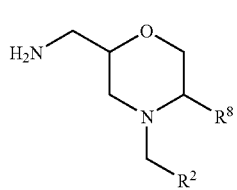

(IVR)

wherein $R^2$, $R^7$, and $R^8$ are as hereinbefore defined, and optionally resolution of the resulting enantiomers of a compound of formula (IVR);

or;

Reaction (b). Reaction of a compound of formula (V) as hereinbefore defined with a compound of formula (VIA)

(VIA)

wherein A is as hereinbefore defined for formula (VI), followed by deprotection of the amino group to give the corresponding enantiomer of a compound of formula (IV) wherein $R^4$ is hydrogen i.e. a compound of formula (IVE)

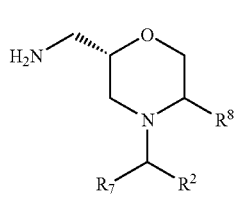

(IVE)

wherein $R^2$, $R^7$, and $R^8$ are as hereinbefore defined.

Reaction (c). Hydrolysis of a compound of formula (VII);

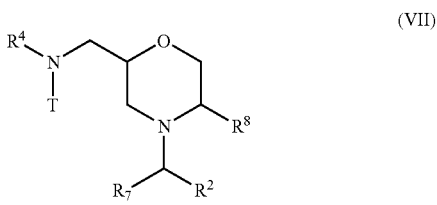

(VII)

wherein T is trifluoroacetyl, and $R^4$, $R^7$, $R^8$, and $R^2$ are as hereinbefore defined for formula (I) and optionally resolution of the resulting enantiomers of a compound of formula (IV).

For both reactions (a) and (b), the cyclisation of the intermediate diols (IVBR) and (IVBE) in the reaction between the compound of formula (V) and a compound of formula (VI) or (VIA) is typically carried out under the Mitsunobu conditions as follows:

Typically, a mixture of the compound of formula (V) and the compound of formula (VI) or formula (VIA) in a suitable solvent, such as tetrahydrofuran, is stirred, suitably for 20-24 hours at a suitable temperature, suitably the reflux temperature of the solvent, under an inert atmosphere, suitably an atmosphere of nitrogen. Further solvent is then added and the mixture cooled, suitably to 0-5° C. A suitable phosphine, such as triphenyl phosphine, is added and the mixture stirred until all the solid is dissolved. A suitable azo compound, such as diisopropylazodicarboxylate, is then added over a period of time, suitably, 10-15 minutes, while maintaining the temperature at <7° C. The mixture is allowed to stand for a period of time, suitably 2-3 hours, then allowed to warm, suitably to 20-25° C. After a further period of standing, suitably 4-6 hours, further phosphine and azo compounds are added. After a further period of standing, suitably 20-24 hours, the reaction mixture is concentrated to near dryness. A suitable alcohol, suitably propan-2-ol, is added and the concentration step repeated; the alcohol addition and concentration step is then repeated. Further alcohol is then added and the mixture heated to a temperature suitably between 65-75° C. After a suitable period, suitably 20-45 minutes, the resultant slurry is cooled, suitably to 20-25° C., and then allowed to stand, suitably for 1.5-3 hours, after which time the product is isolated by filtration. The filter bed is washed with more alcohol and then dried in vacuo at 35-45° C. to yield the protected form of the compound of formula (IVR) or formula (IVE) respectively.

The removal of the protecting group from the product is typically carried out as follows. A slurry of the protected form of the compound of formula (IVR) or formula (IVE) in an appropriate polar solvent, suitably water, is heated to elevated temperature, suitably 70-75° C. and then treated dropwise with a concentrated mineral acid, suitably concentrated sulphuric acid. The mixture was then heated at elevated temperature, suitably the reflux temperature of the solvent, for a suitable period of time, suitably 20-24 hours, after which the reaction mixture was cooled to 20-25° C. and then treated with a suitable apolar solvent, suitably dichloromethane. A base, suitably 0.880 ammonia solution, is then added dropwise, maintaining the temperature between 20-25° C. Further apolar solvent is then added, the aqueous phase then being separated and extracted with further apolar solvent. The combined organic phase is washed with water and then evaporated to dryness. Further apolar solvent is added and re-evaporated to give the compound of formula (IVR) or formula (IVE).

The process for the preparation of the protected form of the compound of formula (IVR) or formula (IVE) described above may also be undertaken in two stages, in which an intermediate compound of formula (IVBR) or of formula (IVBE) respectively;

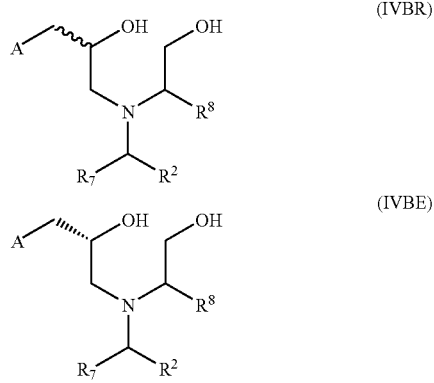

wherein A is as hereinbefore defined for formulae (VI) and (VIA) and $R^2$, $R^7$, and $R^8$ as hereinbefore defined for formula (I); is isolated.

Typically, a mixture of the compound of formula (V) and a compound of formula (VI) or formula (VIA) in a suitable solvent, such as tetrahydrofuran, is stirred, suitably for 20-24 hours at a suitable temperature, suitably the reflux temperature of the solvent, under an inert atmosphere, suitably an atmosphere of nitrogen. Further compound of formula (V) is added and the mixture heated at a suitable temperature, suitably the reflux temperature of the solvent, under an inert atmosphere, suitably an atmosphere of nitrogen, for a suitable period of time, suitably 3-6 hours. The reaction mixture is then cooled, suitably to 20-25° C., and the compound precipitated by means of addition of a suitable co-solvent, suitably diisopropyl ether. The compound of formula (IVBR) or formula (IVBE) respectively is isolated by filtration, washed with further co-solvent and dried in vacuo.

A protected form of the compound of formula (IVR) or formula (IVE) may then be prepared from a compound of formula (IVBR) or formula (IVBE) under similar conditions to those of the reaction between a compound of formula (V) and formulae (VI) or (VIA) as hereinbefore described, but omitting the reflux period prior to the addition of the phosphine and azo compounds.

Reaction (c) is typically carried out by stirring a solution of the compound of formula (VII) in a suitable solvent, for example a mixture of methanol and water, and adding a suitable base, for example potassium carbonate. The mixture is stirred at a suitable temperature, for example those in the range 20-25° C. for a suitable time, for example 16-20 hours followed by removal of the organic solvent in vacuo. Water is then added and the mixture extracted with a suitable organic solvent, for example ethyl acetate. The combined organic phases are washed with water and saturated aqueous sodium chloride solution before drying over a suitable drying agent, for example sodium sulphate, filtering and evaporating the solvent in vacuo. The crude product is then purified by flash chromatography.

The separation of the stereoisomers of the compound of formula (IVE) may be undertaken using techniques well known to those skilled in the art, for example diastereoisomers may be separated using conventional techniques such as column chromatography, preparative high performance liquid chromatography (HPLC), or fractional crystallisation. Enantiomers may be resolved using conventional techniques such as chiral column chromatography, chiral HPLC, or by the fractional crystallisation of diastereoisomeric salts.

A compound of formula (VII) may be prepared by reaction of a compound of formula (VIII) with a compound of formula (IX)

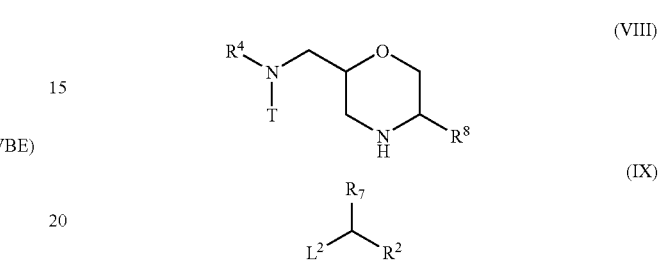

wherein;

T, $R^4$, $R^7$, $R^8$, and $R^2$ are as hereinbefore defined for formula (VII) and $L^2$ is a leaving group. A suitable leaving group, $L^2$ is a halo group such as chloro. The reaction between a compound of formula (VIII) and a compound of formula (IX) is typically carried out by stirring a solution of the compound of formula (VIII) in a suitable solvent, for example N,N-dimethylformamide, under an inert atmosphere, for example an atmosphere of nitrogen, with the addition of a suitable base, for example potassium carbonate, and a suitable activating agent, such as sodium iodide. A solution of a compound of formula (IX) in a suitable solvent, such as N,N-dimethylformamide, is added dropwise to the mixture. The mixture is then stirred at a suitable temperature, for example a temperature in the range of 20-25° C., for a suitable period of time, for example 16-20 hours before removing the volatile components in vacuo. The residue is partitioned between a suitable organic solvent, for example dichloromethane, and a saturated aqueous base, for example saturated aqueous sodium carbonate solution. The organic phase is then washed with additional saturated aqueous base and water before drying over a suitable drying agent, for example magnesium sulphate, filtering and evaporation of the solvent in vacuo to yield the crude product. The crude product is purified by flash chromatography.

A compound of formula (VIII) may be prepared by reaction of a compound of formula (X) with a compound of formula (XI);

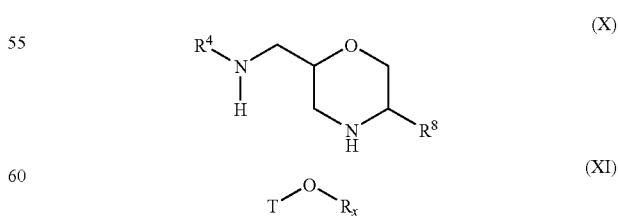

wherein $R^4$, $R^8$, and T are as hereinbefore defined for formula (VII) and $R_x$ is an alkyl group, suitably ethyl.

The reaction between a compound of formula (X) and a compound of formula (XI) is typically carried out by stirring a solution of a compound of formula (X) in a suitable organic solvent, for example methanol, under an inert atmosphere, for example an atmosphere of nitrogen, and then adding a solution of a compound of formula (XI) in a suitable organic solvent, for example ether. The mixture is then stirred for a suitable period of time, for example 20-40 minutes at a suitable temperature, for example a temperature in the range of 20-25° C. and the volatile components removed in vacuo. The residue is then dissolved in a suitable organic solvent, for example methanol, and the volatile components removed in vacuo.

Compounds of formula (II) wherein Y is —CH$_2$— are either commercially available, or may be prepared by reduction of a compound of formula (XII)

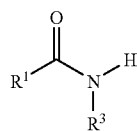

(XII)

wherein $R^1$ and $R^3$ are as hereinbefore defined for formula (I), with a suitable reducing agent such as an alkali metal borohydride or diborane-tetrahydrofuran complex.

The reduction of a compound of formula (XII) is typically carried out using lithium borohydride in a suitable organic solvent, such as a mixture of methanol and diglyme, at elevated temperature, conveniently the reflux temperature of the chosen solvent, for a suitable time period, e.g. 1.5-3 hours.

Compounds of formula (XII) are either known, commercially available compounds, or compounds of formula (XII) may be prepared by activation of a compound of formula (XIII) followed by amination thereof;

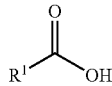

(XIII)

wherein $R^1$ is as hereinbefore defined for formula (I). Suitable activating agents are agents which substitute the hydroxy group for a more labile leaving group. A suitable activating agent is thionyl chloride. A suitable amination agent is 0.880 ammonia.

The amination of a compound of formula (XIII) is typically carried out by heating the compound of formula (XIII) together with thionyl chloride at reflux under an inert atmosphere, such as an atmosphere of nitrogen, for a suitable time period, e.g. 1-2 hours. Following removal of excess thionyl chloride by evaporation, the residue is dissolved in a suitable solvent, such as a polar organic solvent, e.g. tetrahydrofuran and treated with 0.880 ammonia at ambient temperature, such as about 18-25° C.

Compounds of formula (II) wherein $R^1$ is a 1,2,4-oxadiazol-3-yl group substituted at the 5-position, a 1,2,4-oxadiazol-5-yl group substituted at the 3-position, or a 1,3,4-oxadiazol-5-yl substituted at the 2-position, and Y is —CH$_2$—may be prepared by deprotection of a compound of formula (XIV)

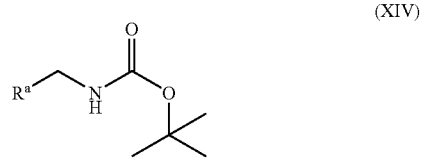

(XIV)

wherein $R^a$ is a 1,2,4-oxadiazol-3-yl group substituted at the 5-position, a 1,2,4-oxadiazol-5-yl group substituted at the 3-position, or a 1,3,4-oxadiazol-5-yl substituted at the 2-position.

Typically, a solution of a compound of formula (XIV) is dissolved in a solution of hydrogen chloride in a suitable solvent, such as 1,4-dioxane and stirred at ambient temperature, such as about 18-25° C., for a suitable time period, such as 1-2 hours.

A compound of formula (XIV) wherein $R^a$ is 1,2,4-oxadiazol-3-yl may be prepared by reaction of a compound of formula (XV) with the compound of formula (XVI)

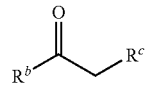

(XV)

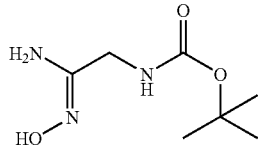

(XVI)

wherein $R^b$ is the desired substituent at the 5-position of the 1,2,4-oxadiazol-3-yl moiety and $R^c$ is $C_{1-6}$alkyl.

Typically, a compound of formula (XV) and the compound of formula (XVI) are dissolved in a suitable solvent, such as an alkanol, e.g. ethanol, and an alkali metal alkoxide, e.g. sodium ethoxide, added. The reaction mixture is heated, conveniently at the reflux temperature of the chosen solvent, over molecular sieves for an appropriate time period, e.g. 2-3 hours.

The compound of formula (XVI) may be prepared from the compound of formula (XVII) by reaction with hydroxylamine.

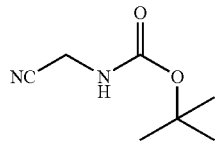

(XVII)

Typically, the reaction between the compound of formula (XVII) and hydroxylamine is carried out in a suitable polar solvent, such as a mixture of an alkanol, e.g. ethanol, and water, in the presence of a suitable base, such as an alkali metal carbonate, e.g. potassium carbonate, at elevated temperature, conveniently the reflux temperature of the chosen solvent, for an appropriate time period, e.g. about 2 days.

The compounds of formulae (V), (VI), (VIII), (IX), compounds of formula (X) wherein $R^8$ is hydrogen, (XI), (XII), (XIII), (XV), and (XVII), and certain compounds of formulae (II) and (VII) are known, commercially available compounds and/or may be prepared by analogy with known procedures, for examples those disclosed in standard reference texts of synthetic methodology such as *J. March, Advanced Organic Chemistry*, 3rd Edition (1985), *Wiley Interscience*. Compounds of formula (X) wherein $R^8$ is other than hydrogen may be prepared using methods disclosed in WO 02/26722 and WO 02/26723.

Certain compounds of formulae (III), (IVBR), (IVBE) are considered to be novel.

Accordingly, there is provided a compound selected from the list consisting of:
[(2S)-4-(3-Chloro-4-fluoro-benzyl)morpholin-2-ylmethyl] carbamic acid tert-butyl ester;
C-[(2S)-4-(3-Chloro-4-fluoro-benzyl)-morpholin-2-yl]-methylamine;
[(2S)-4-(3-Chloro-4-fluoro-benzyl)morpholin-2-ylmethyl] carbamic acid 4-nitro-phenyl ester;
1-(5-Chloromethyl-[1,3,4]oxadiazol-2-ylmethyl)-3-[(2S)-4-(3,4-dichlorobenzyl)morpholin-2-ylmethyl]urea;
{(2S)-4-[1-(3,4-Difluorophenyl)ethyl]morpholin-2-ylmethyl}carbamic acid 4-nitro-phenyl ester;
{(2S)-4-[1-(3,4-Difluorophenyl)ethyl]morpholin-2-ylmethyl}carbamic acid 4-nitro-phenyl ester Isomer I;
{(2S)-4-[1-(3,4-Difluorophenyl)ethyl]morpholin-2-ylmethyl}carbamic acid 4-nitro-phenyl ester Isomer II;
C-{(2S)-4-[1-(3,4-Difluorophenyl)ethyl]morpholin-2-yl}methylamine dihydrochloride;
{(2S)-4-[1-(3,4-Difluoro-phenyl)-ethyl]-morpholin-2-ylmethyl}-carbamic acid tert-butyl ester;
N'-(5-{3-[(2S)-4-(3,4-Dichloro-benzyl)morpholin-2-ylmethyl]ureidomethyl}furan-3-carbonyl)hydrazinecarboxylic acid tert-butyl ester;
1-[(2S)-4-(3,4-Dichloro-benzyl)morpholin-2-ylmethyl]-3-(4-hydrazinocarbonyl-furan-2-ylmethyl)urea hydrochloride, and;
1-[4-(N'-Formyl-hydrazinocarbonyl)furan-2-ylmethyl]-3-[(2S)-4-(3,4-dichloro-benzyl)morpholin-2-ylmethyl]urea.

The following compounds are also considered to be novel and accordingly form a further aspect of the invention:
2-(5-Methyl-[1,3,4]oxadiazol-2-yl)ethylamine hydrochloride;
5-Aminomethyl-[1,3,4]oxadiazole-2-carboxylic acid methylamide hydrochloride;
2-Aminomethyloxazole-4-carboxylic acid methyl ester;
5-[(2,2,2-Trifluoro-acetylamino)methyl]furan-3-carboxylic acid methylamide;
5-Aminomethyl-furan-3-carboxylic acid methylamide;
[3-(N'-Acetyl-hydrazino)-3-oxo-propyl]carbamic acid tert-butyl ester;
[2-(5-Methyl-[1,3,4]oxadiazol-2-yl)ethyl]carbamic acid tert-butyl ester;
5-Aminomethylthiophene-3-carboxylic acid methylamide;
5-[(2,2,2-Trifluoroacetylamino)methyl]thiophene-3-carboxylic acid methylamide, and;
(5-Methylcarbamoyl-[1,3,4]oxadiazol-2-ylmethyl)carbamic acid tert-butyl ester.

The above mentioned conversion of a compound of formula (I) into another compound of formula (I) includes any conversion which may be effected using conventional procedures, but in particular the said conversions include converting one group $R^1$ into another group $R^1$. The above mentioned conversion may be carried out using any appropriate method under conditions determined by the particular groups chosen. Thus, suitable conversions of one group $R^1$ into another group $R^1$ include:

(a) converting a group $R^1$ which represents a heteroaryl group substituted with an alkoxycarbonyl group into a group $R^1$ which represents a heteroaryl group substituted with a carboxy group; such a conversion may be carried out using an appropriate conventional hydrolysis procedure, for example treating an appropriately protected compound of formula (I) with a suitable aqueous base;

(b) converting a group $R^1$ which represents a heteroaryl group substituted with a carboxy group into a group $R^1$ which represents a heteroaryl group substituted with an alkylaminocarbonyl group; such a conversion may be carried out using an appropriate conventional amination procedure, for example treating an appropriately protected compound of formula (I) with a suitable amine in the presence of a suitable peptide coupling agent and, if required, a suitable activating agent;

(c) converting a group $R^1$ which represents unsubstituted heteroaryl group into a group $R^1$ which represents an alkylated heteroaryl group; such a conversion may be carried out using an appropriate conventional alkylating procedure, for example treating an appropriately protected compound of formula (I) with an alkyl halide in the presence of a suitable base, and;

(d) converting a group $R^1$ which represents a heteroaryl group substituted with an alkoxycarbonyl group into a group $R^1$ which represents a heteroaryl group substituted with an alkylaminocarbonyl, or cycloalkylaminocarbonyl group, or an N-heterocyclylcarbonyl group; such a conversion may be carried out using an appropriate conventional amination procedure, for example treating an appropriately protected compound of formula (I) with an amine.

(e) converting a group $R^1$ which represents tetrazolyl into a group $R^1$ which represents 2-mono-, di-, or tri-halomethyl-1,3,4-oxadiazole; such a conversion may be carried out by treating an appropriately protected compound of formula (I) with mono-, di-, or tri-haloacetic anhydride.

(f) converting a group $R^1$ which represents tetrazolyl into a group $R^1$ which represents a 2-(N,N-dialkylamino)methyl 1,3,4-oxadiazole; such a conversion may be carried out by treating an appropriately protected compound of formula (I) with chloroacetic anhydride, then treating the resultant chloromethyl derivative with a secondary amine.

(g) converting a group $R^1$ which represents a 3-furan ethylcarboxylate group into a group $R^1$ which represents a 3-furan-(3-methyl-1,2,4-oxadiazole; such a conversion may be carried out using acetamidoxime, followed by the addition of molecular sieves and treatment with a suitable base, for example an alkali metal alkoxide such as sodium ethoxide.

(h) converting a group $R^1$ which represents a heteroaryl group substituted with a carboxy group into a group $R^1$ which represents a heteroaryl group substituted with an oxadiazolyl group; such a conversion may be carried out in three steps; first the carboxy group is reacted with t-butylcarbazide in the presence of 1-hydroxybenzotriazole, a suitable tertiary amine such as diisopropylethylamine, and a suitable peptide coupling agent such as 1-(3-dimethylaminopropyl)-3-ethylcarbodiimide. Secondly, the product from the first step is reacted with a solution of a mineral acid such as hydrochloric acid in a suitable solvent, such as dioxane. Thirdly, the product from the second step is reacted with triethylorthoformate in the presence of a suitable base, such as triethylamine, and molecular sieves.

Or, converting a group $R^1$ which represents a heteroaryl group substituted with a carboxy group into a group $R^1$ which represents a heteroaryl group substituted with a triazolyl group; such a conversion may also be carried out in three steps; first the carboxy group is recated with t-butylcarbazide in the presence of 1-hydroxybenzotriazole, a suitable tertiary amine such as diisopropylethylamine, and a suitable peptide coupling agent such as 1-(3-dimethylaminopropyl)-3-ethylcarbodiimide. Secondly, the product from the first step is reacted with a solution of a mineral acid such as hydrochloric acid in a suitable solvent, such as dioxane. Thirdly, to the product of the second step is added a suitable imidate, such as ethyl acetimidate hydrochloride. To the solution is added a suitable tertiary base such as triethylamine and molecular sieves such as activated 4A powdered molecular sieves (0.360 g). The suspension is heated to reflux for 18-24 hours. The mixture is cooled and the solvent removed to yield the crude product.

(i) converting a group $R^1$ which represents a heteroaryl group substituted with a carboxy group into a group $R^1$ which represents a heteroaryl group substituted with an oxadiazolyl group; such a conversion may be carried out by treatment of a suitably protected compound of formula (I) with 1-(3-dimethylaminopropyl)-3-ethylcarbodiimide hydrochloride in the presence of a suitable activating agent such as 1-hydroxybenzotriazole in the presence of a suitable tertiary base such as N,N-diisopropylethylamine, followed by heating the resulting formylhydrazinocarbonyl compound with (methoxycarbonylsulphamoyl)triethylammonium hydroxide in a microwave oven.

(j) converting a group $R^1$ which represents pyrazolyl into a group $R^1$ which represents 1-acetylpyrazolyl; such a conversion may be carried out using an appropriate conventional acylation procedure, for example treating an appropriately protected compound of formula (I) with an carboxylic anhydride in the presence of a suitable base.

(k) converting a group $R^1$ which represents an unsubstituted tetrazoyl group into a group $R^1$ which represents a tetrazolyl group substituted with an N-alkyl group; such a conversion may be carried out using an appropriate conventional alkylation procedure, for example reacting a suitably protected compound of formula (I) with trifluoroacetic acid, tert-butyl alcohol, and conc. sulphuric acid. The mixture is stirred at ambient temperature for 12-18 hours before water is added and the mixture basified by addition of a suitable base such as 2M sodium hydroxide solution. The crude product is then isolated by conventional means such as solid-phase extraction.

(l) converting a group $R^1$ which represents a heteroaryl group substituted with an amino group into a group $R^1$ which represents a heteroaryl group substituted with a formamido group; such a conversion may be carried out by reaction of a suitably protected compound of formula (I) with an aqueous solution of formic acid in a suitable solvent such as acetonitrile at elevated temperature.

The above mentioned conversions may as appropriate be carried out on any of the intermediate compounds mentioned herein.

Suitable protecting groups in any of the above mentioned reactions are those used conventionally in the art. The methods of formation and removal of such protecting groups are those conventional methods appropriate to the molecule being protected, for example those methods discussed in standard reference texts of synthetic methodology such as *P J Kocienski, Protecting Groups*, (1994), *Thieme*.

For any of the hereinbefore described reactions or processes, conventional methods of heating and cooling may be employed, for example electric heating mantles and ice/salt baths respectively. Conventional methods of purification, for example crystallisation and column chromatography may be used as required.

Where appropriate individual isomeric forms of the compounds of formula (I) may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

The salts and solvates of the compounds of formula (I) may be prepared and isolated according to conventional procedures.

Compounds of the invention may be tested for in vitro biological activity in accordance with the following assays:

(a) CCR-3 Binding Assay

A CCR-3 competition binding SPA (scintillation proximity assay) was used to assess the affinity of novel compounds for CCR-3. Membranes prepared from K562 cells stably expressing CCR-3 (2.5 µg/well) were mixed with 0.25 mg/well wheat-germ agglutinin SPA beads (Amersham) and incubated in binding buffer (HEPES 50 mM, $CaCl_2$ 1 mM, $MgCl_2$ 5 mM, 0.5% BSA) at 4° C. for 1.5 hr. Following incubation, 20 pM of [$^{125}$I] eotaxin (Amersham) and increasing concentrations of compound (1 pM to 30 µM) were added and incubated in a 96 well plate for 2 hr at 22° C. then counted on a Microbeta plate counter. The total assay volume was 100 µl. Competition binding data were analysed by fitting the data with a four parameter logistic equation. Data are presented as the mean $pIC_{50}$ values (negative logarithm of the concentration of compound which inhibits eotaxin binding by 50%) from at least two experiments.

(b) Eosinophil Chemotaxis Assay.

Compounds were evaluated for their inhibitory effect on eosinophil chemotaxis. Eosinophils were purified from human peripheral blood by standard CD16 cell depletion using a Miltenyi cell separation column and a magnetic Super Macs magnet as previously described (Motegi & Kita, 1998; J. Immunology. 161:4340-6). Cells were re-suspended in RPMI 1640/10% FCS solution and incubated with calcein-AM (Molecular Probes) at 37° C. for 30 mins. Following incubation, the eosinophils were centrifuged at 400 g for 5 min and re-suspended in RPMI/FCS at 2.2 million/ml. Cells were then incubated in the presence of increasing concentration of compounds (1 pM to 30 µM) at 37° C. for 30 mins. For control responses cells were incubated with RPMI/FCS only. The agonist eotaxin (an $EC_{80}$ concentration) was added to the lower chamber of a 96 well chemotaxis plate (5 µm filter: Receptor Technologies). Eosinophils (50 µl of 2 million/ml cells) were added to the top chamber of the filter plate and incubated at 37° C. for 45 mins. Cells remaining on top of the chemotaxis filter were removed and the number of eosinophils which had migrated were quantified by reading the plate on a fluorescent plate reader. Inhibition curves for the effect of compounds on eosinophil chemotaxis were analysed by fitting the data with a four parameter logistic equation. Functional $pK_i$ values ($fpK_i$) were generated using the equation below (Lazareno & Birdsall, 1995. Br. J. Pharmacol 109: 1110-9).

$$fpKi = \frac{IC_{50}}{1 + \frac{[\text{Agonist}]}{EC_{50}}}$$

The compounds of the Examples were tested in the CCR-3 binding and/or eosinophil chemotaxis assays (assays (a) and (b)). The compounds of the Examples tested in the CCR-3 binding assay typically possessed pIC50 values in the range 5.0-10.0. The compounds of the Examples tested in the CCR-3 eosinophil chemotaxis assay possessed fpKi values such as those given in the table below:

| Example No. | fpKi |
|---|---|
| 8 | 8.8 |
| 11 | 9.0 |
| 19 | 7.8 |
| 97 | 9.2 |
| 116 | 9.8 |

Examples of disease states in which the compound of the invention has potentially beneficial anti-inflammatory effects include diseases of the respiratory tract such as bronchitis (including chronic bronchitis), bronchiectasis, asthma (including allergen-induced asthmatic reactions), chronic obstructive pulmonary disease (COPD), cystic fibrosis, sinusitis and rhinitis. Other relevant disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure.

Furthermore, the compound of the invention may be used to treat nephritis, skin diseases such as psoriasis, eczema, allergic dermatitis and hypersensitivity reactions and diseases of the central nervous system which have an inflammatory component (e.g. Alzheimer's disease, meningitis, multiple sclerosis) HIV and AIDS dementia.

Compounds of the present invention may also be of use in the treatment of nasal polyposis, conjunctivitis or pruritis.

Further examples of disease states in which the compound of the invention have potentially beneficial effects include cardiovascular conditions such as atherosclerosis, peripheral vascular disease and idiopathic hypereosinophilic syndrome. Other diseases for which the compound of the present invention may be beneficial are other hypereosinophilic diseases such as Churg-strauss syndrome. Additionally, eosinophilia is commonly found in parasitic diseases, especially helminth infections, and thus the compound of the present invention may be useful in treating inflammation arising from hypereosinophilic states of diseases such as hydatid cyst (*Echinococcus* sp.), tapeworm infections (*Taenia* sp.), blood flukes (schistosomiasis), and nematode (round worms) infections such as: —Hookworm (*Ancylostoma* sp.), Ascaris, Strongyloides, Trichinella, and particularly lymphatic filariasis including Onchocerca, Brugia, Wucheria (Elephantiasis).

The compounds of the invention may be useful as an immunosuppressive agent and so have use in the treatment of autoimmune diseases such as allograft tissue rejection after transplantation, rheumatoid arthritis and diabetes.

Compounds of the invention may also be useful in inhibiting metastasis.

Diseases of principal interest include asthma, COPD and inflammatory diseases of the upper respiratory tract involving seasonal and perennial rhinitis.

Preferred diseases of principal interest include asthma and inflammatory diseases of the upper respiratory tract involving seasonal and perennial rhinitis.

Further diseases also of principle interest include inflammatory diseases of the gastrointestinal tract such as inflammatory bowel disease.

It will be appreciated by those skilled in the art that references herein to treatment or therapy extend to prophylaxis as well as the treatment of established conditions.

As mentioned above, compounds of formula (I) are useful as therapeutic agents.

There is thus provided as a further aspect of the invention a compound of formula (I) or a physiologically acceptable salt or solvate thereof for use as an active therapeutic agent.

There is also therefore provided a compound of formula (I), or a physiologically acceptable salt or solvate thereof, for use in the treatment of inflammatory conditions, e.g. asthma or rhinitis.

According to another aspect of the invention, there is provided the use of a compound of formula (I) or a physiologically acceptable salt or solvate thereof for the manufacture of a medicament for the treatment of inflammatory conditions, eg. asthma or rhinitis.

In a further or alternative aspect there is provided a method for the treatment of a human or animal subject suffering from or susceptible to an inflammatory condition e.g. asthma or rhinitis, which method comprises administering an effective amount of a compound of formula (I) or a physiologically acceptable salt or solvate thereof.

The compounds according to the invention may be formulated for administration in any convenient way.

There is thus further provided a pharmaceutical composition comprising a compound of formula (I), or a physiologically acceptable salt or solvate thereof, and optionally one or more physiologically acceptable diluents or carriers.

There is also provided a process for preparing such a pharmaceutical formulation which comprises admixing the compound of formula (I) or a physiologically acceptable salt or solvate thereof with one or more physiologically acceptable diluents or carriers.

The compounds according to the invention may, for example, be formulated for oral, inhaled, intranasal, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds and pharmaceutical compositions according to the invention may also be used in combination with other therapeutic agents, for example antihistaminic agents, anticholinergic agents, anti-inflammatory agents such as corticosteroids, e.g. fluticasone propionate, beclomethasone dipropionate, mometasone furoate, triamcinolone acetonide or budesonide; or non-steroidal anti-inflammatory drugs (NSAIDs) eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists; or beta adrenergic agents such as salmeterol, salbutamol, formoterol, fenoterol or terbutaline and salts thereof; or antiinfective agents e.g. antibiotic agents and antiviral agents. It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.001 to 500 mg/kg body weight, preferably 0.01 to 500 mg/kg body weight, more preferably 0.01 to 100 mg/kg body weight, and at any appropriate frequency e.g. 1 to 4 times daily. The precise dosing regimen will of course depend on factors such as the therapeutic indication, the age and condition of the patient, and the particular route of administration chosen.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

DETAILED DESCRIPTION

The invention is illustrated by reference to, but is in no way limited by, the following Examples.

For the avoidance of doubt, the free bond on the $R^1$ groups as presented in the Tables signifies the point of attachment of the $R^1$ groups to the residue of the molecule.

It should be noted that, for clarity, compounds of the Descriptions and the Examples are referred to by number, for example "Description 3" and "Example 26". The structures of the Example compounds so referred to are given in Tables 1 to 9.

General Experimental Details

Mass Directed Automated Preparative HPLC column, Conditions and Eluent

Mass directed automated preparative high performance liquid chromatography was carried out using an LCABZ+ 5 μm (5 cm×10 mm internal diameter) column, employing gradient elution using two solvent systems, (A) 0.1% formic acid in water, and (B) 95% acetonitrile and 0.5% formic acid in water, at a flow rate of 8 ml min$^{-1}$. Mass spectrometry was carried out using a VG Platform Mass Spectrometer, with an HP1100 Diode Array Detector and Accurate Flow Splitter.

LC/MS System

The following Liquid Chromatography Mass Spectroscopy (LC/MS) System was used:

This system used an 3 μm ABZ+PLUS (3.3 cm×4.6 mm internal diameter) column, eluting with solvents: A-0.1% v/v formic acid+0.077% w/v ammonium acetate in water; and B—95:5 acetonitrile:water+0.05% v/v formic acid, at a flow rate of 3 ml per minute. The following gradient protocol was used: 100% A for 0.7 mins; A+B mixtures, gradient profile 0-100% B over 3.5 mins; hold at 100% B for 1.1 mins; return to 100% A over 0.2 mins.

The LC/MS system used a micromass spectrometer, with electrospray ionisation mode, positive and negative ion switching, mass range 80-1000 a.m.u.

Thermospray Mass Spectra

Thermospray Mass Spectra were determined on a HP 5989A engine mass spectrometer, +ve thermospray, source temperature 250° C., probe temperatures 120° C. (stem), 190° C. (tip), detection mass range 100-850 a.m.u. Compounds were injected in 10 μl of a mixture of solvents comprising 65% methanol and 35% 0.05M aqueous ammonium acetate, at a flow rate of 0.7 ml/min.

Solid Phase Extraction (Ion Exchange)

'SCX' refers to Isolute Flash SCX-2 sulphonic acid solid phase extraction cartridges.

All temperatures are in ° C.

DESCRIPTIONS

Description 1:
2,2,2-Trifluoro-N-(morpholin-2-ylmethyl)acetamide

To a stirred solution of morpholin-2-ylmethylamine (3.1 g) in methanol (70 ml) under nitrogen was added an ethereal solution of ethyl-α,α,α-trifluoroacetate (5 ml in 20 ml ether) which had been washed with saturated aqueous sodium bicarbonate, water and brine, and dried. The mixture was stirred for 30 min at 22° C. before removal of all volatiles in vacuo.

The residue was dissolved in methanol (10 ml) and the volatiles again removed in vacuo to give the title compound as a white crunchy foam (4.9 g).

Thermospray Mass Spectrum m/z 213 [MH$^+$].

Description 2: N-{[4-(3,4-Dichlorobenzyl)morpholin-2-yl]methyl}-2,2,2-trifluoroacetamide To a stirred solution of Description 1 (3.3 g) in N,N-dimethylformamide (50 ml) under nitrogen was added potassium carbonate (2.46 g) and sodium iodide (2.12 g). A solution of 3,4-dichlorobenzyl chloride (2 ml) in N,N-dimethylformamide (10 ml) was added dropwise to the mixture. The mixture was stirred at 22° C. for 18 h before the volatiles were removed in vacuo. The residue was partitioned between dichloromethane (100 ml) and saturated aqueous sodium carbonate solution (50 ml). The organic phase was subsequently washed with additional saturated aqueous sodium carbonate solution (2×50 ml) and water (50 ml) before drying over magnesium sulphate, filtering and evaporation of the solvent in vacuo to give a pale yellow oil. The oil was purified by Biotage flash chromatography on a 90 g silica cartridge eluting with 25% ethyl acetate in cyclohexane, to give the title compound as a colourless oil (2.97 g).

LC/MS R$_t$ 2.63 min, Mass Spectrum m/z 371 [MH$^+$].

Description 3: [4-(3,4-Dichlorobenzyl)morpholin-2-yl]methylamine

To a stirred solution of Description 2 (2.97 g) in methanol (15 ml) and water (5 ml) was added potassium carbonate (5.53 g). The mixture was stirred at 22° C. for 18 h before the methanol was removed in vacuo. Water (25 ml) was added and the mixture extracted with ethyl acetate (3×30 ml). The combined organic phases were washed with water (5 ml) and saturated aqueous sodium chloride solution (10 ml) before drying over sodium sulphate, filtering and evaporation of the solvent in vacuo to give a pale yellow oil. The oil was purified by Biotage flash chromatography on a 90 g silica cartridge eluting with 75:8:1 dichloromethane/ethanol/0.880 ammonia solution. The required fractions were combined and the solvent evaporated in vacuo to give the title compound as a colourless oil (1.85 g).

LC/MS R$_t$ 1.77 min, Mass Spectrum m/z 275 [MH$^+$].

Description 4: [4-(3,4-Dichlorobenzyl)morpholin-2-yl]methylamine (alternative synthesis)

A mixture of 2-[(3,4-dichlorobenzyl)amino]ethanol (Chem Abs No. 40172-06-3, 0.980 g) and 2-(oxiran-2-ylmethyl)-1H-isoindole-1,3(2H)-dione (1.10 g) was heated at 80° C. under nitrogen for 3 h. The resulting solid mass was treated with concentrated sulphuric acid (1.5 ml) then stirred at 150° C. for 24 h. The mixture was treated with water (100 ml) then washed with ethyl acetate (2×100 ml). The dark aqueous phase was basified to ~pH 12 using 5M aqueous sodium hydroxide, then extracted with ethyl acetate (2×100 ml). The combined organic extracts were washed with water and brine, dried (Na$_2$SO$_4$) and concentrated under vacuum to give the title compound as a brown oil (1.02 g).

Mass spec. m/z 275 (MH$^+$).

Description 5: 1-[(2S)-4-(3,4-Dichlorobenzyl)morpholin-2-yl]methylamine

Description 3 (racemic mixture, 8 g) was separated into its single enantiomers by preparative chiral-HPLC. The separation was carried out using a 2"×22 cm Chiralpak AD 20 μm column, Merck self pack DAC system, eluting with 95:5:0.1 (v/v) heptane: absolute ethanol: diethylamine (flow rate: 55 ml/min over 40 min, UV detection 225 nm); sample load preparation: 400 mg sample in 20 ml 3:2 (v/v) absolute ethanol: system eluent.

The title compound (2.49 g) was obtained as follows: preparative HPLC retention time 23.0 min.

Description 5: (Alternative Procedure)

A slurry of Description 7 (1.00 g) in water (8.5 ml) was heated to 75° C. and then treated dropwise with concentrated sulphuric acid (2.5 ml). The mixture was then heated at reflux. After 23 h the reaction mixture was cooled to 22° C. and then treated with dichloromethane (6 ml). 880 Ammonia solution (7 ml) was then added dropwise with cooling. More dichloromethane (10 ml) was added. The aqueous phase was separated and extracted with more dichloromethane (10 ml). The combined organic phase was washed with water (5 ml) and then evaporated to dryness. The residue was redissolved in dichloromethane and the solvent re-evaporated to give the product as an oil (662 mg).

Description 6: 1-[(2S)-4-(3,4-Dichlorobenzyl)morpholin-2-yl]methanamine salt with D-tartaric acid 1:1

Description 3 (0.613 g) was dissolved in methanol (12.3 ml). D-Tartaric acid (0.335 g) was added and the slurry was heated to reflux for 50 min. The mixture was allowed to cool to 0-5° C. and the precipitate isolated by filtration to give the title compound as a white solid (0.4 g).

ee: 76% ee

Chiral analytical HPLC (Chiralpak AD column, 4.6×250 mm, eluent 50:50:0.1 MeOH: EtOH: Butylamine, flow rate 0.5 ml/min, UV detection at 220 nm), Rt 8.9 min.

Description 7: 2-[4-(3,4-Dichloro-benzyl)-morpholin-2-ylmethyl]-isoindole-1,3-dione A mixture of 2-[(3,4-dichlorobenzyl)amino]ethanol (2.038 g) and (S)-2-(oxiran-2-ylmethyl)-1H-isoindole-1,3(2H)-dione (2.032 g) in tetrahydrofuran (3.3 ml) was stirred and heated at reflux under nitrogen. After 21.5 h more tetrahydrofuran (12.5 ml) was added and the mixture was cooled to 3° C. Triphenyl phosphine (2.793 g) was added and the mixture was stirred until all the solid had dissolved. Diisopropylazodicarboxylate (2.1 ml) was then added over 12 min maintaining the temperature at <7° C. After 2.25 h the mixture was allowed to warm to 22° C. After 5.3 h more triphenylphosphine (121 mg) and diisopropylazodicarboxylate (0.09 ml) were added. After 22.5 h the reaction mixture was concentrated to near dryness. Propan-2-ol (12 ml) was added and the concentration repeated, this was repeated once more. More propan-2-ol (12 ml) was added and the mixture was heated to 70° C. After 0.5 h the slurry was cooled to 22° C. and then after a further 2 h the product was collected by filtration. The bed was washed with propan-2-ol (2×4 ml) and then dried in vacuo at 40° C. to give the product, (2.622 g).

Description 8: 4-Nitrophenyl [4-(3,4-dichlorobenzyl) morpholin-2-yl]methylcarbamate Triethylamine (0.09 ml) was added to solution of Description 3 (0.150 g, 0.545 mmol) in dichloromethane (3 ml) with stirring at 20° C. under nitrogen. The solution was cooled to 0° C. and a solution of 4-nitrophenyl chloroformate (0.121 g) in dichloromethane (1 ml) was added drop-wise. The resultant mixture was stirred for 4 h at 0° C. The solution was allowed to warm to 20° C., washed with brine (4 ml), dried ($MgSO_4$), and concentrated in vacuo. Purification by Biotage flash chromatography on silica gel, eluting with 35% ethyl acetate in cyclohexane, gave the title compound (0.2 g).

LC-MS: Rt 3.1 mins. Mass Spectrum m/z 441 [$MH^+$].

Description 9: 4-Nitrophenyl [(2S)-4-(3,4-dichlorobenzyl)morpholin-2-yl]methylcarbamate Description 9 was prepared in an analogous manner to Description 8 from Description 5 (0.225 g) and 4-nitrophenylchloroformate (0.182 g) to yield the title compound (0.2 g).

LC-MS Rt 3.1 mins. Mass Spectrum m/z 441 [$MH^+$].

Description 10: [(2S)-4-(3,4-difluorobenzyl)morpholin-2-yl]methylamine

Description 10 was made in an analogous manner to that of Description 5. Preparative HPLC retention time 28.3 min

Description 11: 4-Nitrophenyl [(2S)-4-(3,4-difluorobenzyl)morpholin-2-yl]methylcarbamate Description 11 was prepared in an analogous manner to Description 9 from Description 10 and 4-nitrophenylchloroformate.

LC-MS Rt 2.52 mins. Mass Spectrum m/z 408 [$MH^+$].

Description 12: [(2S)-4-(3-chlorobenzyl)morpholin-2-yl]methylamine

Description 12 was made in an analogous manner to that of Description 5. Chiral preparative HPLC retention time 26.1 min

Description 13: {(2S)-4-[(5-chlorothien-2-yl)methyl]morpholin-2-yl}methylamine Description 13 was made in an analogous manner to that of Description 5. Chiral preparative HPLC retention time 25.2 min

Description 14: 4-Nitrophenyl [(2S)-4-[(5-chlorothien-2-yl)methyl]morpholin-2-yl]methylcarbamate Description 14 was prepared in an analogous manner to Description 9 from Description 13 and 4-nitrophenylchloroformate.

LC-MS Rt 2.58 mins. Mass Spectrum m/z 412 [$MH^+$].

Description 16: [(2S)-4-(3-Chloro-4-fluoro-benzyl) morpholin-2-ylmethyl]carbamic acid tert-butyl ester

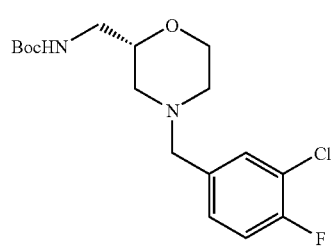

A solution of (R)-(2-morpholinylmethyl)-carbamic acid 1,1-dimethyl ester [CAS 186202-57-3] (0.26 g) in dichloromethane (5 ml) was treated with triethylamine (0.167 ml) and 3-chloro-4-fluorobenzyl bromide (0.27 g). After stirring for 18 hrs the mixture was purified by applying directly to an SCX ion exchange cartridge (10 g), eluting with methanol followed by 10% 0.880 ammonia/methanol. The basic fraction was evaporated in vacuo to give the title compound (0.37 g) as a colourless gum.

LC-MS: Rt=2.46 min. Mass Spectrum m/z 359 [$MH^+$]

Description 17: C-[(2S)-4-(3-Chloro-4-fluoro-benzyl)-morpholin-2-yl]-methylamine

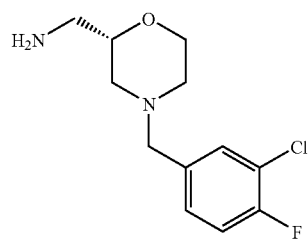

A solution of Description 16 (0.36 g) in dichloromethane (1 ml) was treated with trifluoroacetic acid (1 ml) and allowed to stand for 1 hr. The mixture was concentrated in vacuo and the residue partitioned between dichloromethane and aqueous sodium bicarbonate; the phases were separated and the organic phase dried ($MgSO_4$), filtered and the solvent evaporated in vacuo to give the tile compound (0.25 g) as a colourless gum.

LC-MS: Rt=0.70 min. Mass Spectrum m/z 259 [$MH^+$]

Description 18: [(2S)-4-(3-Chloro-4-fluoro-benzyl)morpholin-2-ylmethyl]carbamic acid 4-nitro-phenyl ester

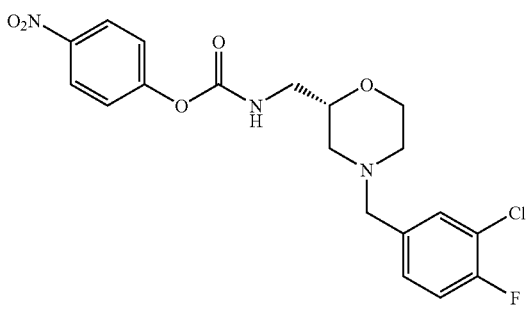

A solution of 4-nitrophenyl chloroformate (0.102 g) in anhydrous dichloromethane (5 ml) at 0° C. was treated, dropwise, with a solution of Description 17 (0.13 g) and triethylamine (0.070 ml) in anhydrous dichloromethane (2 ml). After stirring at room temperature for 18 hrs the mixture was concentrated in vacuo. Chromatographic purification on silica gel (Varian Bond-Elut cartridge, 5 g), eluting with a gradient of ethyl acetate/cyclohexane gave the title compound (0.19 g) as a colourless oil.

LC-MS: Rt=2.66 min. Mass Spectrum m/z 424 [MH$^+$]

Description 19: 2-Methyl-2H-[1,2,3]triazole-4-carboxylic acid amide

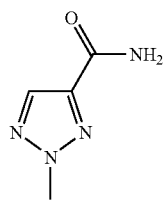

2-Methyl-2H-1,2,3-triazole-4-carboxylic acid (Bull. Soc. Chim. Fr. (1976), (11-12, Pt. 2), 1831-2) (0.127 g) was heated under reflux with thionyl chloride (2 ml) with stirring under nitrogen for 1.75 h. The excess thionyl chloride was evaporated in vacuo and the residue dissolved in tetrahydrofuran (8 ml). 0.880 ammonia (1 ml) was added to the stirred solution at room temperature, and the mixture was stirred at room temperature overnight. The mixture was evaporated to dryness in vacuo to give the title compound as a white solid (0.160 g). NMR (D$_4$-MeOH) δ8.0 (1H, CH); 4.2 (2H, CH$_3$).

Description 20: C-(2-Methyl-2H-[1,2,3]-triazol-4-yl)methylamine hydrochloride

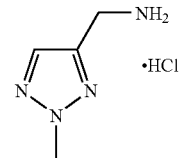

A solution of Description 19 (0.160 g) in bis(2-methoxyethyl)ether (diglyme, 5 ml) was treated with lithium borohydride (0.066 g) and heated to reflux (oil bath 155° C.). Methanol (0.45 ml) was added cautiously, and the mixture heated under reflux for 2 h with stirring under nitrogen. Saturated aqueous ammonium chloride (0.5 ml) was added to the cooled mixture, and the mixture was diluted with methanol (10 ml). The solution was applied directly to an Isolute SCX ion exchange cartridge (10 g) (pre-eluted with methanol) and eluted with methanol followed by 10% 0.880 ammonia in methanol. The ammonia in methanol fraction was evaporated to low volume (ca. 2 ml), acidified with 5N aqueous hydrochloric acid (1 ml), and evaporated to dryness in vacuo to give the title compound as a white solid (0.026 g).

NMR (D$_4$-MeOH) δ7.7 (1H, CH); 4.2 (3H, CH$_3$); 4.24, (2H, CH$_2$).

Description 21: C-(1-Methyl-1H-[1,2,3]triazol-4-yl)methylamine hydrochloride

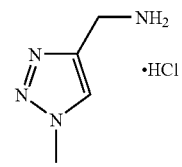

A solution of 1-methyl-1H-1,2,3-triazole-4-carboxamide (Bull. Chem. Soc. Jap. (1972), 45(8), 2577-9) (0.050 g) in bis(2-methoxyethyl)ether (diglyme, 2 ml) was treated with lithium borohydride (0.0264 g) and heated to reflux (oil bath 155° C.). Methanol (0.18 ml) was added dropwise in two portions after 5 min and 35 min, and the mixture heated under reflux for 1.5 h with stirring under nitrogen. Saturated aqueous ammonium chloride (0.2 ml) was added dropwise to the cooled mixture, and the mixture was diluted with methanol (2 ml). The solution was applied directly to an Isolute SCX ion exchange cartridge (5 g) (pre-eluted with methanol) and eluted with methanol followed by 10% 0.880 ammonia in methanol. The ammonia in methanol fraction was evaporated to low volume (ca. 1 ml), acidified with 4N hydrogen chloride in 1,4-dioxane (1 ml), and evaporated to dryness in vacuo to give the title compound (0.030 g).

Thermospray Mass Spectrum m/z 113 [MH$^+$]

Description 22: (N-Hydroxycarbamimidoylmethyl)carbamic acid tert-butyl ester

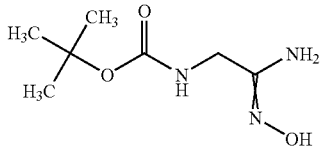

To a solution of N-(tert-butoxycarbonyl)-2-aminoacetonitrile (20.0 g) in absolute ethanol (200 ml) was added a solution of hydroxylamine (9.0 g) and potassium carbonate (17.6 g) in water (50 ml). The solution was heated to reflux for 2 days. The absolute ethanol was removed in vacuo and the aqueous residue extracted with ethyl acetate. The solvent was partially removed in vacuo until a precipitate formed. The suspension was cooled and filtered. The residue was washed with ethyl acetate to give the title compound as a white solid (12.84 g). Thermospray Mass Spectrum m/z 190 [MH$^+$].

Description 23: 5-Aminomethyl-[1,2,4]oxadiazole-3-carboxylic acid ethyl ester hydrochloride

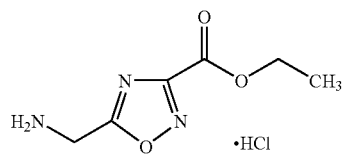

1,2,4-Oxadiazole-3-carboxylic acid, 5-[[[(1,1,dimethylethoxy)carbonyl]amino]methyl]ethyl ester (prepared as described in J. Org. Chem. (1995), 60 (10), 3112-20) (0.408 g) was dissolved in 4M hydrogen chloride in dioxane (10 ml), and the solution stirred at 20° C. for 0.75 h. The solvent was removed in vacuo to give the title compound as a light brown solid (0.347 g).

$^1$H NMR (D6 DMSO, 400 MHz) δ 1.32 (3H, t, J=7 Hz, CH$_3$), 4.42 (2H, q, J=7 Hz, CH$_2$), 4.58 (H, s, CH$_2$) and 9.04 (3H, br s, NH$_3^+$).

Description 24: [5-(5-Methyl-isoxazol-3-yl)-[1,2,4]oxadiazol-3-ylmethyl]carbamic acid tert-butyl ester

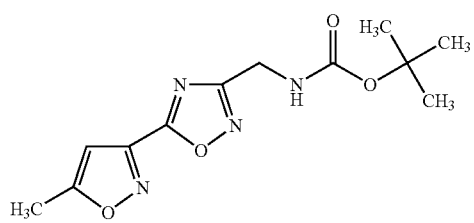

To a solution of Description 22 (0.373 g) and ethyl 5-methylisoxazole-3-carboxylate (0.305 g) in absolute ethanol (6 ml) was added sodium ethoxide (21% wt solution in ethanol, 0.186 ml). To the solution was added pre-dried 4A powdered molecular sieves (0.5 g). The suspension was heated under reflux for 2.5 h. The suspension was filtered and the residue washed with methanol (50 ml). The solvent was removed in vacuo. The residue was dissolved in dichloromethane (75 ml) and the solution was washed with 2N aqueous sodium hydroxide (25 ml), 2N hydrochloric acid (25 ml), and water (25 ml), dried (MgSO$_4$), and concentrated in vacuo to give the title compound as a white solid (0.250 g).

LC/MS R$_t$ 2.7 min m/z 298 [MNH$_4^+$].

Description 25: C-[5-(5-Methyl-isoxazol-3-yl)-[1,2,4]oxadiazol-3-yl]-methylamine hydrochloride

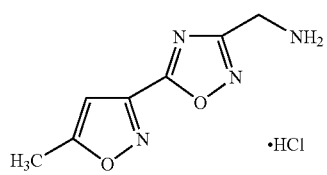

Description 24 was dissolved in 4M hydrogen chloride in dioxane (3 ml), and the solution stirred at 20° C. for 1.25 h. The solvent was removed in vacuo to give the title compound as a white solid (0.103 g).

Thermospray Mass Spectrum m/z 181 [MH$^+$].

Description 26: 3-(tert-Butoxycarbonylamino-methyl)-[1,2,4]oxadiazole-5-carboxylic acid ethyl ester

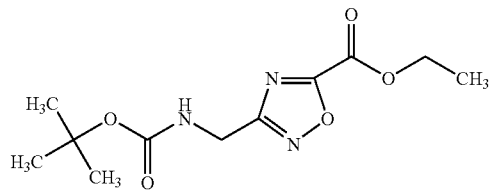

To a solution of Description 22 (1.0 g) in absolute ethanol (9 ml) and sodium ethoxide (21% wt solution in ethanol, 0.5 ml) was added diethyl oxalate (2.8 ml). Pre-dried 4A powdered molecular sieves (2 g) were added, and the suspension was heated under reflux for 3.5 h. The suspension was filtered and the residue washed with absolute ethanol (20 ml). The solvent was removed in vacuo. The residue was dissolved in dichloromethane (75 ml) and the solution was washed with saturated aqueous sodium hydrogen carbonate (25 ml), 2N hydrochloric acid (25 ml), and water (25 ml), dried (MgSO$_4$), and concentrated in vacuo to give the title compound as a white solid (0.418 g). LC/MS R$_t$ 2.65 min m/z 289 [MNH$_4^+$].

Description 27: 3-Aminomethyl-[1,2,4]oxadiazole-5-carboxylic acid ethyl ester hydrochloride

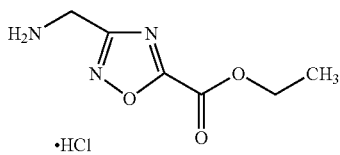

Description 26 was dissolved in 4M hydrogen chloride in dioxane (6 ml), and the solution stirred at 20° C. for 1.25 h. The solvent was removed in vacuo to give the title compound as a colourless gum (0.251 g).

$^1$H NMR (D6 DMSO, 400 MHz) δ 1.34 (3H, t, J=6 Hz, CH$_3$), 4.37 (2H, s, CH$_2$), 4.45 (2H, q, J=6 Hz, CH$_2$) and 8.84 (3H, br s, NH$_3^+$).

Description 28: 3-Aminomethyl-[1,2,4]oxadiazole-5-carboxylic acid ethylamide

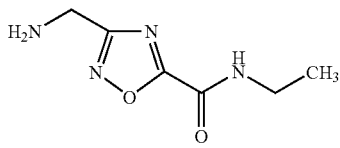

To a solution of Description 27 (0.051 g) in absolute ethanol (5 ml) was added ethylamine hydrochloride (0.2 g) and N,N-diisopropylethylamine (0.44 ml). The solution was stirred at room temperature for 3 h in a sealed vial (Reactivial™). The solution was equally applied onto sulphonic acid ion exchange cartridges (2×10 g Isolute SCX, pre-treated with methanol). The cartridges were eluted with methanol followed by 10% 0.880 ammonia in methanol, and the basic fractions were evaporated in vacuo to give the title compound (0.037 g).

$^1$H NMR (D6 DMSO, 400 MHz) δ 1.10 (3H, t, J=6 Hz, CH$_3$), 3.25 (2H obscured by solvent, q, J=6 Hz, CH$_2$), 3.87 (2H, s, CH$_2$) and 9.41 (3H, br s, NH$_3^+$).

Description 29: (1-Methyl-pyrazole-3-carboxamide) [CAS No. 89179-62-4]

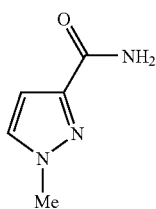

A solution of 1-H-pyrazole-3-carboxamide [CAS No: 33064-36-7] (0.1 g) in tetrahydrofuran (10 ml) and N,N-dimethylformamide (5 ml) was treated with potassium carbonate (0.12 g) and methyl iodide (0.062 ml), and the mixture was stirred at room temperature for 3 days. The mixture was diluted with water (50 ml) and extracted with ethyl acetate (3×20 ml). The aqueous layer was evaporated in vacuo and the solid was triturated with ethyl acetate; the extracts were concentrated in vacuo to give the title compound (0.08 g) as a colourless oil containing ca. 10% unreacted starting material (1-H-pyrazole-3-carboxamide).

LC-MS: Rt=0.7 min. Mass Spectrum m/z 126 [MH$^+$].

Description 30: (1-Methyl-pyrazole-3-methanamine)

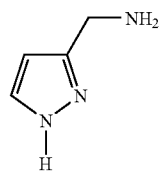

A solution of Description 29 (0.08 g) in anhydrous tetrahydrofuran (5 ml) was treated with a 1M solution of borane/tetrahydrofuran complex in tetrahydrofuran (3.5 ml) and the mixture was heated at 65° C. for 18 hrs. On cooling the mixture was cautiously quenched by dropwise addition of methanol followed by 2N hydrochloric acid. The solvents were removed by evaporation, and the residue was made basic with triethylamine and concentrated in vacuo. The mixture was dissolved in a small volume of methanol applied onto a sulphonic acid SCX ion exchange cartridge (10 g), eluting with methanol followed by 10% 0.880 ammonia in methanol. The basic fraction was evaporated in vacuo to give the title compound (0.054 g) as a colourless oil which also contained ~10% of 1H-pyrazole-3-methanamine [CAS No. 37599-58-9].

1H nmr (D$_4$MeOH), δ 3.84 (2H, s, CH$_2$); 3.86 (3H, s, Me); 6.28 (1H, m, Ar); 7.53 (1H, m, Ar).

Description 31: (5-Methyl-pyrazole-3-methanamine)

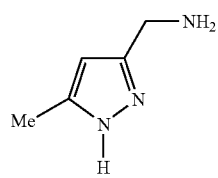

Description 31 was prepared in a similar manner to Description 30 from 5-methyl-pyrazole-3-carboxamide [CAS No. 4027-56-9] (0.09 g) to give the title compound (0.035 g) as a white solid.

$^1$H nmr (D4 MeOH), δ: 2.08 (3H, s, Me); 3.70 (2H, s, CH$_2$); 5.9 (1H, m, Ar).

Description 32:
5-Aminomethyl-isoxazole-3-carboxylic acid ethyl ester

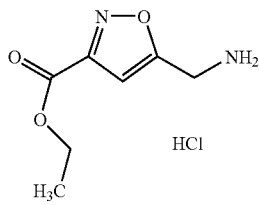

To a stirred solution of 5-(tert-butoxycarbonylaminomethyl)-isoxazole-3-carboxylic acid ethyl ester (1.954 g) (EP 0451790) in ethanol (15 ml) was added a solution of 4.0M hydrogen chloride in 1,4-dioxane (23 ml). The mixture was stirred at 20° C. for 22 h and the solvent evaporated in vacuo to give the title compound (1.128 g) as a pale brown solid.

$^1$H nmr (400 MHz, D6 DMSO) 8.86 δ (3H, br.s, NH$_3^+$) 7.056 (1H, s, CH) 4.41-4.336 (4H, q+br.q, 2×CH$_2$) 1.32 δ (3H, t, CH$_3$)

Description 33:
5-Diallylaminomethyl-furan-3-carboxylic acid ethyl ester

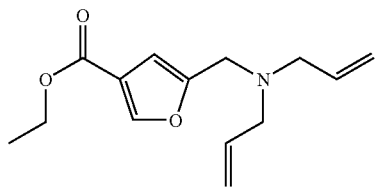

To a solution of 5-formyl-3-furancarboxylic acid ethyl ester (prepared as described in Tetrahedron (1996), 52(12), 4245-56) (1.61 g) in dichloromethane (20 ml) was added diallylamine (1.18 ml). The solution was treated with glacial acetic acid (0.55 ml) and then sodium triacetoxyborohydride (4.2 g). The suspension was stirred at room temperature for 3.5 h. The suspension was treated with ethanol (80 ml) and stirred at room temperature for 25 mins. The solvent was removed in vacuo. The residue was partitioned between ethyl acetate (200 ml) and saturated aqueous sodium hydrogen carbonate (100 ml). The phases were separated and the organic phase washed with saturated aqueous sodium hydrogen carbonate (100 ml) and brine (50 ml). The combined aqueous phases were extracted with ethyl acetate (50 ml). The combined organic extracts were dried (MgSO$_4$), filtered and the solvent removed in vacuo. The residue was dissolved in methanol and applied equally onto SCX sulphonic acid ion exchange cartridges (10 g×4, pre-treated with methanol). The cartridges were eluted with methanol followed by 10% 0.880 ammonia in methanol; evaporation of the basic fractions in vacuo gave the title compound as a mobile oil (2.06 g).

LC/MS R$_t$ 1.76 min m/z 250 [MH$^+$].

Description 34: 5-Aminomethyl-furan-3-carboxylic acid ethyl ester

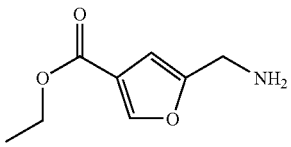

To a solution of Description 33 in dichloromethane (15 ml) was added N,N-dimethylbarbituric acid (4.49 g). To the suspension was added palladium tetrakis(triphenylphosphine) (0.130 g). The mixture was heated to 35° C. under nitrogen for 4 h. A further amount of palladium tetrakis(triphenylphosphine) (0.150 g) was added and the mixture heated for a further 2 h. The mixture was applied equally onto SCX sulphonic acid ion exchange cartridges (10 g×6, pre-treated with methanol). The cartridges were eluted with methanol followed by 10% 0.880 ammonia in methanol; evaporation of the basic fractions in vacuo gave an orange oil. Purification of the residue by Biotage flash chromatography on a 40 g silica gel cartridge, eluting with 5% methanol in chloroform gave the title compound a yellow oil (0.573 g).

Thermospray Mass Spectrum m/z 170 [MH$^+$]

Description 35: (5-Ethylcarbamoyl-[1,3,4]oxadiazol-2-ylmethyl)-carbamic acid tert-butyl ester

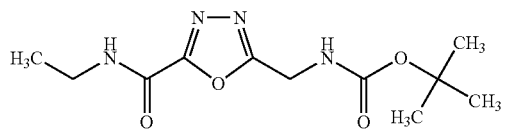

To a solution of 5-[[[(1,1-dimethylethoxy)carbonyl]amino]methyl]-1,3,4-oxadiazole-2-carboxylic acid ethyl ester (prepared as described in JOC (1995), 60(10), 3112-20) (0.150 g) in methanol (5 ml) was added a solution of 2.0M ethylamine in tetrahydrofuran (3 ml). The solution was left standing at 20° C. for 1.5 h. The solvent was removed by evaporation using a stream of nitrogen to give the title compound as a yellow gum (0.139 g).

LC/MS R$_t$ 2.13 min m/z 288 [MNH$_4^+$].

Description 36:
5-Aminomethyl-[1,3,4]oxadiazole-2-carboxylic acid ethylamide hydrochloride

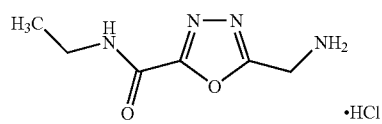

Description 35 (0.133 g) was dissolved in 4M hydrogen chloride in dioxane (5 ml). The solution was left standing at 20° C. for 40 mins. The solvent was removed by evaporation using a stream of nitrogen to give the title compound (0.113 g).

Thermospray Mass Spectrum m/z 188 [MNH$_4^+$]

Description 37: 2-(5-Methyl-[1,3,4]oxadiazol-2-yl)ethylamine hydrochloride

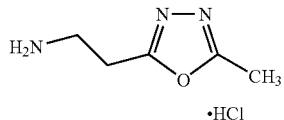

Description 38 was dissolved in 4M hydrogen chloride in dioxane (5 ml). The solution was stirrer at 20° C. for 1 h. The solvent was removed in vacuo to give the title compound as a brown gum (0.348 g).

$^1$H NMR (D6 DMSO, 400 MHz) δ 2.60 (3H, s), 3.20 (4H, m), 8.33 (3H, br s).

Description 38: [2-(5-Methyl-[1,3,4]oxadiazol-2-yl)ethyl]carbamic acid tert-butyl ester

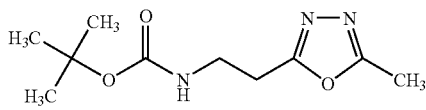

To a solution of Description 39 (0.8 g) in pyridine (8 ml) at 0° C. was added thionyl chloride (0.36 ml). The resulting suspension was stirred at 0° C. for 5 mins and then allowed to warm to 20 C over 8 h. A portion of the mixture (6 ml) was heated to 120° C. for 15-20 mins. The solvent was removed in vacuo and the residue purified by silica SPE (10 g) eluting with 4:1 to 0:1 cyclohexane to ethyl acetate to give the title compound as a brown oil (0.387 g).

LC/MS: $R_t$ 2.26 min m/z 228 [MH$^+$].

Description 39: [3-(N'-Acetyl-hydrazino)-3-oxo-propyl]carbamic acid tert-butyl ester

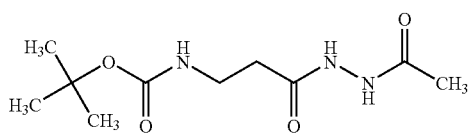

To a suspension of 1,1-carbonyldiimidazole (2.825 g) in anhydrous tetrahydrofuran (20 ml) at 0° C. was added N-tert-butoxycarbonyl-beta-alanine (3.379 g) portionwise over 5 mins. The suspension was allowed to warm to 20 C and stirred for 15 mins. To the resulting solution was added acetic hydrazide (1.32 g). The mixture was stirred at 20 C for 5 h. The solvent was removed in vacuo and the residue purified by biotage (90 g) eluting with ethyl acetate to 5% methanol in chloroform to give the title compound as a white solid (1.435 g).

LC/MS: $R_t$ 1.85 min m/z 246 [MH$^+$].

Description 40: 1-(5-Chloromethyl-[1,3,4]oxadiazol-2-ylmethyl)-3-[(2S)-4-(3,4-dichlorobenzyl)morpholin-2-ylmethyl]urea

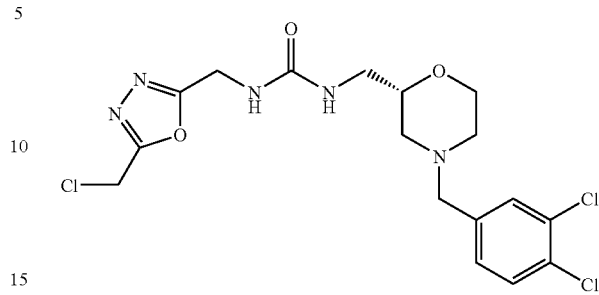

A mixture of chloroacetic anhydride (0.488 g) and Example 31 (0.149 g) was heated at 85° C. with an air condenser for 5 h, then left to stand at 20° C. for 18 h. The brown solid was dissolved in ethyl acetate and purified using a silica SPE cartridge (20 g) which was eluted successively with ethyl acetate (200 ml), acetonitrile (200 ml) and acetone (400 ml). The acetone fractions were concentrated in vacuo to give the title compound (0.061 g) as a brown gum.

LC/MS: $R_t$ 2.27 min
Mass spectrum m/z 448 [MH$^+$].

Description 41: 1-[4-(3,4-Dichloro-benzyl)morpholin-2-ylmethyl]-3-(4-hydrazinocarbonyl-furan-2-ylmethyl)urea hydrochloride

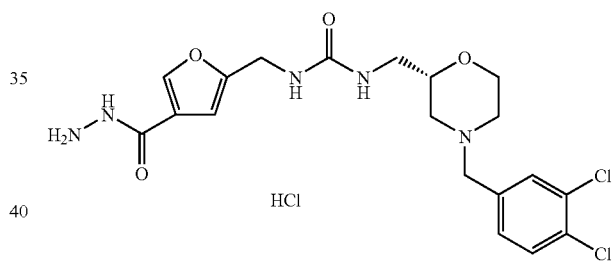

To Description 42 (0.789 g) was added 4.0M hydrochloric acid in dioxane (20 ml). To the suspension was added methanol (20 ml). The solution was stirred at 20 C for 3 h. The solvent was removed in vacuo to give the title compound as a white solid (0.97 g).

LC/MS $R_t$ 2.20 min m/z 456 [MH$^+$]

Description 42: N'-(5-{3-[4-(3,4-Dichloro-benzyl)morpholin-2-ylmethyl]ureidomethyl}furan-3-carbonyl)hydrazinecarboxylic acid tert-butyl ester

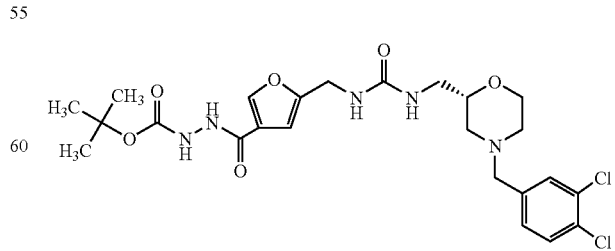

To a solution of Example 85 (0.777 g) in N,N-dimethylformamide (8 ml) was added 1-hydroxybenzotriazole (0.237 g), diisopropylethylamine (0.255 ml) and 1-(3-dimethylaminopropyl)-3-ethylcarbodiimide (0.422 g), The solution was stirred at 20° C. for 5-10 min and then treated with t-butylcarbazide (0.233 g). The solution was stirred at 20° C. for 24 h. The mixture was applied equally onto sulphonic acid ion exchange cartridges (10 g×3 Isolute SCX, pretreated with methanol). The cartridges were eluted with methanol followed by 10% 0.880 ammonia methanol. The solvent was removed in vacuo from the basic fractions. The residue was further purified by silca SPE (10 g×2) eluting sequentially with 2:1 cyclohexane:ethyl acetate, ethyl acetate, 20:1 chloroform:methanol to give the title compound as a white solid (0.789 g).

LC/MS $R_t$ 2.54 min m/z 556 [MH$^+$]

Description 43: 1-[4-(N'-Formyl-hydrazinocarbonyl)furan-2-ylmethyl]-3-[(2S)-4-(3,4-dichloro-benzyl)morpholin-2-ylmethyl]urea

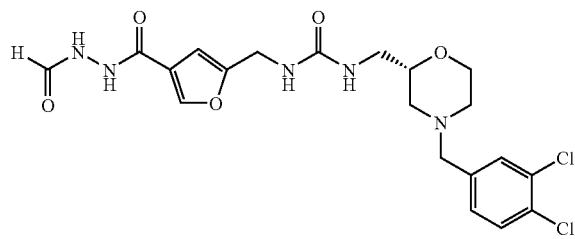

To a solution of Example 85 (0.110 g) in N,N-dimethylformamide (2 ml) was added 1-hydroxybenzotriazole (0.031 g), N,N-diisopropylethylamine (0.04 ml) and 1-(3-dimethylaminopropyl)-3-ethylcarbodiimide hydrochloride (0.044 g). The solution was stirred at 20° C. for 2-3 min and then treated with formylhydrazine (25 mg). The solution was allowed to stand at 20° C. for 7 days. The mixture was applied onto sulphonic acid ion exchange (10 g, Isolute SCX, pretreated with methanol) and the cartridge was eluted with methanol followed by 10% 0.880 ammonia in methanol. The solvent was removed from the basic fraction in vacuo to give the title compound (0.123 g).

LC/MS: $R_t$ 2.08 min m/z 484 [MH$^+$].

Description 44: 5-Aminomethylthiophene-3-carboxylic acid methylamide

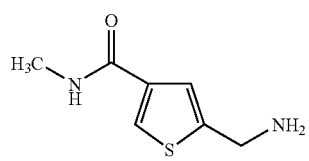

To a solution of Description 45 (0.366 g) in methanol (8 ml) was added 2M aqueous sodium hydroxide (4 ml). The solution was allowed to stand at 20° C. for 3 h. The solution was neutralised to pH7 using 2M aqueous hydrochloric acid. The neutralised solution was applied to sulphonic acid ion exchange (10 g×3, isolute SCX, pretreated with methanol) and the cartridges were eluted with methanol followed by 10% 0.880 ammonia in methanol. The solvent was removed from the basic fraction in vacuo to give the title compound (0.232 g).

$^1$H NMR (D6 DMSO, 400 MHz) δ 2.75 (3H, d, J=4 Hz), 3.85 (2H, s), 7.3 (1H, s), 7.85 (1H, s), 8.2 (1H, q, J=4 Hz).

Description 45: 5-[(2,2,2-Trifluoroacetylamino)methyl]-thiophene-3-carboxylic acid methylamide

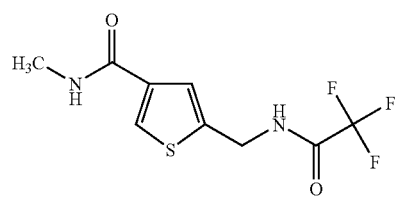

To suspension of N-methyl-3-thiophenecarboxamide (1.12 g) (prepared according to J. Org. Chem. (1976), 41(23), 3668-74) in concentrated aqueous sulphuric acid (25 ml) at 0-5° C. was added N-(hydroxymethyl)trifluoroacetamide (1.134 g). The suspension was allowed to warm to 20° C. and stirred for 2 h. The mixture was poured onto ice (150 g) and diluted with ethyl acetate (200 ml). The biphase mixture was diluted with saturated sodium hydrogen carbonate (200 ml) and treated with sodium hydrogen carbonate (21 g). The phases were separated and the organic phase washed with saturated sodium hydrogen carbonate (150 ml×2). The combined aqueous phases were extracted with ethyl acetate (100 ml). The combined organic extracts were concentrated in vacuo. The residue was pre-absorbed onto silica and purified by biotage (90 g) eluting with 1:1 to 0:1 cyclohexane:ethyl acetate to give the title compound as a white solid (0.7129).

LC/MS: $R_t$ 2.32 min, m/z 267 [MH$^+$].

Description 46: 2-Aminomethyloxazole-4-carboxylic acid methyl ester

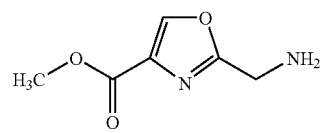

2-(Benzyloxycarbonylaminomethyl)oxazole-4-carboxylic acid methyl ester (0.439 g) (prepared as described in; Journal of Peptide Science (1999), 5(9), 392-398) was dissolved in ethyl acetate (13 ml) and hydrogenated with vigorous stirring at 20° C. and 1 atmosphere of pressure using 10% palladium on carbon catalyst (0.20 g) for 4 hours. The mixture was filtered using celite filter aid and the solvent evaporated from the filtrate in vacuo to give the title compound as a yellow solid (0.197 g)

$^1$H NMR (CDCl$_3$, 400 MHz) δ 8.20 (1H, s), 4.01 (2H, s), 3.92 (3H, s), 1.71 (2H br s)

Description 47: 5-Aminomethyl-furan-3-carboxylic acid methylamide methylamide

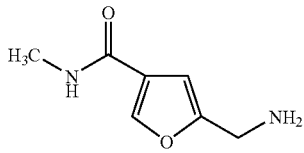

To a solution of Description 48 (0.22 g) in methanol (5 ml) was added 2M aqueous sodium hydroxide (2.5 ml) at 20° C. The solution was allowed to stand at 20° C. for 2.5 h. The solution was acidified using 2M aqueous hydrochloric acid (ca 2 ml) and the mixture applied equally to sulphonic acid ion exchange cartridges (10 g×2 Isolute SCX, pretreated with methanol). The cartridges were eluted with methanol followed by 10% 0.880 ammonia in methanol and evaporation in vacuo of the basic fractions gave the title compound as a yellow oil (0.116 g).

$^1$H NMR (D6 DMSO, 400 MHz) δ 2.70 (3H, d, J=5 Hz), 3.65 (2H, s), 6.5 (1H, s), 8.0 (1H, s), 8.1 (1H, m).

Description 48: 5-[(2,2,2-Trifluoro-acetylamino)methyl]furan-3-carboxylic acid methylamide

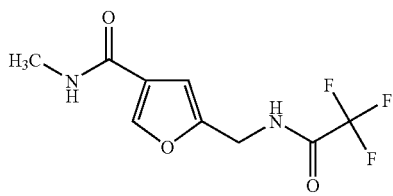

To a suspension of N-methyl-3-furancaboxamide (0.404 g) (prepared as described in Synthetic Communications (1992), 22(16), 2381-92) in concentrated aqueous sulphuric acid (10 ml) at 0-5° C. was added N-(hydroxymethyl)-trifluoroacetamide (0.483 g). The suspension was allowed to warm to 20° C. and stirred for 1 h. The mixture was poured onto ice (100 g) and diluted with ethyl acetate (150 ml). The phases were separated and the organic phase washed with saturated sodium hydrogen carbonate (50 ml×2), brine (30 ml), dried (MgSO$_4$) and filtered. The solvent was removed in vacuo to give a yellow solid. The residue was purified by silica SPE (10 g) eluting with 4:1 to 1:3 cyclohexane:ethyl acetate to give the title compound as a white solid (0.286 g).

LC/MS Rt 1.9 min m/z 251 [MH$^+$]

Description 49: (5-Methylcarbamoyl-[1,3,4]oxadiazol-2-ylmethyl)carbamic acid tert-butyl ester

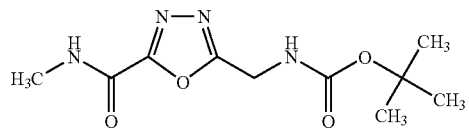

Prepared in an analogous fashion to Description 35 from 5-[[[(1,1-dimethylethoxy)carbonyl]amino]methyl]-1,3,4-oxadiazole-2-carboxylic acid ethyl ester (prepared as described in JOC (1995), 60(10), 3112-20) (0.150 g) using 2.0M methylamine in THF.

LC/MS R$_t$ 2.01 min m/z 257 [MH$_4$].

Description 50: 5-Aminomethyl-[1,3,4]oxadiazole-2-carboxylic acid methylamide hydrochloride

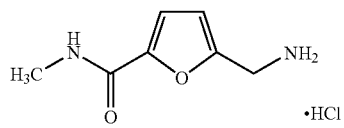

Prepared in an analogous fashion to Description 36 from Description 49.

$^1$H NMR (D6 DMSO, 400 MHz) δ 9.37 (1H, s), 8.99 (3H, br s), 4.48 (2H, s), 2.81 (3H, d)

Description 51: {(2S)-4-[1-(3,4-Difluorophenyl)ethyl]morpholin-2-ylmethyl}carbamic acid 4-nitrophenyl ester Isomer I, and Description 52: {(2S)-4-[1-(3,4-Difluorophenyl)ethyl]morpholin-2-ylmethyl}carbamic acid 4-nitro-phenyl ester Isomer II

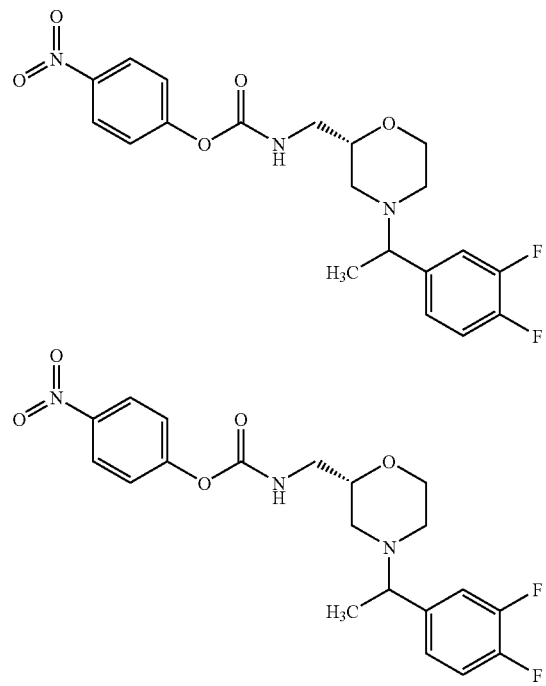

Prepared in similar fashion to 4-nitrophenyl {(2S)-4-[1-(3,4-dichlorophenyl)ethyl]morpholin-2-yl}methylcarbamate Isomers I and II (as described in WO 02/26723) from Description 53.

Description 51; LC/MS R$_t$ 2.56 min m/z 422 [MH$^+$]
Description 52; LC/MS R$_t$ 2.55 min m/z 422 [MH$^+$]

Description 53: C-[(2S)-4-[1-(3,4-Difluorophenyl)ethyl]-morpholin-2-yl]methylamine dihydrochloride

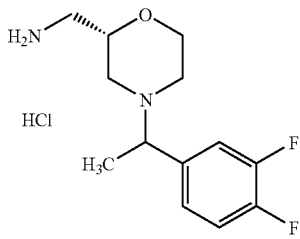

Prepared in similar fashion to 1-{(2S)-4-[1-(3,4-Dichlorophenyl)ethyl]morpholin-2-yl}methanamine dihydrochloride (as described in WO 02126723) from Description 54.
Thermospray MS m/z 357 [MH⁺]

Description 54: {(2S)-4-[1-(3,4-Difluoro-phenyl)-ethyl]-morpholin-2-ylmethyl}-carbamic acid tert-butyl ester

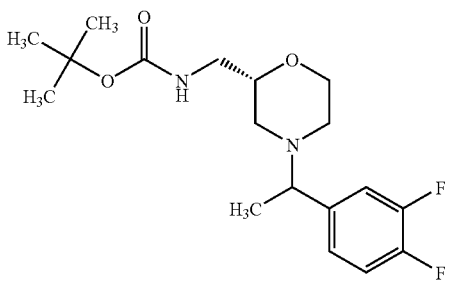

Prepared in similar fashion to tert-Butyl {(2S)-4-[1-(3,4-dichlorophenyl)ethyl]morpholin-2-yl}methylcarbamate (as described in WO 02/026723) using (+)-4-(1-bromoethyl)-1,2-difluorobenzene.
LC/MS $R_t$ 2.41 min m/z 357 [MH⁺]

Description 55:
2-(5-Trifluoromethyl-tetrazol-2-yl)ethylamine hydrochloride

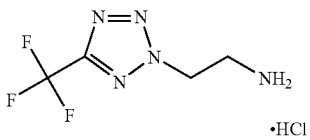

A solution of 2-bromoethylphthalimide (2.5 g) and 5-(trifluoromethyl)tetrazole sodium salt (1.6 g) (for preparation see Inorganic Chemistry, (1989), 28(5), 893-7) in dry DMF (35 ml) was stirred at 100° C. for 16 hours. The solution was poured onto ice and the white precipitate filtered, dried and recrystallised from ethanol/water to give 2-[2-(5-Trifluoromethyl-tetrazol-2-yl)-ethyl]-isoindole-1,3-dione (1.9 g).

Melting point 98-99.5° C.

A solution of 2-[2-(5-trifluoromethyl-tetrazol-2-yl)-ethyl]-isoindole-1,3-dione (1.9 g) and hydrazine hydrate (0.28 ml) in ethanol (50 ml) was refluxed for 15 hours and then evaporated to dryness. The residue was heated in 2N HCl (50 ml) for 1 hour, cooled, filtered and the filtrate evaporated to yield a yellow solid which was recrystallised from ethyl acetate/diethyl ether to give the title compound (0.90 g). C:H:N analysis; found; C, 22.25; H, 3.42; N, 30.91; expected. C, 22.08; H, 3.24; N, 32.19.
Melting point 145-149° C.

Description 56:
C-(3-Methyl-3H-imidazol-4-yl)-methylamine

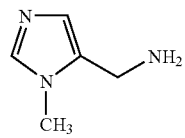

3-Methyl-3H-imidazole-4-carboxylic acid amide (17 g) (for preparation see JP 61178968, CAN 106:33054) was placed in a pressure-equalizing funnel with a plug of cotton wool at the bottom of it, and was continually extracted into a suspension of lithium aluminium hydride (8 g) in tetrahydrofuran (500 ml) for 20 hours. A mixture of water (15 ml) and tetrahydrofuran (50 ml) was carefully added to the funnel. The resulting precipitate was filtered and the filtrate concentrated in vacuo. The residual oil was purified by distillation to yield the title compound (10.6 g).
Boiling point 118° C./0.3 mbar.

EXAMPLES

Synthetic Method A

Example 16: 1-[(2S)-4-(3,4-Dichloro-benzyl)morpholin-2-ylmethyl]-3-(5-methyl-[1,3,4]oxadiazol-2-ylmethyl)urea

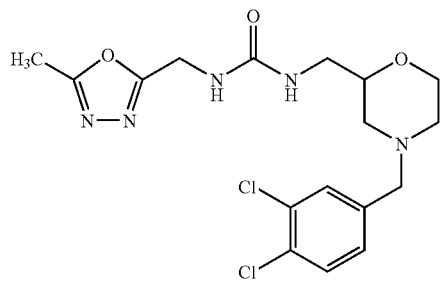

To a solution of 5-methyl-1,3,4-oxadiazole-2-methanamine (prepared as described in Patent DE 3801404) (0.050 g) in anhydrous N,N-dimethylformamide (3 ml) was added N,N-diisopropylethylamine (0.116 ml) and Description 9 (0.147 g). The solution was stirred at room temperature for 24 h. The solution was applied onto a sulphonic acid ion exchange cartridge (10 g Isolute SCX, pre-treated with methanol). The cartridge was eluted with methanol followed by 10% 0.880 ammonia in methanol; evaporation of the basic fraction in vacuo gave an oil. Purification of the residue by Biotage flash chromatography on silica gel, eluting with 100:8:1 dichloromethane/ethanol/0.880 ammonia solution, gave a yellow oil. The residue was dissolved in ethyl acetate (50 ml) and the solution was washed with 2N aqueous sodium hydroxide (3×20 ml), dried (MgSO$_4$) and concentrated in vacuo to give the title compound as a colourless oil (0.094 g).

LC/MS R$_t$ 2.08 min m/z 414 [MH$^+$].

Synthetic Method B (Interconversion)

Example 9: 5-{3-[(2S)-4-(3,4-Dichloro-benzyl)morpholin-2-ylmethyl]ureidomethyl}-[1,2,4]oxadiazole-3-carboxylic acid ethylamide

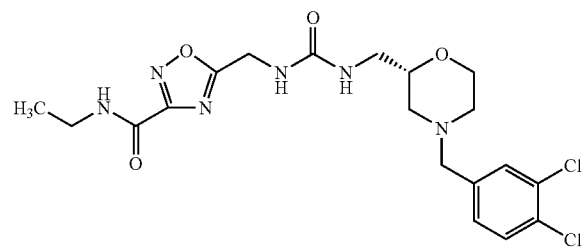

To a solution of Example 7 (0.040 g) in absolute ethanol (0.7 ml) was added ethylamine hydrochloride (0.069 g) and then N,N-diisopropylethylamine (0.147 ml). The suspension was stirred at room temperature for 18 h in a sealed vial. The solvent was removed in vacuo. The residue was dissolved in methanol and applied onto a sulphonic acid ion exchange cartridge (5 g Isolute SCX, pre-treated with methanol). The cartridge was eluted with methanol followed by 10% 0.880 ammonia in methanol; evaporation of the basic fraction in vacuo gave the title compound (0.038 g) as a white solid.

LC/MS R$_t$ 2.29 min m/z 471 [MH$^+$].

Synthetic Method C (Interconversion)

Example 1 [1-[(2S)-4-(3,4-Dichloro-benzyl)morpholin-2-ylmethyl]-3-(2-isopropyl-2H-tetrazol-5-ylmethyl)urea] and Example 30 [1-[(2S)-4-(3,4-Dichloro-benzyl)morpholin-2-ylmethyl]-3-(1-isopropyl-1H-tetrazol-5-ylmethyl)urea]

Example 1

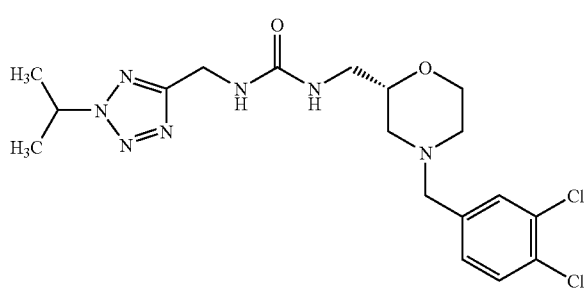

Example 30

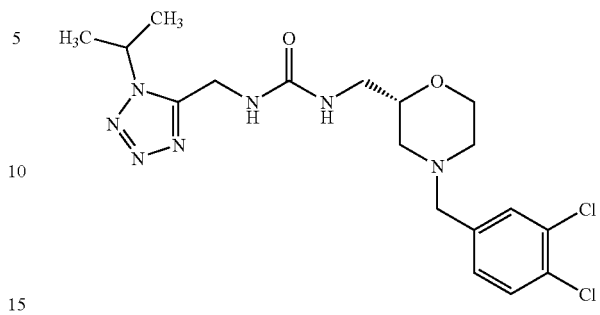

To a stirred solution of Example 31 (0.050 g) in N,N-dimethylformamide (6 ml) was added potassium carbonate (0.040 g) followed by 2-iodopropane (0.0138 ml). The mixture was stirred at 22° C. for 18 h before being applied to a 2 g SCX ion-exchange cartridge (pre-conditioned with methanol). The cartridge was eluted with methanol, followed by 10% 0.880 ammonia solution in methanol. The first ammonia fraction was evaporated in vacuo and the residue further purified by Biotage™ flash chromatography on silica gel, eluting with 150:8:1 dichloromethane/ethanol/0.880 ammonia solution. The fractions of the first eluting product were combined and the solvent evaporated in vacuo to give the title compound (Example 1) (0.0307 g) as a colourless glass.

LC/MS: R$_t$=2.33 min, m/z 442,444 [MH$^+$]

The fractions of the second eluting product were combined and the solvent evaporated in vacuo to give the title compound (Example 30) (0.0079 g) as a colourless glass.

LC/MS: R$_t$=2.31 min, m/z 442,444 [MH$^+$]

Synthetic Method D

Example 41: 5-{3-[(2S)-4-(3,4-Dichloro-benzyl)morpholin-2-ylmethyl]ureidomethyl}furan-2-carboxylic acid triethylamine salt (interconversion)

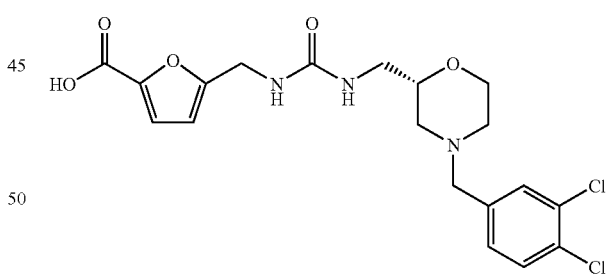
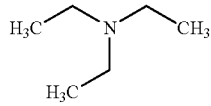

To a solution of Example 42 (0.208 g) in methanol (5.5 ml) was added 2N sodium hydroxide (1 ml). The solution was stirred at 20° C. for 1.5 h. A further amount of 2N sodium hydroxide (1 ml) was added and the solution stirred for a further 2 h at 200. The solvent was removed in vacuo. The residue was dissolved in water (5 ml) and acidified to pH1 using 2N hydrochloric acid. The suspension was applied onto a sulphonic acid ion exchange cartridge (10 g Isolute SCX, pre-treated with water). The cartridge was eluted with water followed by 10% triethylamine in methanol; evaporation of the basic fraction in vacuo gave the title compound as a colourless glass (0.195 g).

LC/MS $R_t$ 2.13 min m/z 442 [MH$^+$].

Example 44: 5-{3-[(2S)-4-(3,4-Dichloro-benzyl)morpholin-2-ylmethyl]ureidomethyl}furan-2-carboxylic acid ethylamide

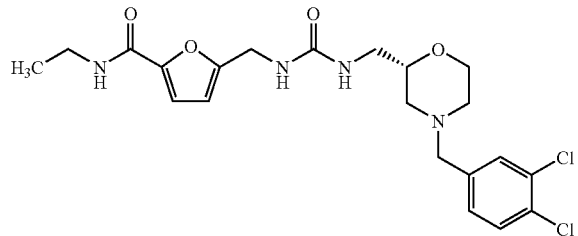

To a solution of Example 41 in N,N-dimethylformamide (2 ml) was added 1-hydroxybenzotriazole (0.0159), and ethylamine hydrochloride (0.042 g). To the suspension was added N,N-diisopropylethylamine (0.09 ml) and then 1-(3-dimethylaminopropyl)-3-ethylcarbodiimide hydrochloride (0.02 g). After stirring at room temperature for 16 h, further amounts of 1-(3-dimethylaminopropyl)-3-ethylcarbodiimide hydrochloride (0.030 g), ethylamine hydrochloride (0.02 g) and N,N-diisopropylethylamine (0.09 ml) were added. The mixture was stirred for a further 3 h at room temperature. The mixture was partitioned between ethyl acetate (60 ml) and 2N sodium hydroxide (20 ml) The phases were separated and the organic phase washed with 2N sodium hydroxide (20 ml) and water (20 ml), dried (MgSO$_4$), and filtered. The solvent was removed in vacuo. The residue was dissolved in methanol and applied onto a sulphonic acid ion exchange cartridge (1 g Isolute SCX, pre-treated with methanol). The cartridge was eluted with methanol followed by 10% 0.880 ammonia in methanol. The solvent was removed from the basic fraction by evaporation under a stream of nitrogen. The residue was purified by mass directed preparative HPLC to give the title compound as a colourless gum (0.0064 g).

LC/MS $R_t$ 2.15 min m/z 469 [MH$^+$].

Synthetic Method E (Interconversion)

Example 146: 1-(1-Acetyl-1H-pyrazol-3-ylmethyl)-3-[(2S)-4-(3,4-dichloro-benzyl)morpholin-2-ylmethyl]urea

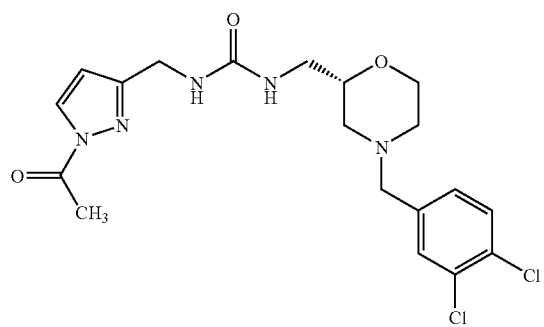

To a solution of Example 47 (10 mg) in 4:1 acetonitrile:N,N-dimethylformamide (0.3 ml) was added pyridine (0.1 ml) and acetic anhydride (0.024 ml), and the mixture was stirred at room temperature under nitrogen for 18 h. The mixture was partitioned between 10% aqueous citric acid (5 ml) and chloroform (5 ml), and the organic layer was evaporated to give a colourless gum (4.6 mg). Purification by mass directed preparative HPLC gave the title compound as a gum (2.29 mg).

LC/MS $R_t$ 2.24 min, m/z 440 [MH$^+$]

Synthetic Method F

Example 165: 1-[4-(3,4-Dichlorobenzyl)morpholin-2-ylmethyl]-3-(2-furan-2-yl-ethyl)urea A suspension of 4-{[(polystyrene resin)methyl]thio}phenyl 4-nitrophenyl carbonate (Prepared as described in Tetrahedron Lett. (1998), 39(22), 3631-3634, 1.5 g @ 0.99 mmol/g) in N,N-dimethylformamide (15 ml) was shaken with Description 3 (0.80 g) at 22° C. for 1 h. The resin was filtered, washed with N,N-dimethylformamide (×2), dichloromethane (×3) and N,N-dimethylformamide. The resin was again shaken with N,N-dimethylformamide (15 ml) and Description 3 (0.80 g) at 22° C. for 1 h before being filtered, washed with N,N-dimethylformamide (×2), dichloromethane (×3) and ether (×2) and dried in vacuo to give the intermediate resin 4-{[(polystyrene resin)methyl]thio}phenyl [4-(3,4-dichlorobenzyl)morpholin-2-yl]methylcarbamate as orange beads. To a sample of this resin (50 mg) in a test tube was added 2-furan-2-yl-ethylamine (0.0112 g) and 1 drop of 1-methyl-2-pyrrolidinone, and the mixture was placed into a microwave oven and heated at full power (600 W) for 5 min. Dichloromethane (2 ml) and formylpolystyrene resin were added, and the mixture was shaken at 22° C. for 18 h. The suspension was poured onto a 1 g solid phase extraction (Isolute SCX sulphonic acid) column which was then washed with methanol before eluting with 10% 0.880 ammonia solution in methanol. The basic fraction was evaporated in vacuo to give a cream solid which was further purified by eluting through a 1 g silica solid phase extraction cartridge (Varian Bondelut) eluting sequentially with dichloromethane, ether, ethyl acetate, acetone, acetonitrile and methanol, to give the title compound as a pale yellow glass (0.0052 g).

LC/MS $R_t$ 2.42 min, Mass Spectrum m/z 412 [MH$^+$].

Synthetic Method G (Interconversion)

Example 101: 1-(2-tert-Butyl-2H-tetrazol-5-ylmethyl)-3-[(2S)-4-(3,4-dichlorobenzyl)morpholin-2-ylmethyl]urea To a stirred solution of Example 31 (0.05 g) in trifluoroacetic acid (1 ml) was added tert-butyl alcohol (0.019 g) and conc. sulphuric acid (0.05 ml). The mixture was stirred at 22°

C. for 16 h before water (1 ml) was added and the mixture basified by addition of 2M sodium hydroxide solution. Dichloromethane (5 ml) was added with vigorous stirring and the mixture was separated using a hydrophibic fritted cartridge before the organic phase being applied to a 2 g SCX ion-exchange cartridge (pre-conditioned with methanol). The cartridge was eluted with methanol, followed by 10% 0.880 ammonia solution in methanol. The first ammonia fraction was evaporated in vacuo and the residue further purified by passing through an SPE cartridge (2 g, Si), eluting with an series of solvents; dichloromethane (2 vols), chloroform (2 vols), ether (2 vols), ethyl acetate (2 vols), acetonitrile, (2 vols) acetone (2 vols), and methanol (2 vols). The acetone fractions were combined and the solvent evaporated in vacuo to give the title compound (0.0164 g) as a colourless glass.

LC/MS: $R_t$=2.35 min, m/z 456 [MH$^+$]

Synthetic Method H (Interconversion)

Example 139: 1-[(2S)-4-(3,4-Dichloro-benzyl)morpholin-2-ylmethyl]-3-(5-trifluoromethyl-[1,3,4]oxadiazol-2-ylmethyl)urea

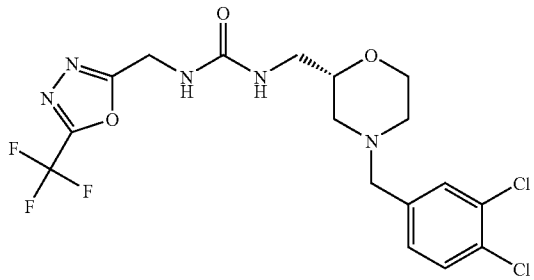

A suspension of Example 31 (0.050 g) in anhydrous chloroform (0.5 ml) under nitrogen was treated with trifluoroacetic anhydride (0.044 ml), and the mixture stirred at 20° C. for 3 h. A further portion of trifluoroacetic anhydride (0.018 ml) was added and stirring continued for a further 50 minutes at 20° C., after which time the solution was blown down to dryness and azeotroped twice with methanol. The material was purified by mass directed autoprep to give the title compound (0.010 g) as a clear colourless film.

LC/MS: $R_t$ 2.39 min

Mass spectrum m/z 468 [MH$^+$].

Synthetic Method I (Interconversion)

Example 141: 1-[(2S)-4-(3,4-Dichloro-benzyl)morpholin-2-ylmethyl]-3-(5-diethylaminomethyl-[1,3,4]oxadiazol-2-ylmethyl)urea

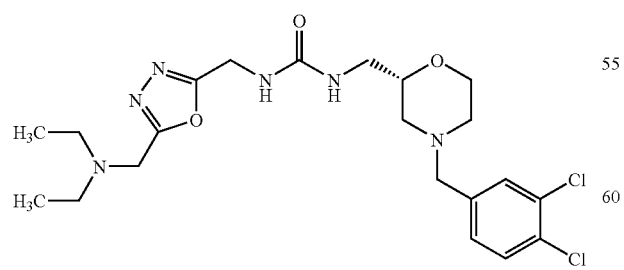

A vial containing Description 40 (0.015 g) was treated with diethylamine (0.3 ml of a 2M solution in tetrahydrofuran), anhydrous tetrahydrofuran (0.5 ml) and potassium carbonate (0.006 g). The mixture was stirred at 20° C. for 5 days, then blown down to dryness, dissolved in 5% methanol/ethyl acetate and purified using a silica SPE cartridge (1 g) which was eluted successively with 5, 10, 20% methanol/ethyl acetate to give the title compound (0.007 g) as a clear colourless film.

LC/M: $R_t$ 1.88 min

Mass spectrum m/z 485 [MH$^+$].

Synthetic Method J (Interconversion)

Example 169: 1-[(2S)-4-(3,4-Dichloro-benzyl)morpholin-2-ylmethyl]-3-[4-(3-methyl-[1,2,4]oxadiazol-5-yl)furan-2-ylmethyl]urea

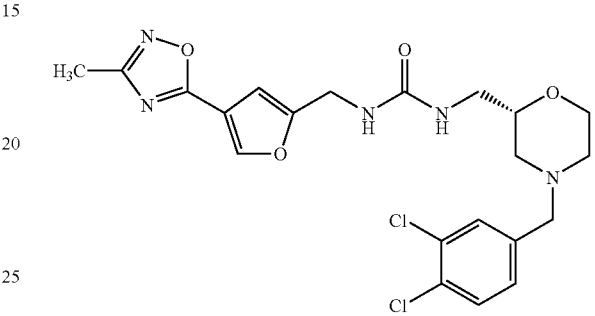

To a solution of Example 84 (0.1 g) in ethanol (2 ml) was added acetamidoxime (prepared according to Journal of Medicinal Chemistry (1986), 29(11), 2174-83.) (0.082 g). The suspension was treated with activated 4A powdered molecular sieves (0.360 g) and stirred for 5 mins. To the suspension was added 21% sodium ethoxide in ethanol (0.156 ml) and heated to reflux for 5 h. The mixture was filtered using a hydrophobic frit and the residue washed with methanol (2 ml). The filtrate was partitioned between ethyl acetate (50 ml) and 2M aqueous sodium hydroxide (40 ml). The phases were separated and the organic phase washed with 2M aqueous sodium hydroxide (20 ml), brine (20 ml) and the solvent removed in vacuo. The residue was purified by mass directed autoprep to give the title compound as a white solid (0.0175 g).

LC/MS $R_t$ 2.46 min m/z 480 [MH$^+$]

Synthetic Method K (Interconversion)

Example 171: 1-[(2S)-4-(3,4-Dichloro-benzyl)morpholin-2-ylmethyl]-3-[4-(5-methyl-[1,3,4]oxadiazol-2-yl)furan-2-ylmethyl]urea

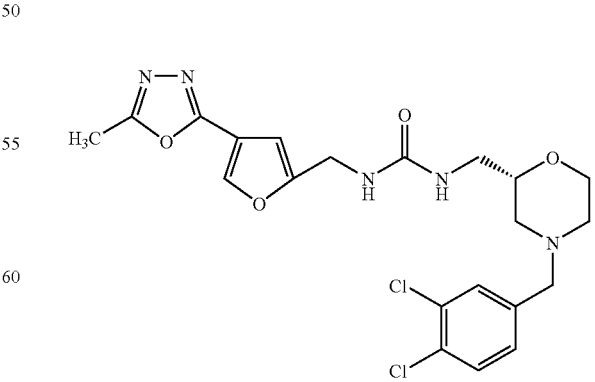

To a solution of Description 41 (0.1 g) in mixture of triethylorthoformate (2 ml) and triethylamine (0.132 ml) was added activated 4A powdered molecular sieves (0.3 g). The suspension was heated to reflux for 19 h. The suspension was filtered through a hydrophobic frit. The residue was washed with methanol and the filterate applied onto a sulphonic acid ion exchange cartridge (10 g solute SCX, pretreated with methanol). The cartridge was eluted with methanol followed by 10% 0.880 ammonia in methanol and the basic fraction concentrated in vacuo. The residue was further purified by silica SPE (10 g) eluting sequentially with ethyl acetate, 20:1 chloroform:methanol and 10:1 chloroform:methanol to give the title compound as a white solid (0.0067 g).

LC/MS $R_t$ 2.30 min m/z 480 [MH$^+$]

Example 170: 1-[(2S)-4-(3,4-Dichloro-benzyl)morpholin-2-ylmethyl]-3-[4-(5-methyl-4H-[1,2,4]triazol-3-yl)furan-2-ylmethyl]urea

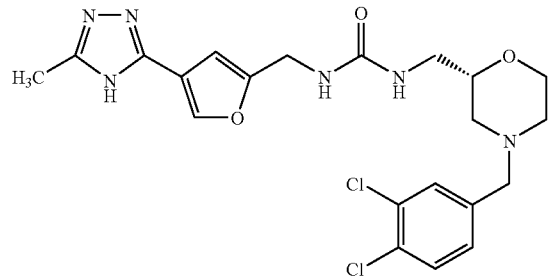

To a solution of Description 41 (0.1 g) in ethanol (2 ml) was added ethyl acetimidate hydrochloride (0.112 g). To the solution was added triethylamine (0.6 ml) and activated 4A powdered molecular sieves (0.360 g). The suspension was heated to reflux for 20 h. The mixture was applied equally onto sulphonic acid ion exchange cartridges (10 g×2 Isolute SCX, pre-treated with methanol). The cartridges were eluted with methanol followed by 10% 0.880 ammonia in methanol. The solvent was removed in vacuo from the basic fractions. The residue was further purified by mass directed autoprep to give the title compound as a pale yellow solid (0.0235 g).

LC/MS $R_t$ 2.18 min m/z 479 [MH$^+$]

Synthetic Method L (Interconversion)

Example 120: 1-[(2S)-4-(3,4-Dichloro-benzyl)morpholin-2-ylmethyl]-3-(4-[1,3,4]oxadiazol-2-yl-furan-2-ylmethyl)urea

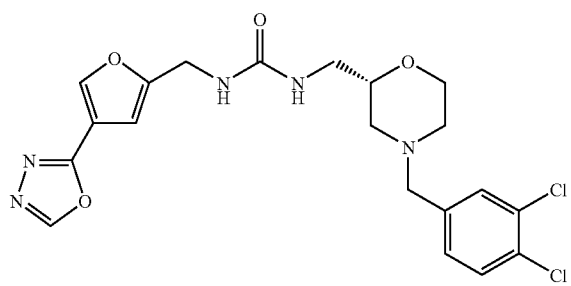

To a suspension of Description 43 (0.120 g) in tetrahydrofuran (3 ml) was added (methoxycarbonylsulphamoyl) triethylammonium hydroxide (0.140 g). The suspension was heated to 120° C. for 5 mins using a microwave (100 W). The mixture was applied onto sulphonic acid ion exchange (10 g, Isolute SCX, pretreated with methanol) and the cartridge was eluted with methanol followed by 10% 0.880 ammonia in methanol. The solvent was removed from the basic fraction in vacuo. The residue was purified by mass directed prep to give the title compound as a clear gum (0.007 g).

LC/MS: $R_t$ 2.18 min m/z 466 [MH$^+$].

Synthetic Method M (Interconversion)

Example 136: N-(5-{3-[(2S)-4-(3,4-Dichloro-benzyl)morpholin-2-ylmethyl]ureidomethyl}-4H-[1,2,4]triazol-3-yl)formamide

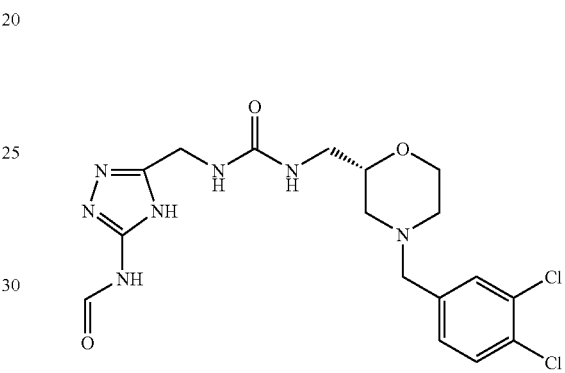

A solution of Example 32 (19 mg) in a mixture of acetonitrile and water with 0.05-0.1% formic acid was heated under a stream of nitrogen until the solvents were removed. The residue was purified by mass directed autoprep to give the title compound as a white solid (0.0004 g).

LC/MS $R_t$ 2.06 min m/z 442 [MH$^+$]

Synthetic Method N

Example 187: 1-[4-(3,4-Dichlorobenzyl)morpholin-2-ylmethyl]-3-(3,5-dimethyl-isoxazol-4-yl)urea To a stirred solution of Description 3 (0.025 g) in dichloromethane (1 ml) was added 4-isocyanato-3,5-dimethylisoxazole (0.0188 g). The mixture was stirred at 22° C. for 18 h before tris-(2-aminoethyl)amine polystyrene (Argonaut Technologies, 0.04 g @ 3.85 mmol/g) was added. Stirring was continued for a further 72 h before the mixture was poured onto a 1 g solid phase extraction (Isolute SCX sulphonic acid) cartridge. The cartridge was washed with methanol before eluting with 10% 0.880 ammonia solution in methanol. The basic fraction was evaporated in vacuo to give a pale yellow solid. The solid was purified by eluting through a 1 g silica solid phase extraction cartridge (Varian Bondelut) eluting sequentially with dichloromethane, ether, ethyl acetate, acetone, acetonitrile and methanol, to give the title compound as a white solid (0.0337 g).

LC/MS: $R_t$ 2.36 min, m/z 413 [MH$^+$].

Example 116: 5-{3-[(2S)-4-(3,4-Dichlorobenzyl)-morpholin-2-ylmethyl]-ureidomethyl}-thiophene-3-carboxylic acid methylamide

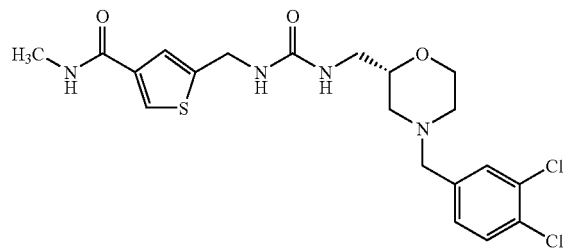

To Description 44 (0.232 g) was added a solution of Description 9 (0.662 g) and N,N-diisopropylethylamine (0.27 ml) in N,N-dimethylformamide (10 ml). The solution was stirred at 20° C. for 18 h. The mixture was partitioned between ethyl acetate (100 ml) and 2M aqueous sodium hydroxide (100 ml). The phases were separated and the organic phase washed with 2M aqueous sodium hydroxide (50 ml×2) and brine (50 ml×2). A gel formed in the organic phase. The organic phase was dried (MgSO$_4$), filtered and the MgSO$_4$ washed with methanol to dissolve the gel. The solvent was removed in vacuo. The residue was applied to sulphonic acid ion exchange (10 g×4, Isolute SCX, pretreated with methanol) and the cartridges were eluted with methanol followed by 10% 0.880 ammonia in methanol. The solvent was removed from the basic fraction in vacuo. The residue was purified by biotage (40 g) eluting with 20:1 chloroform:methanol and the solvent removed in vacuo to give the title compound (0.274 g).

LC/MS R$_t$ 2.31 min, m/z 471 [MH$^+$].

Example 117: 5-(3-[(2S)-4-{1-(3,4-Dichloro-phenyl)ethyl]morpholin-2-ylmethyl}ureidomethyl)furan-3-carboxylic acid methylamide

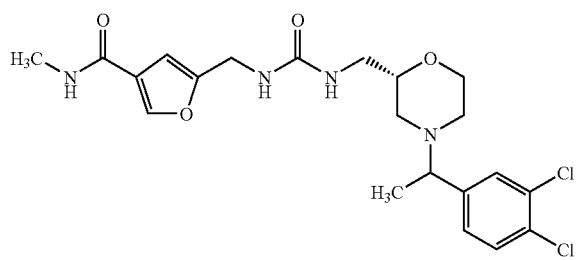

Prepared in similar fashion to Example 16 but using Description 47 and {(2S)-4-[1-(3,4-dichloro-phenyl)-ethyl]-morpholin-2-ylmethyl}carbamic acid 4-nitro-phenyl ester (prepared as described in WO 02/26723).

LC/MS R$_t$ 2.16 min m/z 469 [MH$^+$]

Example 118: 5-(3-{(2S)-4-[1-(3,4-Dichloro-phenyl)ethyl]morpholin-2-ylmethyl}ureidomethyl)furan-3-carboxylic acid methylamide Isomer 1 and Example 119: 5-(3-{(2S)-4-[1-(3,4-Dichloro-phenyl)ethyl]morpholin-2-ylmethyl}ureidomethyl)furan-3-carboxylic acid methylamide Isomer 2

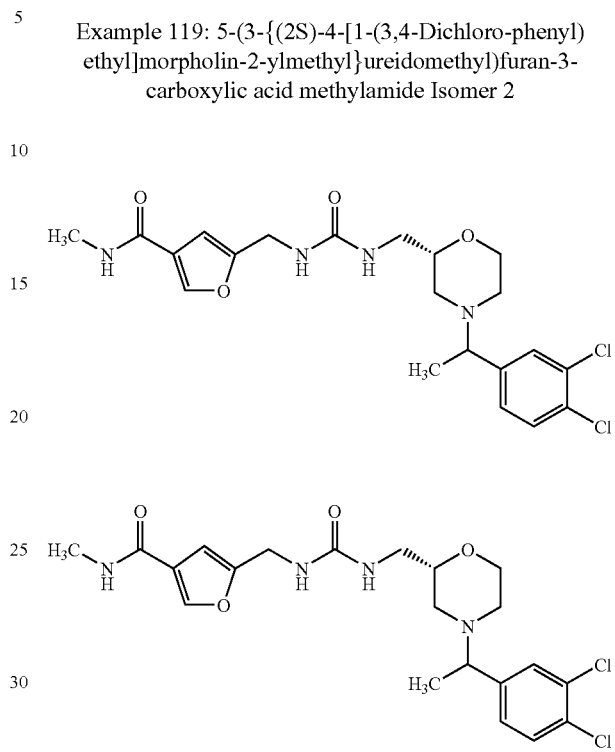

Example 117 (0.154 g) was separated on a Diacel CHIRALPAK AD column (0.46 cm×25 cm) using 15% ethanol/heptane at 1 ml/min$^{-1}$, wavelength 215 nm at room temperature. The two isomers have retention times of 12.8 min and 15.0 min.

Example 118 was obtained as a white solid (0.032 g); LC/MS R$_t$ 2.11 min m/z 469 [MH$^+$]

Example 119 was obtained as a white solid (0.047 g); LC/MS R$_t$ 2.11 min m/z 469 [MH$^+$]

Example 97: 1-(2-Cyclopropylmethyl-2H-tetrazol-5-ylmethyl)-3-[(2S)-4-(3,4-dichlorobenzyl)morpholin-2-ylmethyl]-urea and Example 98: 1-(1-Cyclopropylmethyl-1H-tetrazol-5-ylmethyl)-3-[(2S)-4-(3,4-dichlorobenzyl)morpholin-2-ylmethyl]-urea Example 97

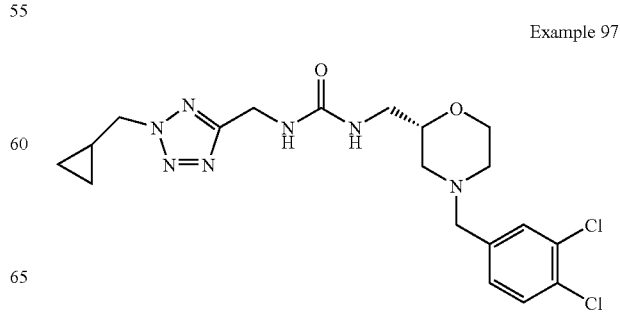

Example 98

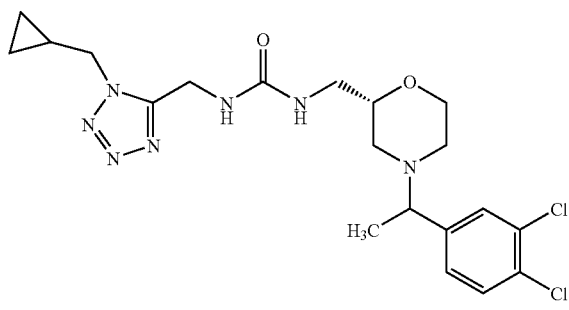

To a stirred solution of Example 31 (0.063 g) in N,N-dimethylformamide (3 ml) was added potassium carbonate (0.050 g) followed by (bromomethyl)cyclopropane (0.0166 ml) and sodium iodide (0.026 g). The mixture was stirred at 22° C. for 18 h, then at 80° C. for 18 h, before cooling and being applied to a 5 g SCX ion-exchange cartridge (preconditioned with methanol). The cartridge was eluted with methanol, followed by 10% 0.880 ammonia solution in methanol. The first ammonia fraction was evaporated in vacuo and the residue further purified by Biotage™ flash chromatography on silica gel, eluting with 100:8:1 dichloromethane/ethanol/0.880 ammonia solution. The fractions of the first eluting product were combined and the solvent evaporated in vacuo to give the title compound (Example 97) (0.0261 g) as a colourless glass.

LC/MS: $R_t$=2.32 min, m/z 454 [MH$^+$]

The fractions of the second eluting product were combined and the solvent evaporated in vacuo to give the title compound (Example 98) (0.016 g) as a colourless glass.

LC/MS: $R_t$=2.30 min, m/z 454 [MH$^+$]

Example 91: 1-{(2S)-4-[1-(3,4-Dichlorophenyl)ethyl]morpholin-2-ylmethyl}-3-(2-methyl-2H-tetrazol-5-ylmethyl)urea

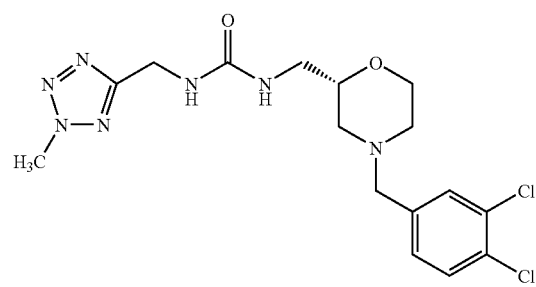

Prepared in similar fashion to Example 16 but using C-(2-methyl-2H-tetrazol-5-yl)-methylamine and 4-nitrophenyl {(2S)-4-[1-(3,4-dichlorophenyl)ethyl]morpholin-2-yl}methylcarbamate Isomer I (prepared as described in WO 02/26723).

LC/MS $R_t$ 2.22 min m/z 428 [MH$^+$]

Example 93: 1-{(2S)-4-[1-(3,4-Dichlorophenyl)ethyl]-morpholin-2-ylmethyl}-3-(2-methyl-2H-tetrazol-5-ylmethyl)urea

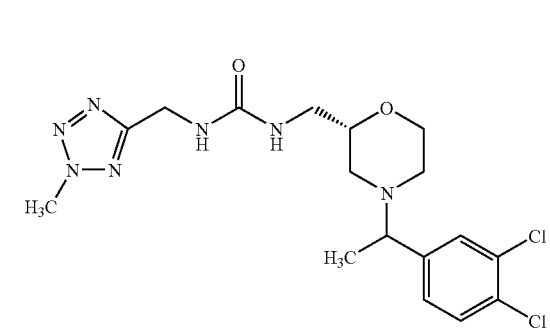

Prepared in similar fashion to Example 16 but using C-(2-methyl-2H-tetrazol-5-yl)-methylamine and 4-nitrophenyl {(2S)-4-[1-(3,4-dichlorophenyl)ethyl]morpholin-2-yl}methylcarbamate Isomer II (prepared as described in WO 02/26723).

LC/MS $R_t$ 2.21 min m/z 428 [MH$^+$]

Example 92: 1-[(2S)-4-[1-(3,4-Difluorophenyl)ethyl]morpholin-2-ylmethyl]-3-(2-methyl-2H-tetrazol-5-ylmethyl)urea

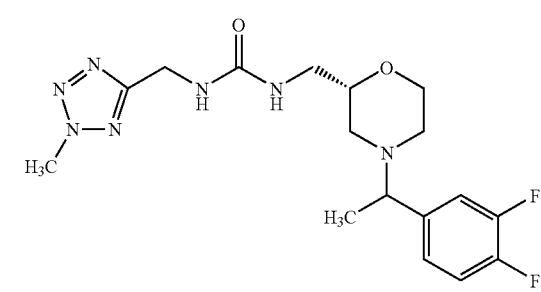

Prepared in similar fashion to Example 16 but using C-(2-methyl-2H-tetrazol-5-yl)-methylamine and Description 51.

LC/MS $R_t$ 1.94 min m/z 396 [MH$^+$]

Example 94: 1-{(2S)-4-[1-(3,4-Difluorophenyl)ethyl]morpholin-2-ylmethyl}-3-(2-methyl-2H-tetrazol-5-ylmethyl)urea

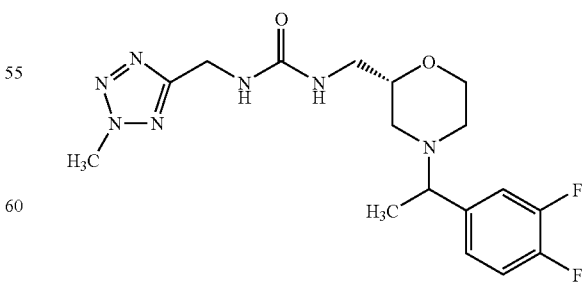

Prepared in similar fashion to Example 16 but using C-(2-methyl-2H-tetrazol-5-yl)-methylamine and Description 52.

LC/MS $R_t$ 1.91 min m/z 396 [MH$^+$]

The further examples described in the following Tables were prepared according to or by analogy with the methods hereinbefore described.

TABLE 1

| Ex. No. | Synthetic Method | R¹ | R² | R⁷ | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 1 | C | (1-isopropyl-tetrazol-5-yl), H₃C-CH(CH₃)- on N1 | 3,4-di-ClPh | H | S | 442.352 | 442 |
| 30 | C | (2-isopropyl-tetrazol-5-yl) | 3,4-di-ClPh | H | S | 442.352 | 442 |
| 31 | A | (1H-tetrazol-5-yl) | 3,4-di-ClPh | H | S | 400.27 | 400 |
| 51 | A | (2-methyl-tetrazol-5-yl) | 3-Cl,4-FPh | H | S | 397.84 | 398 |
| 88 | A | (1H-tetrazol-5-yl) | 3,4-di-ClPh | H | RS | 400.27 | 400 |
| 89 | A | (1-methyl-tetrazol-5-yl) | 3,4-di-ClPh | H | RS | 414.30 | 414 |
| 90 | A | (2-methyl-tetrazol-5-yl) | 3,4-di-FPh | H | S | 381.39 | 382 |

TABLE 1-continued

| Ex. No. | Synthetic Method | R¹ | R² | R⁷ | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 91 | A | 5-methyl-2-methyl-2H-tetrazol-2-yl | 3,4-di-ClPh | Me (R or S) | S | 428.33 | 428 |
| 92 | A | 5-methyl-2-methyl-2H-tetrazol-2-yl | 3,4-di-FPh | Me (R or S) | S | 395.42 | 396 |
| 93 | A | 5-methyl-2-methyl-2H-tetrazol-2-yl | 3,4-di-ClPh | Me (S or R) | S | 428.33 | 428 |
| 94 | A | 5-methyl-2-methyl-2H-tetrazol-2-yl | 3,4-di-FPh | Me (S or R) | S | 395.42 | 396 |
| 95 | A + C | methyl 2-(5-methyl-2H-tetrazol-2-yl)acetate | 3,4-di-ClPh | H | S | 472.33 | 472 |
| 96 | A + C | methyl 2-(5-methyl-1H-tetrazol-1-yl)acetate | 3,4-di-ClPh | H | S | 472.33 | 472 |

TABLE 1-continued

| Ex. No. | Synthetic Method | R[1] | R[2] | R[7] | Stereochem at position (*) | Calculated Mol. Wt. (as free base) | Observed Mol. Wt. (LC/MS) [M + H]+ of lowest mass isomer unless otherwise indicated |
|---|---|---|---|---|---|---|---|
| 97 | A + C | cyclopropylmethyl-2-(5-methyltetrazol-2-yl) | 3,4-di-ClPh | H | S | 454.36 | 454 |
| 98 | A + C | cyclopropylmethyl-1-(5-methyltetrazol-1-yl) | 3,4-di-ClPh | H | S | 454.36 | 454 |
| 99 | A + C | 2-ethyl-5-methyltetrazol-2-yl | 3,4-di-ClPh | H | S | 428.33 | 428 |
| 100 | A + C | 1-ethyl-5-methyltetrazol-1-yl | 3,4-di-ClPh | H | S | 428.33 | 428 |
| 101 | A + G | tBu-tetrazolyl-methyl | 3,4-di-ClPh | H | S | 456.38 | 456 |
| 104 | A + C | NC-CH2-tetrazol-2-yl-methyl | 3,4-di-ClPh | H | S | 439.31 | 439 |
| 105 | A + C | NC-CH2-tetrazol-1-yl-methyl | 3,4-di-ClPh | H | S | 439.31 | 439 |

TABLE 1-continued

[Structure: R¹-CH₂-NH-C(=O)-NH-CH₂-[morpholine with * at 2-position, N-CH(R⁷)(R²)]]

| Ex. No. | Synthetic Method | R¹ | R² | R⁷ | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 106 | A + C | 2-(iPr-CH₂)-tetrazol-5-yl-methyl | 3,4-di-ClPh | H | S | 456.38 | 456 |
| 107 | A + C | 1-(iPr-CH₂)-tetrazol-5-yl-methyl | 3,4-di-ClPh | H | S | 456.38 | 456 |

TABLE 2

[Structure: R¹-CH₂-NH-C(=O)-NH-CH₂-[morpholine with * at 2-position, N-CH₂-R²]]

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 2* | A | 4-methyl-1H-1,2,3-triazol-5-yl | 3,4-di-ClPh | S | 399.28 | 399 |
| 3* | A | 1-methyl-4-methyl-1,2,3-triazol-5-yl | 3,4-di-ClPh | S | 413.31 | 413 |
| 4 | A | 2-methyl-4-methyl-2H-1,2,3-triazol-5-yl | 3,4-di-ClPh | S | 413.31 | 413 |
| 5 | A | 1-methyl-5-methyl-1H-1,2,4-triazol-3-yl | 3,4-di-ClPh | S | 413.31 | 413 |

TABLE 2-continued

[Structure: R¹-CH₂-NH-C(=O)-NH-CH₂-[morpholine with N-CH₂-R²], stereocenter marked *]

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 32 | A | 3-amino-5-methyl-4H-1,2,4-triazol-yl | 3,4-di-ClPh | S | 414.30 | 414 |
| 136 | A + M | 5-methyl-3-(formylamino)-1,2,4-triazol-yl | 3,4-diClPh | S | 442.31 | 442 |

TABLE 3

[Structure: R¹-CH₂-NH-C(=O)-NH-CH₂-[morpholine with N-CH₂-R²], stereocenter marked *]

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 6 | A | 5-methyl-1,3,4-oxadiazol-2-yl | 3,4-di-ClPh | S | 414.30 | 414 |
| 7 | A | ethyl 5-methyl-1,2,4-oxadiazole-3-carboxylate | 3,4-di-ClPh | S | 472.33 | 472 |
| 8 | B | N-methyl-5-methyl-1,2,4-oxadiazole-3-carboxamide | 3,4-di-ClPh | S | 457.32 | 457 |

TABLE 3-continued

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 9 | B | *N-ethyl-5-methyl-1,2,4-oxadiazole-3-carboxamide group* | 3,4-di-ClPh | S | 471.35 | 471 |
| 10 | A | *3-(5-methylisoxazol-3-yl)-1,2,4-oxadiazol-5-yl group* | 3,4-di-ClPh | S | 481.34 | 481 |
| 11 | A | *N-methyl-3-methyl-1,2,4-oxadiazole-5-carboxamide group* | 3,4-di-ClPh | S | 457.32 | 457 |
| 12 | A | *N-ethyl-3-methyl-1,2,4-oxadiazole-5-carboxamide group* | 3,4-di-ClPh | S | 471.35 | 471 |
| 13 | A | *5-(5-methylisoxazol-3-yl)-3-methyl-1,2,4-oxadiazole group* | 3,4-di-FPh | S | 448.43 | 449 |
| 14 | A | *5-(5-methylisoxazol-3-yl)-3-methyl-1,2,4-oxadiazole group* | 3-ClPh | S | 446.90 | 447 |
| 15 | A | *5-(5-methylisoxazol-3-yl)-3-methyl-1,2,4-oxadiazole group* | 4-FPh | S | 430.44 | 431 |
| 16 | A | *2,5-dimethyl-1,3,4-oxadiazole group* | 3,4-di-ClPh | S | 414.30 | 414 |

TABLE 3-continued

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 21 | A | 5-methylisoxazol-3-yl linked to 3-methyl-1,2,4-oxadiazol-5-yl | 3-Cl-4-FPh | S | 464.89 | 465 |
| 22 | A | 5-methyl-1,3,4-oxadiazol-2-yl | 3,4-di-ClPh | S | 400.27 | 400 |
| 23 | B | pyrrolidin-1-yl-carbonyl-(5-methyl-1,2,4-oxadiazol-3-yl) | 3,4-di-ClPh | S | 497.39 | 497 |
| 24 | B | isopropyl-NH-C(O)-(5-methyl-1,2,4-oxadiazol-3-yl) | 3,4-di-ClPh | S | 485.37 | 485 |
| 25 | B | ethyl-NH-C(O)-(5-methyl-1,2,4-oxadiazol-3-yl) | 3,4-di-FPh | S | 438.44 | 439 |
| 26 | B | isopropyl-NH-C(O)-(5-methyl-1,2,4-oxadiazol-3-yl) | 3,4-di-FPh | S | 452.47 | 453 |
| 27 | B | cyclopropyl-NH-C(O)-(5-methyl-1,2,4-oxadiazol-3-yl) | 3,4-di-FPh | S | 450.45 | 451 |
| 28 | B | pyrrolidin-1-yl-C(O)-(5-methyl-1,2,4-oxadiazol-3-yl) | 3,4-di-FPh | S | 464.48 | 465 |

TABLE 3-continued

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 29* | B | (N,N-isopropyl,methyl-carbamoyl)-5-methyl-1,3,4-oxadiazole | 3,4-di-FPh | S | 466.49 | 467 |
| 35 | A | (N-methylcarbamoyl)-5-methyl-1,3,4-oxadiazole | 3,4-di-ClPh | S | 457.32 | 457 |
| 36 | A | (N-ethylcarbamoyl)-5-methyl-1,3,4-oxadiazole | 3,4-di-ClPh | S | 471.35 | 471 |
| 37 | A | (N-methylcarbamoyl)-5-methyl-1,3,4-oxadiazole | 3,4-di-FPh | S | 424.41 | 425 |
| 38* | A | (N-isopropylcarbamoyl)-5-methyl-1,3,4-oxadiazole | 3,4-di-ClPh | S | 485.37 | 485 |
| 39* | A | (N-ethylcarbamoyl)-5-methyl-1,3,4-oxadiazole | 3,4-di-FPh | S | 438.43 | 439 |
| 40* | A | (N-isopropylcarbamoyl)-5-methyl-1,3,4-oxadiazole | 3,4-di-FPh | S | 452.46 | 453 |
| 137 | A | 2-methyl-5-ethyl-1,3,4-oxadiazole | 3,4-diClPh | S | 428.32 | 428 |
| 138 | A + B | (N-methylcarbamoyl)-5-methyl-1,3,4-oxadiazole | 3,4-diClPh | S | 457.32 | 457 |

TABLE 3-continued

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 139 | A + H | 5-(trifluoromethyl)-2-methyl-1,3,4-oxadiazole | 3,4-diClPh | S | 468.27 | 468 |
| 140 | A + I | 5-(morpholinomethyl)-2-methyl-1,3,4-oxadiazole | 3,4-diClPh | S | 499.40 | 499 |
| 141 | A + I | 5-((diethylamino)methyl)-2-methyl-1,3,4-oxadiazole | 3,4-diClPh | S | 485.42 | 485 |
| 142 | A + I | 5-((ethylamino)methyl)-2-methyl-1,3,4-oxadiazole | 3,4-diClPh | S | 457.36 | 457 |

TABLE 4

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 17 | A | pyrazine | 1 | 3,4-di-ClPh | S | 410.31 | 410 |
| 34 | A | 1-methyl-1H-pyrazole | 1 | 3,4-di-ClPh | S | 412.32 | 412 |

TABLE 4-continued

| Ex. No. | Synthetic Method | R[1] | z | R[2] | Stereochem at position (*) | Calculated Mol. Wt. (as free base) | Observed Mol. Wt. (LC/MS) [M + H]+ of lowest mass isomer unless otherwise indicated |
|---|---|---|---|---|---|---|---|
| 46 | A | 1-methyl-3-methylpyrazole | 1 | 3,4-di-ClPh | S | 412.32 | 412 |
| 47 | A | 3-methylpyrazole | 1 | 3,4-di-ClPh | S | 398.30 | 398 |
| 48 | A | 3,5-dimethylpyrazole | 1 | 3,4-di-ClPh | S | 412.32 | 412 |
| 143 | A | 2-methylimidazole | 1 | 3,4-diClPh | RS | 398.30 | 398 |
| 144 | A | 1,5-dimethylimidazole | 1 | 3,4-diClPh | RS | 412.32 | 412 |
| 145 | A | 4-methylimidazole | 2 | 3,4-diClPh | S | 412.32 | 412 |
| 146 | A + E | 1-acetyl-3-methylpyrazole | 1 | 3,4-diClPh | S | 440.33 | 440 |
| 147 | A | 4-methylpyridine | 2 | 3,4-diClPh | S | 423.35 | 423 |
| 148 | A | 2-methylpyridine | 2 | 3,4-diClPh | S | 423.35 | 423 |

TABLE 4-continued

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 149 | A | 3-methylpyridine | 2 | 3,4-diClPh | S | 423.35 | 423 |
| 150 | A | 5-methylnicotinamide | 1 | 3,4-diClPh | S | 452.34 | 452 |
| 151 | A | 4-amino-5-methylpyrimidine | 1 | 3,4-diClPh | RS | 425.32 | 425 |
| 152 | A | 4-hydroxy-2,5-dimethylpyrimidine | 1 | 3,4-diClPh | RS | 440.33 | 440 |
| 189 | A (at elevated temp.) | 4-methylpyridine | 0 | 3,4-diClPh | RS | 395.29 | 395 |
| 190 | A (at elevated temp.) | 2-methylpyridine | 0 | 3,4-diClPh | RS | 395.29 | 395 |
| 191 | A | 3-methylpyridine | 0 | 3,4-diClPh | RS | 395.29 | 395 |
| 192 | F | 2-methylpyridine | 2 | 3,4-diClPh | RS | 423.35 | 423 |
| 193 | F | 3-methylpyridine | 2 | 3,4-diClPh | RS | 423.35 | 423 |

TABLE 5

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 18 | A | 3,5-dimethylisoxazol-4-yl (3-Me, 5-Me) | 1 | 3,4-di-ClPh | S | 413.31 | 413 |
| 19 | A | 3,5-dimethylisoxazol-4-yl | 1 | 3,4-di-FPh | S | 380.40 | 381 |
| 20 | A | 3,5-dimethylisoxazol-4-yl (isomer) | 1 | 3,4-di-ClPh | S | 413.31 | 413 |
| 33 | A | 3,5-dimethylisoxazol-4-yl (isomer) | 1 | 3,4-di-FPh | S | 380.40 | 381 |
| 49 | A | ethyl 5-methylisoxazole-3-carboxylate | 1 | 3,4-di-FPh | S | 438.44 | 439 |
| 50 | A | ethyl 5-methylisoxazole-3-carboxylate | 1 | 3,4-di-ClPh | S | 471.34 | 471 |
| 52 | A | 3-methylisoxazol-5-yl | 1 | 3-Cl,4-FPh | S | 396.85 | 397 |
| 53 | A | 5-methylisoxazol-3-yl | 1 | 3-Cl,4-FPh | S | 396.85 | 397 |
| 54 | A | 5-methylisoxazol-3-yl | 1 | 2-chloro-thiophen-5-yl | S | 384.89 | 385 |

TABLE 5-continued

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 61 | A + B | (N-methylcarboxamide-5-methylisoxazol-3-yl) | 1 | 3,4-di-ClPh | S | 456.33 | 456 |
| 62 | A + B | (N-ethylcarboxamide-5-methylisoxazol-3-yl) | 1 | 3,4-di-ClPh | S | 470.36 | 470 |
| 63 | A + B | (N,N-dimethylcarboxamide-5-methylisoxazol-3-yl) | 1 | 3,4-di-ClPh | S | 470.36 | 470 |
| 64 | A + B | (N-methylcarboxamide-5-methylisoxazol-3-yl) | 1 | 3,4-di-FPh | S | 423.42 | 424 |
| 65 | A + B | (N-ethylcarboxamide-5-methylisoxazol-3-yl) | 1 | 3,4-di-FPh | S | 437.45 | 438 |
| 66 | A + B | (N,N-dimethylcarboxamide-5-methylisoxazol-3-yl) | 1 | 3,4-di-FPh | S | 437.45 | 438 |
| 67 | A + B | (N-isopropylcarboxamide-5-methylisoxazol-3-yl) | 1 | 3,4-di-FPh | S | 451.48 | 452 |

TABLE 5-continued

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 68 | A + D | (2-methyl-thiazol-4-yl)-C(O)NH-CH₃ | 1 | 3,4-di-FPh | S | 439.48 | 440 |
| 69 | A + D | (2-methyl-thiazol-4-yl)-C(O)NH-CH₂CH₃ | 1 | 3,4-di-FPh | S | 453.51 | 454 |
| 70 | A + D | (2-methyl-thiazol-4-yl)-C(O)N(CH₃)₂ | 1 | 3,4-di-FPh | S | 453.51 | 454 |
| 71 | A + D | (2-methyl-thiazol-4-yl)-C(O)NH-iPr | 1 | 3,4-di-FPh | S | 467.54 | 468 |
| 72 | A | (2-methyl-thiazol-4-yl)-C(O)O-CH₂CH₃ | 1 | 3,4-di-FPh | S | 454.50 | 455 |
| 73 | A + D | (2-methyl-thiazol-4-yl)-C(O)OH | 1 | 3,4-di-FPh | S | 426.44 | 427 |
| 153 | A + B | (5-methyl-isoxazol-3-yl)-C(O)NH-CH₂-cyclopropyl | 1 | 3,4-diClPh | S | 496.40 | 496 |

TABLE 5-continued

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 154 | A + B | pyrrolidine-N-C(O)-(5-methylisoxazol-3-yl) | 1 | 3,4-diClPh | S | 496.40 | 496 |
| 155 | A + B | iPrNH-C(O)-(5-methylisoxazol-3-yl) | 1 | 3,4-diClPh | S | 484.39 | 484 |
| 156 | A | CH₃O-C(O)-(2-methyloxazol-4-yl) | 1 | 3,4-diFPh | S | 424.41 | 425 |
| 157 | A | CH₃O-C(O)-(2-methyloxazol-4-yl) | 1 | 3,4-diClPh | S | 457.32 | 457 |
| 158 | A + B | EtNH-C(O)-(2-methyloxazol-4-yl) | 1 | 3,4-diFPh | S | 437.45 | 438 |
| 159 | A + B | EtNH-C(O)-(2-methyloxazol-4-yl) | 1 | 3,4-diClPh | S | 470.36 | 470 |
| 160 | A + B | cyclopropyl-CH₂-NH-C(O)-(2-methyloxazol-4-yl) | 1 | 3,4-diFPh | S | 463.49 | 464 |

TABLE 5-continued

| Ex. No. | Synthetic Method | R¹ | z | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 161 | A + B | H₃C-NH-C(O)-(2-methyloxazol-4-yl) | 1 | 3,4-diClPh | S | 456.33 | 457 |
| 162 | A + B | pyrrolidin-1-yl-C(O)-(2-methyloxazol-4-yl) | 1 | 3,4-diFPh | S | 463.49 | 464 |
| 163 | A + B | (H₃C)₂CH-NH-C(O)-(2-methyloxazol-4-yl) | 1 | 3,4-diFPh | S | 451.48 | 452 |
| 164 | A + B | (H₃C)₂CH-NH-C(O)-(2-methyloxazol-4-yl) | 1 | 3,4-diClPh | S | 484.39 | 484 |
| 187 | N | 3,4,5-trimethylisoxazol-yl | 0 | 3,4-diClPh | RS | 413.31 | 413 |
| 188 | A | 3-phenyl-4-methyl-5-methylisoxazol-yl | 1 | 3,4-diClPh | RS | 489.41 | 489 |

TABLE 6

[Structure: R¹-NH-C(=O)-NH-CH₂-(morpholine with stereocenter *)-N-CH(R⁷)(R²) with stereocenter **]

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 41** | D | HOOC-(5-methylfuran-2-yl) | 3,4-di-ClPh | H | S | — | 442.30 | 442 |
| 42 | A | EtO-C(=O)-(5-methylfuran-2-yl) | 3,4-di-ClPh | H | S | — | 470.36 | 470 |
| 43 | D | CH₃NH-C(=O)-(5-methylfuran-2-yl) | 3,4-di-ClPh | H | S | — | 455.35 | 455 |
| 44 | D | EtNH-C(=O)-(5-methylfuran-2-yl) | 3,4-di-ClPh | H | S | — | 469.37 | 469 |
| 45 | D | iPrNH-C(=O)-(5-methylfuran-2-yl) | 3,4-di-ClPh | H | S | — | 483.40 | 483 |
| 55 | A + D | CH₃NH-C(=O)-(5-methylfuran-3-yl) | 3,4-di-ClPh | H | S | — | 455.35 | 455 |
| 56 | A + D | EtNH-C(=O)-(5-methylfuran-3-yl) | 3,4-di-ClPh | H | S | — | 469.37 | 469 |
| 57 | A + D | iPrNH-C(=O)-(5-methylfuran-3-yl) | 3,4-di-ClPh | H | S | — | 483.40 | 483 |

TABLE 6-continued

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 58 | A + D | N-methyl 5-methyl-furan-3-carboxamide | 3,4-di-FPh | H | S | — | 422.43 | 423 |
| 59 | A + D | N-ethyl 5-methyl-furan-3-carboxamide | 3,4-di-FPh | H | S | — | 436.46 | 437 |
| 60 | A + D | N-isopropyl 5-methyl-furan-3-carboxamide | 3,4-di-FPh | H | S | — | 450.49 | 451 |
| 74 | A + D | N-methyl 5-methyl-thiophene-2-carboxamide | 3,4-di-FPh | H | S | — | 438.52 | 439 |
| 75 | A + D | N-ethyl 5-methyl-thiophene-2-carboxamide | 3,4-di-FPh | H | S | — | 452.52 | 453 |
| 76 | A + D | N-isopropyl 5-methyl-thiophene-2-carboxamide | 3,4-di-FPh | H | S | — | 466.54 | 467 |
| 77 | A + D | N-methyl 4-methyl-thiophene-2-carboxamide | 3,4-di-FPh | H | S | — | 438.52 | 439 |

TABLE 6-continued

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 78 | A + D | 4-methyl-2-(N-ethylcarboxamido)thiophene | 3,4-di-FPh | H | S | — | 452.52 | 453 |
| 79 | A + D | 4-methyl-2-(N-isopropylcarboxamido)thiophene | 3,4-di-FPh | H | S | — | 466.54 | 467 |
| 80 | A | 4-methyl-2-(methoxycarbonyl)thiophene | 3,4-di-FPh | H | S | — | 439.48 | 440 |
| 81 | A + D | 4-methyl-2-carboxythiophene | 3,4-di-FPh | H | S | — | 425.45 | 426 |
| 82 | A | 5-methyl-2-(methoxycarbonyl)thiophene | 3,4-di-FPh | H | S | — | 439.48 | 440 |
| 83 | A + D | 5-methyl-2-carboxythiophene | 3,4-di-FPh | H | S | — | 425.45 | 426 |
| 84 | A | 5-methyl-3-(ethoxycarbonyl)furan | 3,4-di-ClPh | H | S | — | 470.35 | 470 |

TABLE 6-continued

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 85 | A + D | 5-methyl-3-furancarboxylic acid | 3,4-di-ClPh | H | S | — | 442.30 | 442 |
| 86 | A | ethyl 5-methyl-3-furancarboxylate | 3,4-di-FPh | H | S | — | 437.44 | 438 |
| 87 | A + D | 5-methyl-3-furancarboxylic acid | 3,4-di-FPh | H | S | — | 409.39 | 410 |
| 108 | A + D | N-methyl-4-methylthiophene-2-carboxamide | 3,4-di-ClPh | H | S | — | 471.41 | 471 |
| 109 | A + D | N-methyl-5-methylthiophene-2-carboxamide | 3,4-di-ClPh | H | S | — | 471.41 | 471 |
| 110 | A + D | N-ethyl-4-methylthiophene-2-carboxamide | 3,4-di-ClPh | H | S | — | 485.44 | 485 |
| 111 | A + D | N-ethyl-5-methylthiophene-2-carboxamide | 3,4-di-ClPh | H | S | — | 485.44 | 485 |
| 112 | A + D | N-isopropyl-5-methylthiophene-3-carboxamide | 3,4-di-FPh | H | S | — | 466.55 | 467 |
| 113 | A + D | N-ethyl-5-methylthiophene-3-carboxamide | 3,4-di-FPh | H | S | — | 452.53 | 453 |
| 114 | A + D | N-methyl-5-methylthiophene-3-carboxamide | 3,4-di-FPh | H | S | — | 438.50 | 439 |

TABLE 6-continued

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 115 | A + D | *N-ethyl-5-methylthiophene-3-carboxamide* | 3,4-di-ClPh | H | S | — | 485.44 | 485 |
| 116 | A + D | *N-methyl-5-methylthiophene-3-carboxamide* | 3,4-di-ClPh | H | S | — | 471.41 | 471 |
| 117 | A + D | *N-methyl-5-methylfuran-3-carboxamide* | 3,4-di-ClPh | Me | S | RS | 469.37 | 469 |
| 118 | A + D | *N-methyl-5-methylfuran-3-carboxamide* | 3,4-di-ClPh | Me | S | R or S | 469.37 | 469 |
| 119 | A + D | *N-methyl-5-methylfuran-3-carboxamide* | 3,4-di-ClPh | Me | S | S or R | 469.37 | 469 |
| 120 | A + D + L | *2-(5-methylfuran-3-yl)-1,3,4-oxadiazole* | 3,4-di-ClPh | H | S | — | 466.33 | 466 |
| 165 | F | *2-ethylfuran* | 3,4-di-ClPh | H | RS | — | 412.32 | 412 |
| 169 | A + J | *3-methyl-5-(5-methylfuran-3-yl)-1,2,4-oxadiazole* | 3,4-di-ClPh | H | S | — | 480.35 | 480 |
| 170 | A + D + K | *5-methyl-3-(5-methylfuran-3-yl)-1H-1,2,4-triazole* | 3,4-di-ClPh | H | S | — | 479.37 | 479 |

TABLE 6-continued

| Ex. No. | Synthetic Method | R¹ | R² | R⁷ | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|---|
| 171 | A + D + K | 2-methyl-5-(4-methylfuran-2-yl)-1,3,4-oxadiazole | 3,4-di-ClPh | H | S | — | 480.35 | 480 |

TABLE 7

| Ex. No. | Synthetic Method | R¹ | R² | R⁷ | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|---|
| 102 | A | 5-(trifluoromethyl)-2H-tetrazol-2-ylmethyl | 3,4-di-FPh | H | S | 449.39 | 450 |
| 103 | A | 5-(trifluoromethyl)-2H-tetrazol-2-ylmethyl | 3,4-di-ClPh | H | S | 482.30 | 482 |
| 185 | F | 1-ethyl-2-phenyl-1H-imidazole | 3,4-di-ClPh | H | RS | 488.42 | 488 |
| 186 | F | 1-ethyl-1H-imidazole | 3,4-di-ClPh | H | RS | 412.32 | 412 |

TABLE 8

[Structure: R¹-CH₂-NH-C(=O)-NH-CH₂-[morpholine with * at 2-position, ** at 5-position with CH₃, and N-CH₂-R²]]

| Ex. No. | Synthetic Method | R¹ | R² | Stereochem at position (*) | Stereochem at position (**) | Calculated Mol. Wt. (as free base) | Observed Mol. Wt. (LC/MS) [M + H]⁺ of lowest mass isomer unless otherwise indicated |
|---|---|---|---|---|---|---|---|
| 181 | A | H₃C-NH-C(=O)-(5-methylfuran-3-yl) | 3,4-di-ClPh | R | R | 469.37 | 469 |
| 182 | A | H₃C-NH-C(=O)-(5-methylfuran-3-yl) | 3,4-di-ClPh | S | R | 469.37 | 469 |

TABLE 9

[Structure: R¹-CH₂-NH-C(=O)-NH-CH₂-[morpholine with * at 2-position, and N-CH₂-R²]]

| Ex. No. | Synthetic Method | R¹ | R² | Stereochem at position (*) | Calculated Mol. Wt. (as free base) | Observed Mol. Wt. (LC/MS) [M + H]⁺ of lowest mass isomer unless otherwise indicated |
|---|---|---|---|---|---|---|
| 183 | F | 3-ethylbenzofuran | 3,4-di-ClPh | RS | 462.38 | 462 |
| 184 | A | 2-methylbenzimidazole | 3,4-di-ClPh | RS | 448.36 | 448 |

In the Example Tables 1 to 9, it is to be noted that Examples 2, 3, 20, 29, 38, 39, 40, 138, 139, and 189 are formate salts, and Examples 41 and 85 are triethylamine salts.

The invention claimed is:

1. A compound of formula (If)

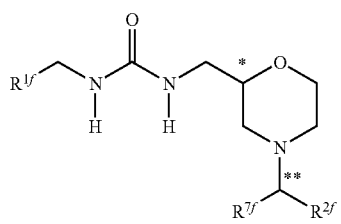

(If)

wherein;

$R^{1f}$ is unsubstituted furanyl or furanyl substituted with oxadiazolyl, methyl-substituted oxadiazolyl, or methyl-substituted triazolyl, carboxy, $C_{1-6}$alkoxycarbonyl, or (mono- or di-$C_{1-6}$alkyl)aminocarbonyl; or thiophenyl substituted with (mono- or di-$C_{1-6}$alkyl)aminocarbonyl, $C_{1-6}$alkoxycarbonyl, or carboxy;

$R^{2f}$ is 3,4-dichlorophenyl or 3,4-difluorophenyl, and;

$R^{7f}$ is hydrogen or methyl;

or a salt thereof, with the proviso that the compound is not N-{[4-(3,4-dichlorobenzyl)morpholin-2-yl]methyl}-N'-(2-furylmethyl)urea.

2. A compound of Formula (If) according to claim 1 wherein $R^{1f}$ is 3-(1,3,4-oxadiazol-2-yl)furan-5-yl, furan-2-ylmethylene, 4-(3-methyl-1,2,4-oxadiazol-5-yl)furan-2-yl, 4-(3-methyl-1,2,4-triazol-5-yl)furan-2-yl, 4-(2-methyl-1,3,4-oxadiazol-5-yl)furan-2-yl, 2-carboxyfuran-5-yl, 2-ethoxycarbonylfuran-5-yl, 2-methylaminocarbonylfuran-5-yl, 2-ethylaminocarbonylfuran-5-yl, 2-iso-propylaminocarbonylfuran-5-yl, 3-methylaminocarbonylfuran-5-yl, 3-ethylaminocarbonylfuran-5-yl, 3-iso-propylaminocarbonylfuran-5-yl, 2-methylaminocarbonylthiophen-5-yl, 2-ethylaminocarbonylthiophen-5-yl, 2-iso-propylaminocarbonylthiophen-5-yl, 2-methylaminocarbonylthiophen-4-yl, 2-ethylaminocarbonylthiophen-4-yl, 2-iso-propylaminocarbonylthiophen-4-yl, 2-methoxycarbonylthiophen-4-yl, 2-carboxythiophen-4-yl, 2-methoxycarbonylthiophen-5-yl, 2-carboxythiophen-5-yl, 3-ethoxycarbonylfuran-5-yl, 3-carboxyfuran-5-yl, 3-iso-propylaminocarbonylthiophen-5-yl, 3-ethylaminocarbonylthiophen-5-yl, or 3-methylaminocarbonylthiophen-5-yl.

3. A compound of Formula (If) according to claim 1 wherein the stereochemistry at the position marked "*" is RS or S.

4. A compound of Formula (If) according to claim 2 wherein the stereochemistry at the position marked "*" is RS or S.

5. A compound of Formula (If) according to claim 1 wherein the stereochemistry at the position marked "**" is RS, R, or S.

6. A compound of Formula (If) according to claim 2 wherein the stereochemistry at the position marked "**" is RS, R, or S.

7. A compound of Formula (If) according to claim 3 wherein the stereochemistry at the position marked "**" is RS, R, or S.

8. A compound of Formula (If) according to claim 4 wherein the stereochemistry at the position marked "**" is RS, R, or S.

9. A compound which is: 5-[({[({(2S)-4-[(3,4-dichlorophenyl)methyl]-2-morpholinyl}methyl)amino]carbonyl}amino)methyl]-N-methyl-3-furancarboxamide.

10. A compound which is: 5-[({[({(2S)-4-[(3,4-dichlorophenyl)methyl]-2-morpholinyl}methyl)amino]carbonyl}amino)methyl]-N-(1-methylethyl)-3-furancarboxamide.

11. A compound which is: 5-[({[({(2S)-4-[(3,4-difluorophenyl)methyl]-2-morpholinyl}methyl)amino]carbonyl}amino)methyl]-N-ethyl-3-furancarboxamide.

12. A compound which is: 5-{3-[(2S)-4-(3,4-Dicholorobenzyl)-morpholin-2-ylmethyl]-uriedomethyl}-thiophene-3-carboxylic acid methylamide.

* * * * *

UNITED STATES PATENT AND TRADEMARK OFFICE
CERTIFICATE OF CORRECTION

| | | |
|---|---|---|
| PATENT NO. | : 7,622,464 B2 | Page 1 of 1 |
| APPLICATION NO. | : 10/509162 | |
| DATED | : November 24, 2009 | |
| INVENTOR(S) | : Ancliff et al. | |

It is certified that error appears in the above-identified patent and that said Letters Patent is hereby corrected as shown below:

On the Title Page

Item [*] Notice:   Subject to any disclaimer, the term of this patent is extended or adjusted under 35 USC 154(b) by 444 days Delete the phrase "by 444 days" and insert -- by 1046 days --

Signed and Sealed this

Fourth Day of May, 2010

David J. Kappos
*Director of the United States Patent and Trademark Office*